United States Patent
Chiu et al.

(10) Patent No.: US 12,272,468 B2
(45) Date of Patent: *Apr. 8, 2025

(54) POLYMER-SILICA HYBRID PDOTS AND METHODS OF USE THEREOF

(71) Applicant: University of Washington, Seattle, WA (US)

(72) Inventors: Daniel T. Chiu, Seattle, WA (US); Jiangbo Yu, Bothell, WA (US); Yu Rong, Kenmore, WA (US); Changfeng Wu, Changchun (CN)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,587

(22) Filed: Oct. 11, 2023

(65) Prior Publication Data

US 2024/0047098 A1 Feb. 8, 2024

Related U.S. Application Data

(63) Continuation of application No. 17/368,078, filed on Jul. 6, 2021, now Pat. No. 11,823,809, which is a
(Continued)

(51) Int. Cl.
*H01B 1/00* (2006.01)
*C07K 14/00* (2006.01)
(Continued)

(52) U.S. Cl.
CPC ............... *H01B 1/18* (2013.01); *C07K 14/00* (2013.01); *C07K 16/00* (2013.01); *C08K 3/36* (2013.01);
(Continued)

(58) Field of Classification Search
CPC .... H01B 1/00; H01B 1/12; H01B 1/14; G02F 1/015; G02F 1/061; G02F 1/15
See application file for complete search history.

(56) References Cited

U.S. PATENT DOCUMENTS

| 8,409,876 B2 | 4/2013 | Wiesner et al. |
| 9,260,656 B2 | 2/2016 | Aizawa et al. |
(Continued)

FOREIGN PATENT DOCUMENTS

| CN | 105209916 A | 12/2015 |
| CN | 105517949 A | 4/2016 |
(Continued)

OTHER PUBLICATIONS

Knopp et al "Review: Bioanalytical applications of biomolecule-functionalized nanometer-sized doped silica particles", Analytica Chimica Acta 647 (2009) 14-30.*
(Continued)

*Primary Examiner* — Mark Kopec
(74) *Attorney, Agent, or Firm* — Christensen O'Connor Johnson Kindness PLLC

(57) ABSTRACT

The present disclosure provides organic-inorganic hybrid polymer particles, which have desirable surface chemistry and optical properties that make them particularly suitable for biological and optical applications. The present disclosure also provides methods of making organic-inorganic hybrid polymer particles. The present disclosure also provides methods of using the organic-inorganic hybrid polymer particles for biological and optical applications.

17 Claims, 17 Drawing Sheets

Polymers contain both silane chain and functional chain $R^s$ = silane chain; LX = functional chain silane chain:

$A^0, A^4, A^8 = C_nH_{2n}$ or $C_nF_{2n}$;
$A^1, A^2, A^3, A^5, A^6, A^7, A^9, A^{10}, A^{11} = C_mH_{2m+1}$ or $C_mF_{2m+1}$

L = a linker between the polymer backbone and the functional group X;
X = functional group which contain some active groups: such as amine, carboxylate (or carboxylic), maleimide, -SH, maleic anhydride, NHS (N-Hydroxysuccinimide) ester, etc.

Related U.S. Application Data continuation of application No. 16/900,809, filed on Jun. 12, 2020, now Pat. No. 11,087,900, which is a continuation of application No. 16/309,795, filed as application No. PCT/US2017/037260 on Jun. 13, 2017, now Pat. No. 10,770,197.

(60) Provisional application No. 62/350,126, filed on Jun. 14, 2016.

(51) Int. Cl.

| | | |
|---|---|---|
| *C07K 16/00* | (2006.01) | |
| *C08K 3/36* | (2006.01) | |
| *C08L 83/04* | (2006.01) | |
| *G02F 1/00* | (2006.01) | |
| *G02F 1/015* | (2006.01) | |
| *H01B 1/18* | (2006.01) | |

(52) U.S. Cl.
CPC .............. *C08L 83/04* (2013.01); *G02F 1/015* (2013.01); *C08K 2201/001* (2013.01); *C08L 2203/20* (2013.01)

(56) References Cited

U.S. PATENT DOCUMENTS

| | | | |
|---|---|---|---|
| 10,150,841 | B2 | 12/2018 | Chiu et al. |
| 10,191,060 | B2 | 1/2019 | Chiu et al. |
| 10,502,733 | B2 | 12/2019 | Chiu et al. |
| 2003/0175004 | A1 | 9/2003 | Garito et al. |
| 2008/0276985 | A1 | 11/2008 | Buvat et al. |
| 2009/0243018 | A1 | 10/2009 | Kaerkkaeinen et al. |
| 2010/0184913 | A1 | 7/2010 | Ebbrecht et al. |
| 2012/0190125 | A1 | 7/2012 | Liu et al. |
| 2012/0252140 | A1 | 10/2012 | Aimiya et al. |
| 2012/0282632 | A1 | 11/2012 | Chiu et al. |
| 2014/0350183 | A1* | 11/2014 | Chiu .................. H10K 85/10 526/204 |
| 2016/0161475 | A1 | 6/2016 | Chiu et al. |
| 2019/0157217 | A1 | 5/2019 | Kim et al. |
| 2020/0002480 | A1 | 1/2020 | Okamoto |

FOREIGN PATENT DOCUMENTS

| | | |
|---|---|---|
| JP | 2010-112957 A | 5/2010 |
| WO | 2011/057295 A2 | 5/2011 |
| WO | 2013/101902 A2 | 7/2013 |
| WO | 2014/153051 A1 | 9/2014 |
| WO | 2015/006374 A1 | 1/2015 |
| WO | 2017/218541 A1 | 12/2017 |

OTHER PUBLICATIONS

Blanco-Canosa et al "Recent progress in the bioconjugation of quantum dots", Coordination Chemistry Reviews 263-264 (2014) 101-137.*

European Office Action mailed Aug. 12, 2020, for European Patent Application No. 17813936.6, filed on Jun. 13, 2017, 4 pages.
Ravindranath, R. et al., "Synthesis and Characterization of Luminescent Conjugated Polymer-Silica Composite Spheres," Chemistry of Materials, pp. 1213-1218, Jan. 2006.
Geng, J. et al., "A general approach to prepare conjugated polymer dot embedded silica nanoparticles with a SiO2@CP@SiO2 structure for targeted HER2-positive cellular imaging," Nanoscale, 5(18):8593-8601, Jan. 2013.
Behrendt, J.M. et al., "Hybrid inorganic-organic composite nanoparticles from crosslinkable polyfluorenes," Journal of Materials Chemistry C, 1(20):3297-3304, Jan. 2013.
Supplementary European Search Report mailed Dec. 5, 2019, for European Patent Application No. 17813936.6, filed on Jun. 13, 2017, 9 pages.
Office Action mailed Sep. 23, 2020, for Chinese Patent Application No. 201780037417.7, with English translation, 16 pages.
Office Action dated Feb. 3, 2020, for Chinese Patent Application No. 201780037417.7, with English translation, 16 pages.
Evans, R.C., "Fluorene Based Conjugated Polyelectrolyte/ Silica Nanocomposites: Charge-Mediated Phase Aggregation at the Organic-Inorganic Interface," Advanced Materials, 22:3032-3037, 2010.
Evans, R.C., et al., "Chain confinement promotes beta-phase formation in polyfluorene-based photoluminescent ionogels," Chem. Commun., 48:3742-3744, 2012.
Sanchez, C., et al., "Optical Properties of Functional Hybrid Organic-Inorganic Nanocomposites," Advanced Materials, 15(23):1969-1994, Dec. 2003.
Imai, Y., et al., "Isomerization Behavior of Azobenzene Chromophores Attached to the Side Chain of Organic Polymer in Organic-Inorganic Polymer Hybrids," Macromolecules, 32(4):1013-1017, 1999.
International Search Report and Written Opinion dated Aug. 11, 2017, for International Patent Application No. PCT/US2017/ 037260.
Geng, J., et al., "Micelle/Silica Co-protected Conjugated Polymer Nanoparticles for Two-Photon Excited Brain Vascular Imaging," Chem. Mater., 26:1874-1880, 2014.
Mcneill, J.D., et al., "Bioconjugated polymer dot nanoparticles," Polymer Preprints, 48(2):23-24, 2007.
Wu, C. et al., "Preparation and Encapsulation of Highly Fluorescent Conjugated Polymer Nanoparticles," Langmuir, 22(7):2956-2960, 2006.
Second Chinese Office Action mailed Dec. 3, 2020, in Chinese Patent Application No. 201780037417.7, 16 pages.
Japanese Office Action mailed Mar. 4, 2021, in Japanese Patent Application No. 2018-565049, with English translation, 7 pages.
First Chinese Office Action mailed on Jan. 18, 2023, issued in corresponding Chinese Application No. 202210347705.5, filed on Jun. 13, 2017, and its English translation thereof, 16 pages.
English Translation of the Chinese Office Action mailed on Aug. 9, 2023, issued in the corresponding Chinese Application No. 202210347705.5, filed on Jun. 13, 2017, 14 pages.

* cited by examiner

In THF solution: Polymer/alkyl-silane/silane(optional)
/silane with functional groups (optional)
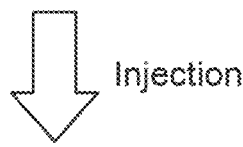
Injection
Water/Aqueous Solution/ Silane with functional groups
soluble in water (optional)
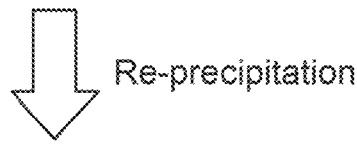
Re-precipitation
Hybrid Pdots with functional groups
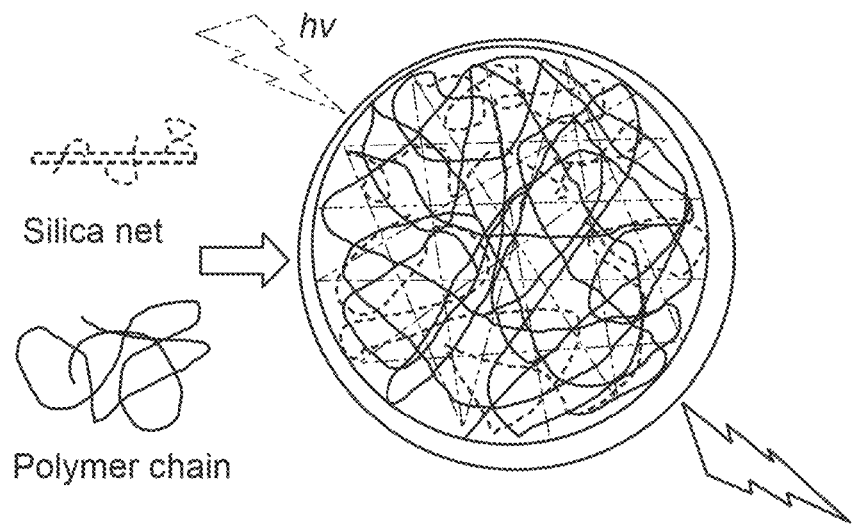
FIG. 1

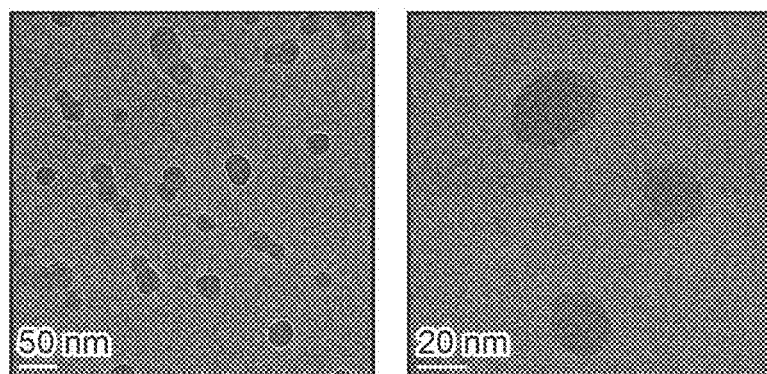
PFBT bare Pdots
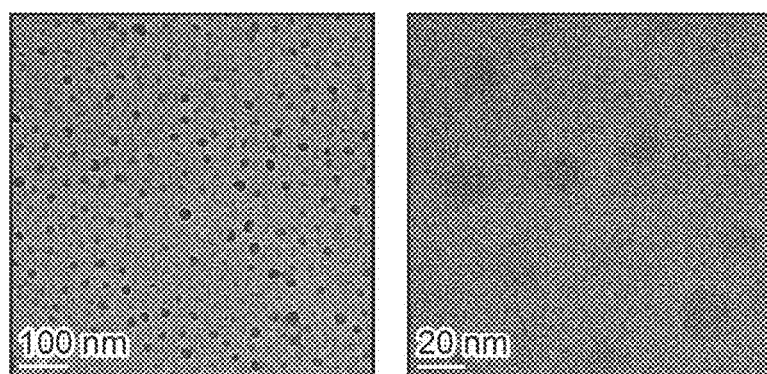
PFBT/TMOS/TEOS hybrid Pdots
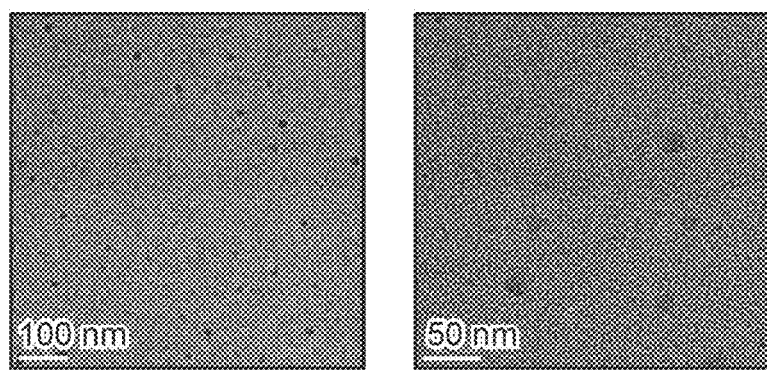
PFBT/TCOS/TEOS hybrid Pdots
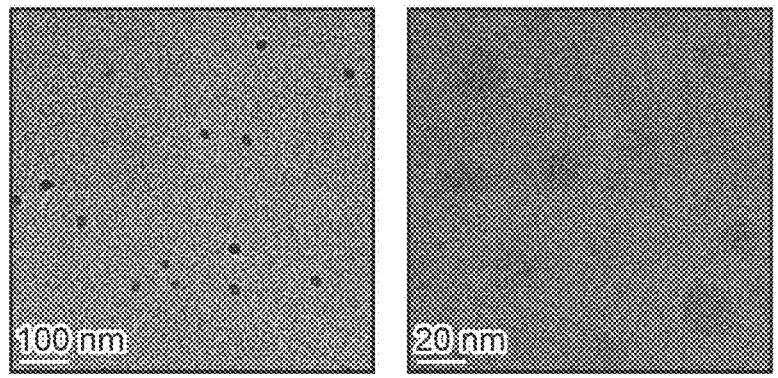
MEHPPV/TMOS/TEOS hybrid Pdots
FIG. 3

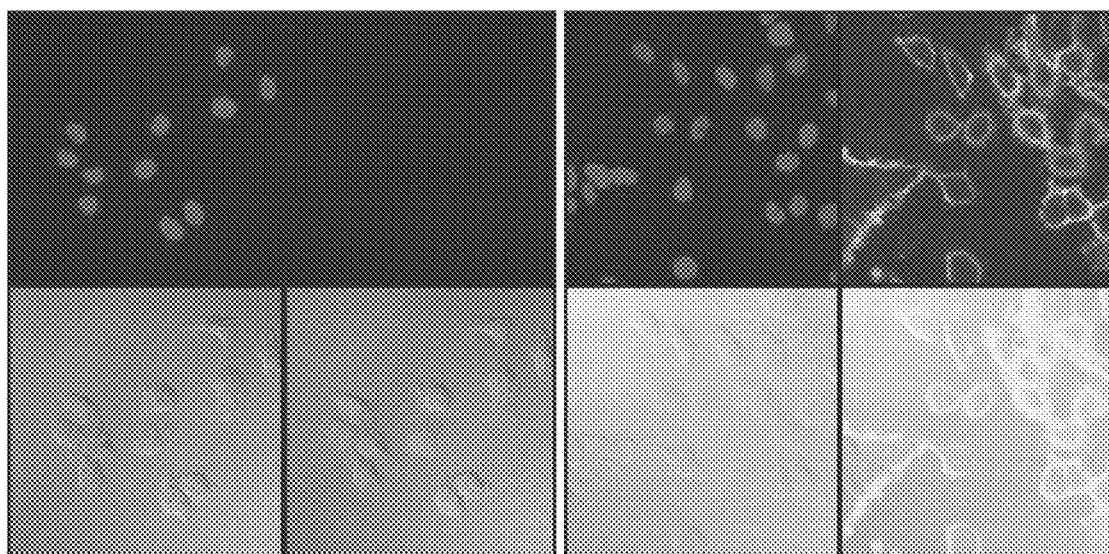
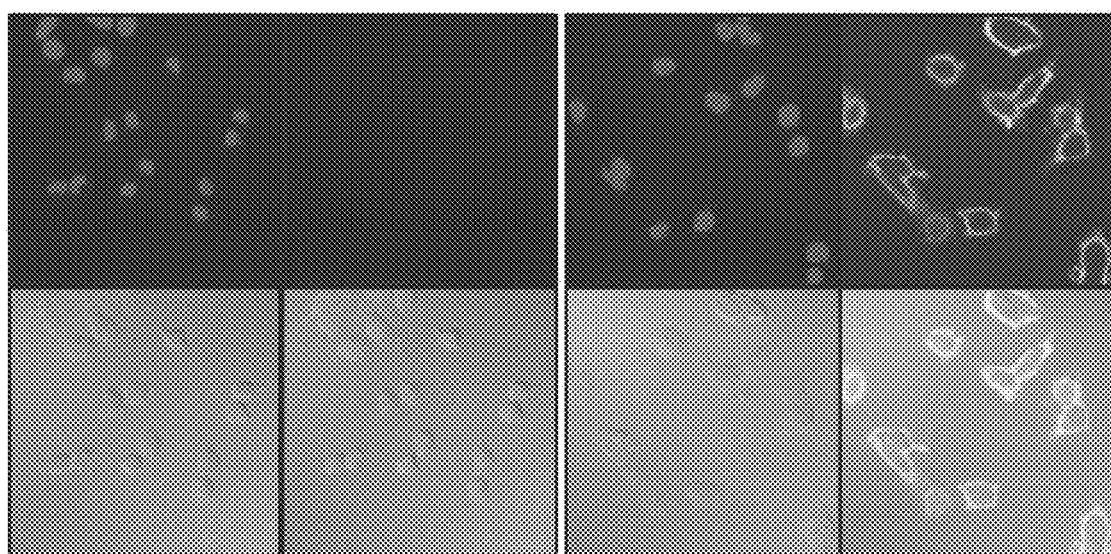
FIG. 6

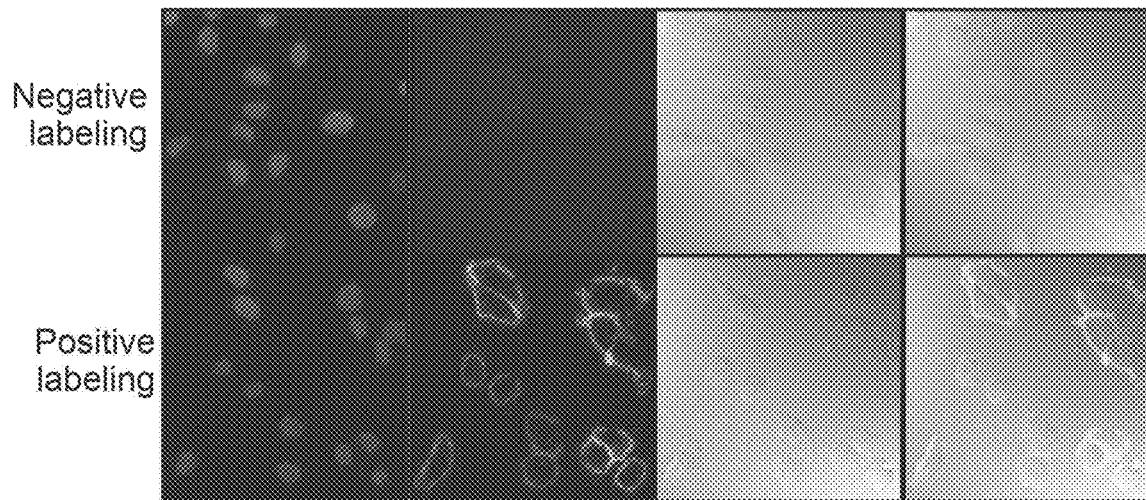
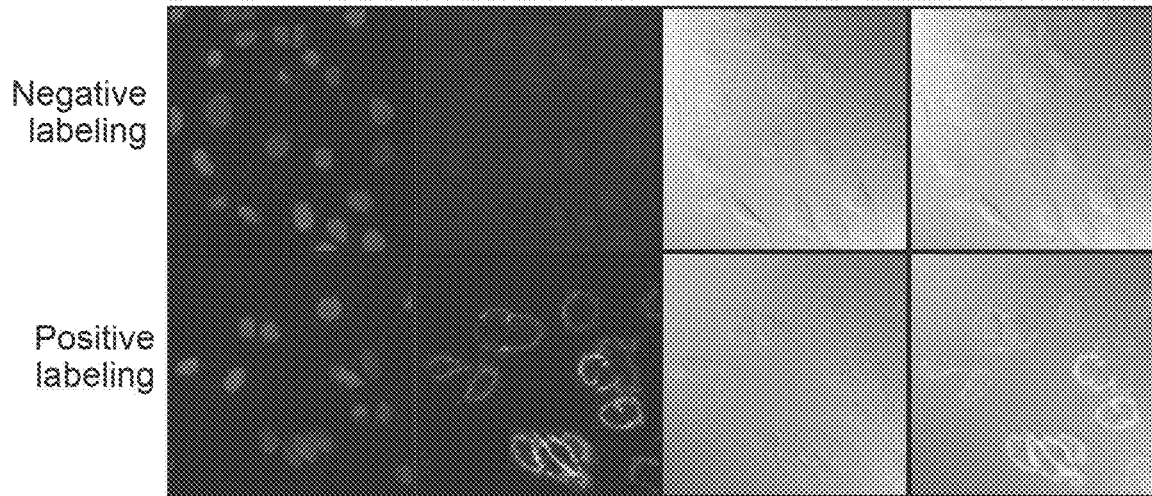
FIG. 8

Lane: Sample:
1  PFBT
2  PFBT/TMOS/TEOS-1 (2:1:1)
3  PFBT/TMOS/TEOS-1 (2:1:1)-SA
4  PFBT/TMOS/TEOS-2 (2:2:2)
5  PFBT/TMOS/TEOS-2 (2:2:2)-SA
6  PFBT/TMOS/TEOS-3 (2:2:16)
7  PFBT/TMOS/TEOS-3 (2:2:16)-SA

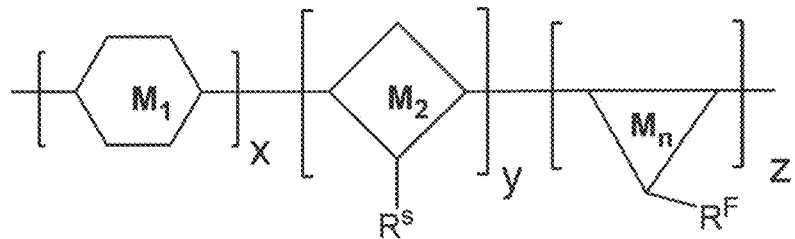

Polymers contain both silane chain and functional silane chain $R^S$ = silane chain; $R^F$ = functional silane chain silane chain:

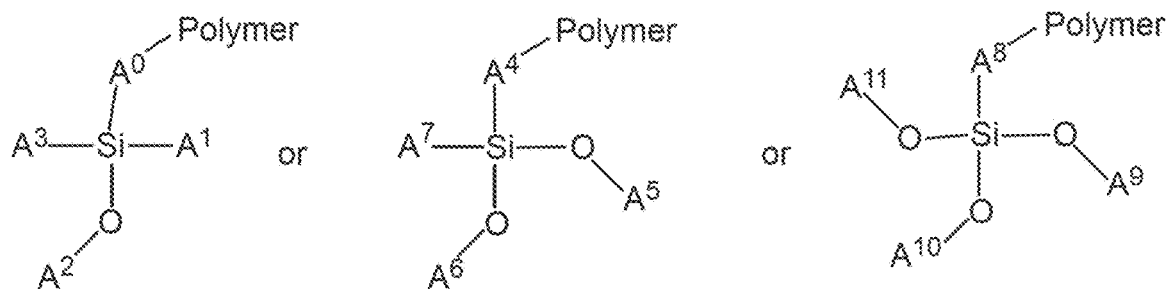

functional silane chain:

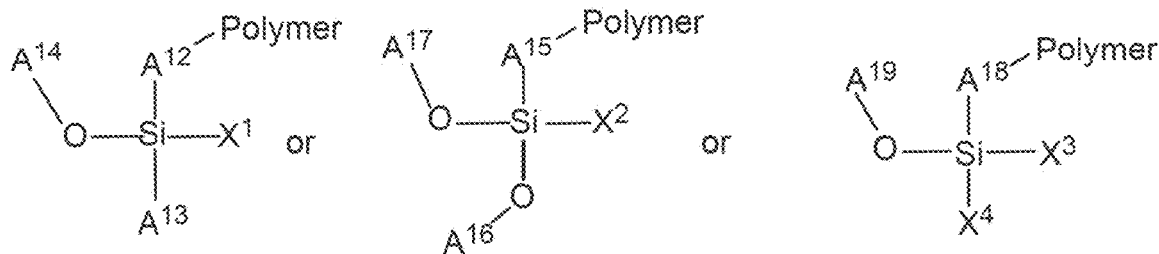

$A^0, A^4, A^8, A^{12}, A^{15}, A^{18} = C_nH_{2n}$ or $C_nF_{2n}$;

$A^1, A^2, A^3, A^5, A^6, A^7, A^9, A^{10}, A^{11}, A^{13}, A^{14}, A^{16}, A^{17}, A^{19} = C_mH_{2m+1}$ or $C_mF_{2m+1}$ $X^1, X^2, X^3$ and $X^4$ = functional group which contain some active groups: such as amine, carboxylate (or carboxylic), maleimide, -SH, maleic anhydride, NHS (N-Hydroxysuccinimide) ester, etc.

FIG. 12

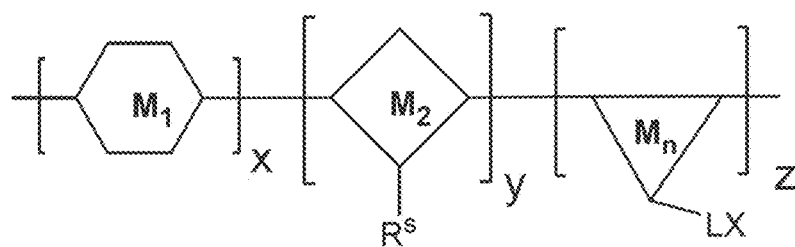

Polymers contain both silane chain and functional chain $R^S$ = silane chain; LX = functional chain silane chain:

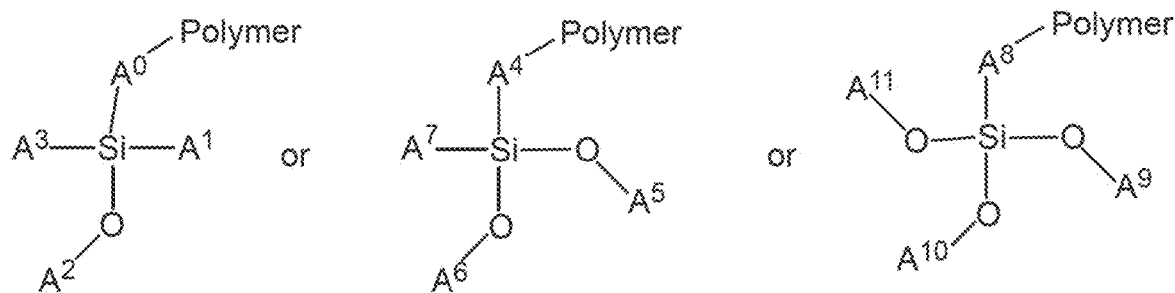

$A^0, A^4, A^8 = C_nH_{2n}$ or $C_nF_{2n}$;

$A^1, A^2, A^3, A^5, A^6, A^7, A^9, A^{10}, A^{11} = C_mH_{2m+1}$ or $C_mF_{2m+1}$

L = a linker between the polymer backbone and the functional group X;
X = functional group which contain some active groups: such as amine, carboxylate (or carboxylic), maleimide, -SH, maleic anhydride, NHS (N-Hydroxysuccinimide) ester, etc.

FIG. 13

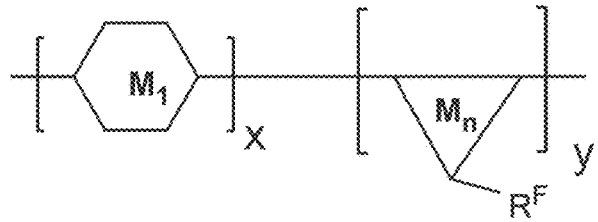
Polymers contain functional silane chain
$R^F$ = functional silane chain
functional silane chain:
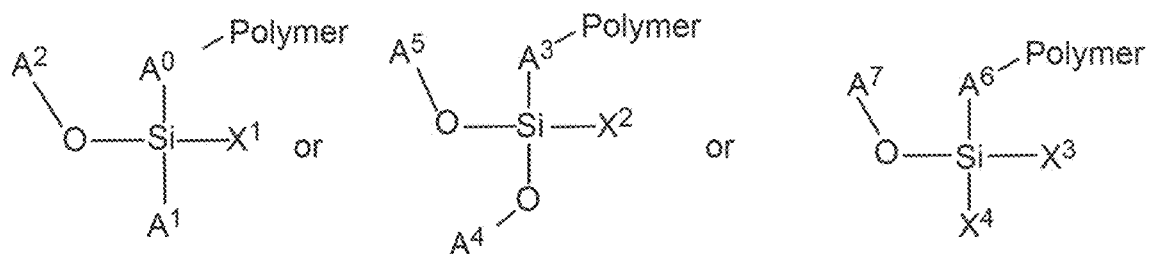
$A^0, A^3, A^6 = C_nH_{2n}$ or $C_nF_{2n}$;
$A^1, A^2, A^4, A^5 = C_mH_{2m+1}$ or $C_mF_{2m+1}$
$X^1, X^2, X^3$ and $X^4$ = functional group which contain some active groups: such as amine, carboxylate (or carboxylic), maleimide, -SH, maleic anhydride, NHS (N-Hydroxysuccinimide) ester, etc.
FIG. 14

PFBT-14%C₂COOH/TCOS/TEOS hybrid Pdots

POLYMER-SILICA HYBRID PDOTS AND METHODS OF USE THEREOF

CROSS REFERENCES TO RELATED APPLICATIONS

This application is a Continuation of co-pending U.S. patent application Ser. No. 17/368,078, filed Jul. 6, 2021, now U.S. Pat. No. 11,823,809, issued Nov. 21, 2023, which is a Continuation of U.S. patent application Ser. No. 16/900,809, filed Jun. 12, 2019, now U.S. Pat. No. 11,087,900, issued Aug. 10, 2021, which is a Continuation of U.S. patent application Ser. No. 16/309,795, filed Dec. 13, 2018, now U.S. Pat. No. 10,770,197, issued Sep. 8, 2020, which is a U.S. National Phase Application under 35 U.S.C. § 371 of International Patent Application No. PCT/US2017/037260, filed Jun. 13, 2017, now expired, which claims the benefit of U.S. Provisional Patent Application No. 62/350,126, filed Jun. 14, 2016, now expired, the disclosures of which are incorporated herein by reference in their entireties.

BACKGROUND

Advances in understanding biological systems have relied on applications of fluorescence microscopy, flow cytometry, versatile biological assays, and biosensors. These experimental approaches make extensive use of organic dye molecules as probes. But intrinsic limitations of these conventional dyes such as low absorptivity, and poor photostability have posed great difficulties in further developments of high-sensitivity imaging techniques and high-throughput assays. As a result, there has been considerable interest in developing brighter and more photostable fluorescent nanoparticles.

Traditional chromophoric polymer dots have been studied for imaging and detection techniques for researching chemical and biological analytes and systems. Functionalization of chromophoric polymer dots for use in bioconjugation has been attempted, but problems with polymer dot swelling, instability, and aggregation in biological buffer solutions, as well as nonspecific interactions in certain environments have been encountered.

SUMMARY

The present disclosure provides a new class of organic-inorganic hybrid polymer dots and related methods.

In various aspects, the present disclosure provides an organic-inorganic hybrid polymer dot comprising: a semiconducting chromophoric polymer; and an inorganic network, wherein the semiconducting chromophoric polymer and the inorganic network form an organic-inorganic interpenetrated network.

In various aspects, the present disclosure provides a method of making an organic-inorganic hybrid polymer dot, the method comprising: providing a solution, wherein the solution comprises a solvent, a semiconducting chromophoric polymer, and an organo-silane; and mixing the solution with an aqueous solution, wherein at least one of the solution or the aqueous solution comprises an organo-silane comprising X, wherein X is a functional group suitable for bioconjugation. Preferably or optionally, the solution can also comprise an additional silane that can help to make the hybrid polymer dot smaller and/or more compact.

In various aspects, the present disclosure provides an organic-inorganic interpenetrated hybrid chromophoric polymer dot comprising a semiconducting chromophoric polymer, an inorganic network, and a functional group that is suitable for bioconjugation.

In various aspects, the present disclosure provides an organic-inorganic hybrid polymer dot comprising: a semiconducting chromophoric polymer; X, wherein X is a functional group suitable for bioconjugation; and an inorganic network that is covalently bonded to the semiconducting chromophoric polymer.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 provides a schematic illustration of a method for preparing hybrid polymer dots.

FIG. 3 illustrates Transmission Electron Microscopy (TEM) images of the hybrid polymer dots.

FIG. 6 shows fluorescence imaging of MCF cells specifically labeled with the hybrid polymer dot bioconjugates based on the blending set of PFBT/TMOS/TEOS.

FIG. 8 shows fluorescence imaging of MCF cells specifically labeled with the hybrid polymer dot bioconjugates based on the blending set of PFBT/TCOS/TEOS.

FIG. 12 provides a general schematic illustration of conjugated polymers with a silane chain and functional silane chain for bioconjugation.

FIG. 13 provides a general schematic illustration of conjugated polymers with a silane chain and functional chain for bioconjugation.

FIG. 14 provides a general schematic illustration of conjugated polymers with a functional silane chain for bioconjugation.

DETAILED DESCRIPTION

Figure 2:
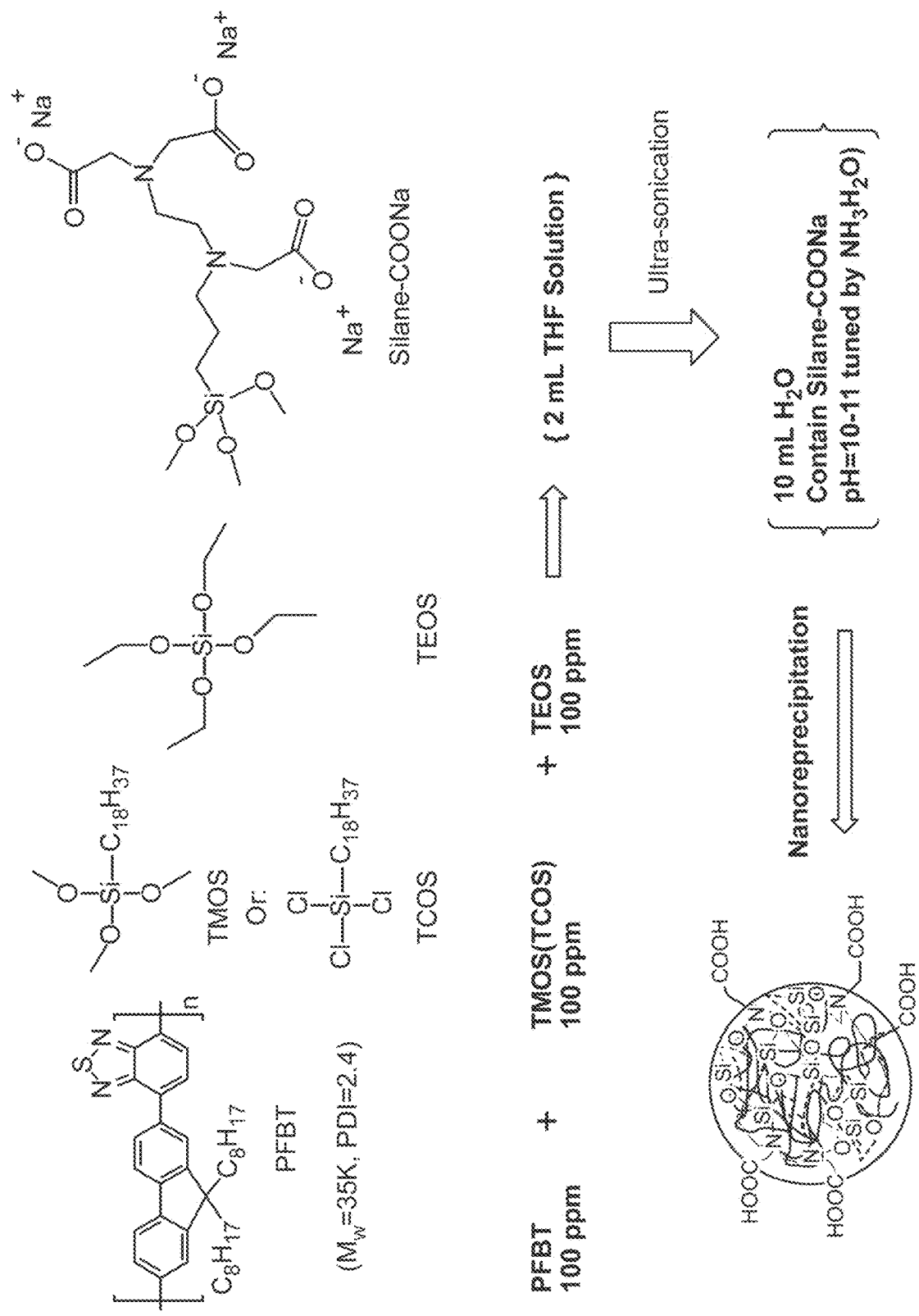
FIG. 2 illustrates a method of preparing carboxylate functionalized PFBT hybrid polymer dots.

The present disclosure provides compositions of, as well as related methods of making and using, organic-inorganic hybrid polymer dots, which have desirable surface chemistry and optical properties that make them particularly suitable for biological applications. These and other embodiments are described in detail herein.

The invention will best be understood by reference to the following detailed description of the embodiments and embodiments of the invention, taken in conjunction with the accompanying drawings and figures. The discussion below is descriptive, illustrative, and exemplary and is not to be taken as limiting the scope defined by any appended claims.

Various polymer compositions are suitable for use with the embodiments herein. In some embodiments, a "polymer" is a molecule composed of at least two repeating structural units typically connected by covalent chemical bonds. A polymer of the present disclosure can have different kinds of repeating units, for example, 2, 3, 4, 5, 6, 7, 8, 9, or 10 different kinds of repeating units. The repeating structural unit may be one type of monomer, and the resulting polymer is a homopolymer. In some embodiments, the polymers can include two different types of monomers, three different types of monomers, four different types of monomers, five different types of monomers, or more types of monomers. One of ordinary skill in the art will appreciate that the different types of monomers can be distributed along a polymer chain in a variety of ways. For example, three different types of monomers can be randomly distributed along the polymer. It will similarly be appreciated that the distribution of monomers along the polymer can be represented in different ways. The number of repeating structural units (e.g., monomers) along the length of a polymer can be represented by "n." In some embodiments, n can range, e.g., from at least 2, from at least 10, from at least 50, from at least 100, from at least 500, from at least 1,000, from at least 10,000, or higher. In certain embodiments, n can range from 2 to 10,000, from 10 to 10,000, from 10 to 1,000, from 20 to 5,000, from 20 to 500, from 50 to 300, from 100 to 1,000, from 100 to 10,000, or from 500 to 10,000.

In some embodiments, polymers have extended molecular structures comprising backbones that optionally contain pendant side groups. The polymers provided herein can include, but are not limited to, linear polymers and branched polymers such as star polymers, comb polymers, brush polymers, ladders, and dendrimers. As described further herein, the polymers can include semiconducting polymers generally well known in the art.

In some embodiments, a "polymer particle," "polymeric particle," or "Pdot" is a sub-micrometer-sized entity, which represents a separate discontinuous phase surrounded by a continuous free-flowing medium. The free flowing medium is usually a low-molecular-weight liquid, most often water. In some embodiments, the terms "polymer particle," "polymeric particle," or "Pdot" can be used interchangeably.

In some embodiments, the terms "polymer particle," "hybrid polymer dot," "polymer dot," "chromophoric polymer dot," "chromophoric semiconducting polymer dot," "fluorescent polymer dot," "chromophoric nanoparticle" and "Pdot" are used interchangeably to refer to structures comprising one or more polymers (e.g., semiconducting polymers, non-semiconducting polymers, or a combination thereof) that have been collapsed into a stable sub-micron-sized particle. Various methods are suitable for forming hybrid polymer dots, as described further herein. The hybrid polymer dots provided herein can be made up of a single polymer or can comprise blends of polymers. In certain embodiments, the one or more polymers are collapsed, precipitated, and/or condensed to form a polymer matrix. In some embodiments, the properties of the hybrid polymer dots are dependent on the polymer structures. Therefore, the polymer backbone (main chain), side chains, terminal units, and substituted groups can be varied to obtain specific properties. In some embodiments, the optical properties of the hybrid polymer dots can be tuned by varying the structures of the polymer backbone (main chain).

In certain embodiments, the hybrid polymer dots provided herein include one or more chromophores, also referred to herein as chromophoric units. In some embodiments, the term "chromophore" or "chromophoric unit" is given its ordinary meaning in the art. A chromophore absorbs certain wavelengths of light, e.g., from the UV region to the near infrared region, and may be or may not be emissive. In some embodiments, a chromophoric unit includes, but is not limited to, a unit of structures with delocalized pi-electrons, a unit of small organic dye molecules, and/or a unit of metal complexes. The chromophore can be part of the polymer matrix or be incorporated into the polymer matrix, e.g., by blending, crosslinking, and the like.

In certain embodiments, the hybrid polymer dots of the present disclosure include one or more chromophoric polymers. In some embodiments, the term "chromophoric polymer" refers to a polymer in which at least a portion of the polymer absorbs certain wavelengths of light, e.g., ranging from UV to near infrared spectra. Chromophoric polymers according to the present disclosure may be or may not be emissive. In some embodiments, a "chromophoric polymer" is a polymer in which at least a portion of the polymer includes chromophoric units. Examples of chromophoric polymers can include polymers comprising units of structures with delocalized pi-electrons such as semiconducting polymers, polymers comprising units of small organic dye molecules, polymers comprising units of metal complexes, and polymers comprising units of any combinations thereof. The chromophoric unit can be incorporated into the polymer backbone. The chromophoric unit can also be covalently attached to the side chain, or the terminal unit of the polymer. Chromophoric polymers can be made using standard synthesis methods generally well known in the art.

In certain embodiments, the chromophoric polymer is a "conjugated polymer." The term "conjugated polymer" is recognized in the art. Electrons, holes, or electronic energy, can be conducted along the conjugated structure. In some embodiments, a large portion of the polymer backbone can be conjugated. In some embodiments, the entire polymer backbone can be conjugated. In some embodiments, the polymer can include conjugated structures in their side chains or termini. In some embodiments, the conjugated polymer can have conducting properties, e.g., the polymer can conduct electricity. In some embodiments, the conjugated polymer can have semiconducting properties, e.g., the polymers can exhibit a direct band gap, leading to an efficient absorption or emission at the band edge. Therefore, in certain embodiments, the chromophoric polymer is a "semiconducting polymer." The term "semiconducting polymer" is recognized in the art.

In some embodiments, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

In some embodiments, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

In some embodiments, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

In some embodiments, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

In some embodiments, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec butynylene, pentynylene and hexynylene.

In some embodiments, the term "alkyl amine" refers to an alkyl group as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

In some embodiments, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, and the like.

In some embodiments, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

In some embodiments, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

In some embodiments, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—.

In some embodiments, the term "heterocycloalkylene" refers to a heterocycloalkyl group, as defined above, linking at least two other groups. The two moieties linked to the heterocycloalkylene can be linked to the same atom or different atoms of the heterocycloalkylene.

In some embodiments, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl.

Alkylenedioxy is a divalent substitute attached to two adjacent carbon atoms of phenyl, e.g., methylenedioxy or ethylenedioxy. Oxy-$C_2$-$C_3$-alkylene is also a divalent substituent attached to two adjacent carbon atoms of phenyl, e.g., oxyethylene or oxypropylene. An example for oxy-$C_2$-$C_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

In some embodiments, the terms "alkoxy-aryl" refers to an aryl group, as defined above, where one of the moieties linked to the aryl is linked through an oxygen atom. Alkoxy-aryl groups include, but are not limited to, phenoxy ($C_6H_5O$—). The present disclosure also includes alkoxy-heteroaryl groups.

In some embodiments, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g., alkyl, nitro or halogen. Similarly, aryl and heteroaryl groups described herein can be substituted or unsubstituted. Substituents for the aryl and heteroaryl groups are varied, such as alkyl, aryl, CN, amino, sulfide, aldehyde, ester, ether, carboxyl, hydroxyl or halide. Substituents can be a reactive group, such as but not limited to chloro, bromo, iodo, hydroxyl, or amino. Substituents can be selected from: halogen, OR', OC(O)R', NR'R", SR', R', CN, $NO_2$, $CO_2$R', CONR'R", C(O)R', OC(O)NR'R", NR"C(O)R', NR"C(O)$_2$R', NR'C(O)NR"R''', NH C($NH_2$)=NH, NR'C($NH_2$)=NH, NH C($NH_2$)=NR', S(O)R', S(O)$_2$R', S(O)$_2$NR'R", $N_3$, CH(Ph)$_2$, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

The groups described herein can be substituted or unsubstituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, carboxyl, hydroxyl or halide. Substituents can be a reactive group, such as but not limited to chloro, bromo, iodo, hydroxyl, or amino. Suitable substituents can be selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R''' each independently refer to hydrogen, unsubstituted ($C_1$-$C_8$)alkyl and heteroalkyl, unsubstituted aryl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

As used herein and in the appended claims, the singular forms "a," "and," and "the" include plural referents unless the context clearly dictates otherwise. Thus, for example, reference to "a compound" includes a plurality of such compounds, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

As used herein the term "and/or" is used as a functional word to indicate that two words or expressions are to be taken together or individually. For example, A and/or B encompasses A alone, B alone, and A and B together.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure provided herein.

Unless defined otherwise, all technical and scientific terms used herein have the same meaning as commonly understood to one of ordinary skill in the art to which this disclosure belongs. Although any methods, devices, and materials similar or equivalent to those described herein can be used in the practice or testing of the disclosure, the preferred methods, devices and materials are now described.

Organic-Inorganic Hybrid Polymer Dots

The present disclosure provides various embodiments of organic-inorganic hybrid polymer dots, also referred to herein as "hybrid polymer dots." In some embodiments, an organic-inorganic hybrid polymer dot comprises an organic network and an inorganic network. In certain embodiments, the organic network includes at least one organic species, such as one or more of the chromophoric polymers described herein. In certain embodiments, an inorganic network comprises at least one inorganic species, such as siloxane, alumino-siloxane, titanium-siloxane, titanium oxide, or a combination thereof. In certain embodiments, an inorganic network is a siloxane network (e.g., including Si—O—Si linkages), an alumino-siloxane network (e.g., including Al—O—Si linkages), a titanium-siloxane network (e.g., including Ti—O—Si linkages), a titanium oxide network (e.g., including Ti—O—Ti linkages), or a combination thereof. Additional examples of inorganic networks such as siloxane networks are discussed in further detail herein. The terms "siloxane network" and "silica ($SiO_2$) network" treated synonymously herein.

In some embodiments, the organic network and inorganic network are interpenetrated with each other so as to form an organic-inorganic interpenetrated network. For example, a siloxane network can form an interpenetrated network with a chromophoric polymer. As used herein, an "organic-inorganic interpenetrated network" refers to the polymer dot matrix comprising at least two networks that together form the interpenetrated network. In some embodiments, the organic-inorganic interpenetrated network is mesh-like and/or an interlocking structure of the inorganic network interpenetrated with the polymer. In some embodiments, interpenetration occurs primarily through the physical association (e.g., hydrophobic interaction) of the at least two networks so as to form the interpenetrated network. In certain embodiments, interpenetration occurs through the physical association of the at least two networks without any chemical bonding (e.g., without covalent bonding between the two networks). In certain embodiments, interpenetration occurs primarily through the chemical bonding (e.g., covalent bonding) of the two networks to each other so as to form the interpenetrated network. Covalent bonding between the organic network and inorganic network can be used alternatively to or in combination with physical association in order to form the organic-inorganic interpenetrated network.

In certain embodiments, the present disclosure provides organic-inorganic hybrid polymer dots that are structurally distinct from other types of polymer dots and particles, included but not limited to polymer dots formed by blending (e.g., polymer dots blended with amphiphilic polymers) and polymer dots without an inorganic network. For example, in some embodiments, the organic-inorganic interpenetrated network of the hybrid polymer dots described herein is distinct from a core-cap or core-shell structure that may be found in other types of polymer dots. In certain embodiments, the organic-inorganic hybrid polymer dots herein do not include a core-cap or core-shell structure.

As described in further detail herein, in some embodiments, the organic-inorganic interpenetrated network is formed during formation of the organic-inorganic hybrid polymer dot. For example, in some embodiments, formation of an organic-inorganic hybrid polymer dot involves forming a siloxane network during hydrolysis of organic silane molecules. In certain embodiments, the organic silane is an alkylsilane. In certain embodiments, one or more polymers are collapsed, precipitated, or condensed simultaneously with hydrolysis of organic silane molecules and cross linking in order to simultaneously form an organic network and an inorganic network, which together form the organic-inorganic interpenetrated network.

The weight percent of the inorganic network (e.g., siloxane network) and/or the components thereof (e.g., silicon (Si)) in a hybrid polymer dot can be varied as desired. In some embodiments, the weight percent of the inorganic network (e.g., siloxane network) and/or the components thereof (e.g., silicon) is selected to avoid formation of a core-shell structure in the resulting hybrid polymer dot. In certain embodiments, the weight percent of silicon from the inorganic network in the hybrid polymer dot is less than or equal to about 1%, less than or equal to about 5%, less than or equal to about 10%, less than or equal to about 15%, less than or equal to about 20%, less than or equal to about 25%, less than or equal to about 30%, less than or equal to about 35%, less than or equal to about 40%, less than or equal to about 45%, or less than or equal to about 47%. In certain embodiments, the weight percent of silicon from the inorganic network in the hybrid polymer dot is greater than or equal to about 1%, greater than or equal to about 5%, greater than or equal to about 10%, greater than or equal to about 15%, greater than or equal to about 20%, greater than or equal to about 25%, greater than or equal to about 30%, greater than or equal to about 35%, greater than or equal to about 40%, or greater than or equal to about 45%. In certain embodiments, the weight percent of silicon from the inorganic network in the hybrid polymer dot is within a range from about 1% to about 45%, or within a range from about 1% to about 47%.

The hybrid polymer dots of the present disclosure can be functionalized and/or bioconjugated, e.g., to a biological molecule. In some embodiments, a hybrid polymer dot includes an organic network (e.g., a semiconducting chromophoric polymer), an inorganic network (e.g., a siloxane network), and X, where X is a functional group suitable for bioconjugation. Examples of functional groups and/or linkers suitable for bioconjugation in accordance with the present disclosure are provided further below. The functional group X may be attached to the inorganic network, the organic network, or a combination thereof. In certain embodiments the functional group is attached to the inorganic network. In certain embodiments the functional group is attached to the semiconducting chromophoric polymer. In certain embodiments the functional group comprises a hydrophobic functional group, a hydrophilic functional group, or a combination thereof. In certain embodiments the functional group is suitable for bioconjugation.

In some embodiments, a hybrid polymer dot includes at least two orthogonal reactive chemical groups. In certain embodiments, an orthogonally reactive chemical group is a chemical group that reacts only with its designated chemical reactive group, but not with another chemical reactive group that may be present. For example, reactive groups A and B can form a designated pair that reacts with each other, and reactive groups Y and Z can form another designated pair that reacts with each other. In such embodiments, reactive group A is considered to be orthogonal with respect to Y because A does not react with Z, and reactive group Y is orthogonal with respect to A because Y does not react with B. In some embodiments, reactive groups A can react with each other or with reactive groups B to form a siloxane network, and reactive groups Y do not react with either A or B, such that A and Y, and/or B and Y, are considered to be orthogonal reactive groups.

In some embodiments, the hybrid polymer dot includes a semiconducting chromophoric polymer that includes at least two orthogonal reactive chemical groups. In certain embodiments, at least one of the orthogonal reactive chemical groups has the formula $C_nH_{2n}X$ or $C_nF_{2n}X$, wherein X is a functional group suitable for bioconjugation as described further herein and n is not less than 1.

In some embodiments, organic-inorganic hybrid polymer dots comprise at least two inorganic species, each having its own respective function. For example, the organic-inorganic hybrid polymer dots can have a surface that is functionalized with a functional species comprising a carboxyl, an amine, a thiol (—SH), a carboxylate or carboxylic acid, a maleimide, a maleic anhydride, a N-hydroxysuccinimide (NHS), an alcohol (—OH), or a cyanate, or a combination thereof that is suitable for bioconjugation, as discussed further herein.

Additionally, hybrid polymer dots can comprise an aliphatic chain, for example, an alkyl chain. The aliphatic chain can take part in cross-linking during formation of the interpenetrated network. The aliphatic chain can be physically associated with the organic network (e.g., chromophoric polymer) and/or the inorganic network during formation of the interpenetrated network.

The resulting hybrid polymer dots display a set of advantageous properties for biological applications. For example, the organic-inorganic interpenetrated network of the hybrid polymer dots allows for robust, compact polymer dots with high fluorescence brightness by, for example, preventing undesirable chain-chain interactions. For example, the interpenetrated network of the hybrid polymer dots may decrease undesirable fluorescent quenching. The organic-inorganic hybrid polymer dots exhibit high fluorescence quantum yield, improved photostability, and improved colloidal stability. Therefore, the fluorescence quantum yield and photostability of the hybrid polymer dots can be significantly improved. The hybrid polymer dots are stable in a range of biological media and do not swell or form aggregates in a variety of biological buffers.

As used herein, the term "stable," in reference to polymer dots, can refer to polymer dots that do not aggregate and/or change substantially in size (as measured by electron microscopy, atomic force microscopy, or dynamic light scattering) when stored in an appropriate aqueous solution for an extended period of time. Aggregation or a change substantially in size of the polymer dots can, for example, be characterized as an increasing number of aggregates including more than one polymer dot. Aggregates can be detected visually by the eye, with imaging techniques, such as electron microscopy or atomic for microscopy, and/or by increased size measurements shown by dynamic light scattering.

In some embodiments, hybrid polymer dots can have a diameter of not less than 5 nm and not greater than 1,000 nm. In some embodiments, the organic-inorganic hybrid polymer dots disclosed herein can have a diameter of not less than 5 nm and not greater than 500 nm. In some embodiments, the organic-inorganic hybrid polymer dots disclosed herein can have a diameter of not less than 5 nm and not greater than 100 nm. In some embodiments, the organic-inorganic hybrid polymer dots disclosed herein can have a diameter of not less than 5 nm and not greater than 50 nm. In some embodiments, the organic-inorganic hybrid polymer dots disclosed herein can have a diameter of not less than 10 nm and not greater than 30 nm. In some embodiments, the organic-inorganic hybrid polymer dots disclosed herein can have a diameter of not greater than 100 nm. In some embodiments, the organic-inorganic hybrid polymer dots disclosed herein can have a diameter not greater than 50 nm. In some embodiments, the organic-inorganic hybrid polymer dots disclosed herein can have a diameter of not greater than 40 nm. In some embodiments, the organic-inorganic hybrid polymer dots disclosed herein can have a diameter of not greater than 30 nm. In some embodiments, the organic-inorganic hybrid polymer dots disclosed herein can have a diameter of not greater than 20 nm. In some embodiments, the organic-inorganic hybrid polymer dots disclosed herein can have a diameter of not less than 5 nm and not greater than 300 nm. In some embodiments, the organic-inorganic hybrid polymer dots disclosed herein can have a diameter of not less than 5 nm and not greater than 200 nm. In some embodiments, the organic-inorganic hybrid polymer dots disclosed herein can have a diameter of not less than 5 nm and not greater than 150 nm. In some embodiments, the organic-inorganic hybrid polymer dots disclosed herein can have a diameter of not less than 5 nm and not greater than 90 nm. In some embodiments, the organic-inorganic hybrid polymer dots disclosed herein can have a diameter of not less than 5 nm and not greater than 80 nm. In some embodiments, the organic-inorganic hybrid polymer dots disclosed herein can have a diameter of not less than 5 nm and not greater than 70 nm. In some embodiments, the organic-inorganic hybrid polymer dots disclosed herein can have a diameter of not less than 5 nm and not greater than 60 nm. In some embodiments, the organic-inorganic hybrid polymer dots disclosed herein can have a diameter of not less than 5 nm and not greater than 40 nm. In some embodiments, the organic-inorganic hybrid polymer dots disclosed herein can have a diameter of not less than 5 nm and not greater than 30 nm. In some embodiments, the organic-inorganic hybrid polymer dots disclosed herein can have a diameter of not less than 5 nm and not greater than 25 nm.

The attributes of the organic-inorganic hybrid polymer dots can be adjusted as desired in order to tune a variety of photophysical properties (e.g., absorbance, emission brightness, and/or the wavelength of maximum emission). Notably, in some cases, quenching of fluorescence is not increased due to particle formation. It will be appreciated that polymer dots having high brightness and specific binding capabilities provide important attributes to advance imaging and detection techniques for studying chemical and biological analytes and systems. In some embodiments, the organic-inorganic hybrid polymer dots disclosed herein can have a quantum yield of at least 1%. In some embodiments, the organic-inorganic hybrid polymer dots disclosed herein can have a quantum yield at least 5%. In some embodiments, the quantum yield is more than 5%, more than 10%, more than 20%, more than 30%, more than 40%, more than 50%, more than 60%, more than 70%, more than 80%, or more than 90%.

Organic-Inorganic Hybrid Polymer Dots with a Siloxane Network

In some embodiments, the hybrid polymer dots described herein include a siloxane network, e.g., a network including a plurality of Si—O—Si linkages. A siloxane network can be formed by the full or partial hydrolysis of one or more silane and/or siloxane species. For example, in certain embodiments, a siloxane network is fully or partially hydrolyzed from an alkyl silane, an alkoxy silane, a chloro silane, an orthosilicate, a siloxane, an alpha silane, an acetoxy silane, an amino silane, a bis silane, an epoxy silane, a halo silane, a hydrogen silane, a hydrogen siloxane, a hydroxyl silane, an ester silane, an aryl silane, an acryl silane, a methacryl silane, a styryl silane, a vinyl silane, an olefin silane, a sulfur silane, a phosphine silane, a phosphate silane, an isocyanate silane, an azide silane, an anhydride silane, or a combination thereof. In certain embodiments, the siloxane network is fully or partially hydrolyzed from octodecyltrimethoxysilane, octodecyltrichlorosilane, tetraethylorthosilicate, trifluoropropyltrimethoxysilane, phenyltrimethoxysilane, chloropropyltrimethoxysilane, heptadecafluorodecyltrichlorosilane, glycidoxypropyltrimethoxysilane, epoxyhexyltriethoxysilane, hydroxymethyltriethoxysilane, iodopropyltrimethoxysilane, isocyantopropyltrimethoxysilane, methacryloxymethyltriethoxysilane, vinyltrimethoxysilane, styrylethyltrimethoxysilane, or a combination thereof. In certain embodiments, the siloxane network is fully or partially hydrolyzed from octodecyltrimethoxysilane, octodecyltrichlorosilane, or tetraethylorthosilicate, or a combination thereof.

The weight percent of the siloxane network and/or the components thereof (e.g., silicon) in a hybrid polymer dot can be varied as desired. In some embodiments, the weight percent of the siloxane network and/or the components thereof (e.g., silicon) is selected to avoid formation of a core-shell structure in the resulting hybrid polymer dot. In certain embodiments, the weight percent of silicon from the siloxane network in the hybrid polymer dot is less than or equal to about 1%, less than or equal to about 5%, less than or equal to about 10%, less than or equal to about 15%, less than or equal to about 20%, less than or equal to about 25%, less than or equal to about 30%, less than or equal to about 35%, less than or equal to about 40%, less than or equal to about 45%, or less than or equal to about 47%. In certain embodiments, the weight percent of silicon from the siloxane network in the hybrid polymer dot is greater than or equal to about 1%, greater than or equal to about 5%, greater than or equal to about 10%, greater than or equal to about 15%, greater than or equal to about 20%, greater than or equal to about 25%, greater than or equal to about 30%, greater than or equal to about 35%, greater than or equal to about 40%, or greater than or equal to about 45%. In certain embodiments, the weight percent of silicon from the siloxane network in the hybrid polymer dot is within a range from about 1% to about 45%, or within a range from about 1% to about 47%.

Organic-inorganic hybrid polymer dots can comprise at least two silane species, each having their own respective function. For example, the organic-inorganic hybrid polymer dots can have a surface that is functionalized with a functional silane species comprising a carboxyl, an amine, a thiol (—SH), a carboxylate or carboxylic acid, a maleimide, a maleic anhydride, a N-hydroxysuccinimide (NHS), an alcohol (—OH), or a cyanate, or a combination thereof that is suitable for bioconjugation. Additionally, hybrid polymer dots can comprise an aliphatic chain, for example, an alkyl chain. The aliphatic chain can take part in cross linking during formation of the interpenetrated network. The aliphatic chain can be physically associated with the organic network (e.g., chromophoric polymer) and/or the siloxane network during formation of the interpenetrated network.

The hybrid polymer dot can comprise a siloxane network and at least one other network to form the interpenetrated organic-inorganic network. For example, in some embodiments, the present disclosure provides organic-inorganic hybrid polymer dots comprising a semiconducting chromophoric polymer and a siloxane network, wherein the semiconducting chromophoric polymer and the siloxane network form an organic-inorganic interpenetrated network. The interpenetrated network can be a mesh-like and/or interlocking structure of the siloxane network interpenetrated with the chromophoric polymer (e.g., without forming a core-cap or a core-shell structure).

An organic-inorganic hybrid polymer dot with a siloxane network can be formed in various ways. In certain embodiments, the hybrid polymer dot is formed through the physical association of the siloxane network with the chromophoric polymer so as to form an interpenetrated network. In certain embodiments, the hybrid polymer dot is formed wherein the siloxane network comprises an alkyl chain and wherein the semiconducting chromophoric polymer is physically associated with an alkyl chain of the siloxane network, thereby forming the organic-inorganic interpenetrated network. Alternatively or in combination, the siloxane network and chromophoric polymer can be chemically bonded (e.g., covalently bonded) to each other to form the interpenetrated network.

Hybrid Polymer Dots with Physical Association Between a Siloxane Network and a Semiconducting Chromophoric Polymer In some embodiments, the present disclosure provides hybrid polymer dots in which the siloxane network is physically associated with the semiconducting chromophoric polymer, such as by hydrophobic interaction. For example, the siloxane network can comprise an aliphatic chain and the semiconducting chromophoric polymer can be physically associated with the aliphatic chain of the siloxane network, thereby forming the organic-inorganic interpenetrated network. The aliphatic chain can comprise at least 5, at least 10, at least 15, or at least 20 carbons. The aliphatic chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the aliphatic side chain comprises at least 10 carbons. In some embodiments, the aliphatic chain is an alkyl chain. The alkyl chain can comprise at least 5, at least 10, at least 15, or at least 20 carbons. The alkyl chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the alkyl chain comprises at least 10 carbons. In some embodiments, the siloxane network comprises an alkylene, alkoxy, alkenyl, alkenylene, alkynyl, alkynylene, alkyl amine, cycloalkyl, cycloalkylene, heterocycloalkyl, or heterocycloalkylene.

In some embodiments, the siloxane network includes one or more orthogonally cross-linked units. In certain embodiments, an orthogonally cross-linked unit includes a reactive group that cross-links only with its designated reactive group, but not with another reactive group that may also be present. For example, reactive groups A and B can form a designated pair that cross-link with each other, and reactive groups Y and Z can form another designated pair that cross-link with each other. In such embodiments, reactive group A is considered to be orthogonal with respect to Y because A does not cross-link with Z, and reactive group Y is orthogonal with respect to A because Y does not cross-link with B. In some embodiments, reactive groups A can cross-link with each other or with reactive groups B to form a siloxane network, and reactive groups Y do not cross-link with either A or B, such that A and Y, and/or B and Y, are considered to be orthogonal cross-linking units.

In some embodiments, the siloxane network can comprise a plurality of interconnected units, and each interconnected unit can be selected from the group consisting of:

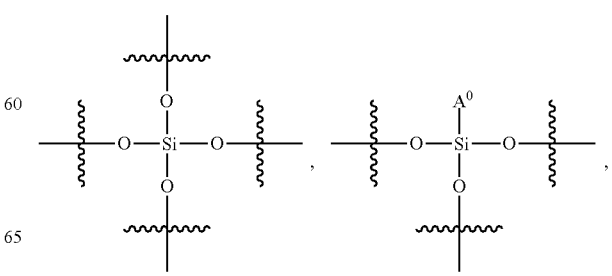

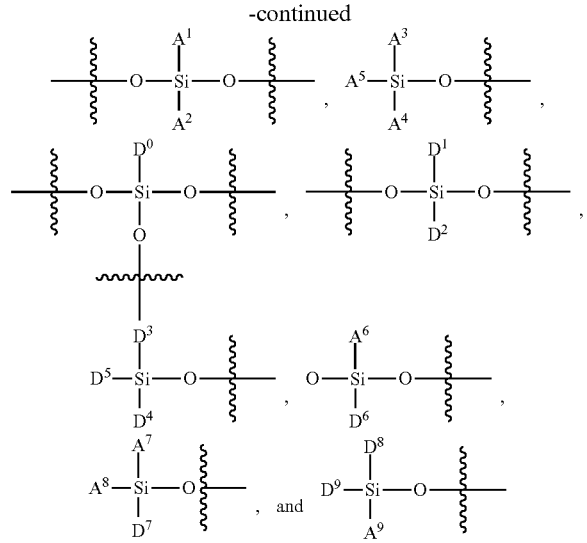

wherein: $A^0$, $A^1$, $A^2$, $A^3$, $A^4$, $A^5$, $A^6$, $A^7$, $A^8$, $A^9$ are each independently $C_nH_{2n+1}$, $C_nH_{2n}X$, $C_nF_{2n+1}$, or $C_nF_{2n}X$; wherein X is a functional group suitable for bioconjugation; wherein $D^0$, $D^1$, $D^2$, $D^3$, $D^4$, $D^5$, $D^6$, $D^7$, $D^8$, $D^9$ are each independently LX, wherein L is a linker moiety; and n is not less than 1. In some embodiments, n is not less than 2, not less than 3, not less than 4, not less than 5, not less than 6, not less than 7, not less than 8, not less than 9, or not less than 10. In some embodiments, n is not less than 6. In some embodiments, n is not greater than 20. In some embodiments, n is not greater than 40. In some embodiments, n is not greater than 60. In some embodiments, n is not less than 6 and is not greater than 20. In some embodiments, n is not less than 6 and is not greater than 15. In some embodiments, n is not less than 6 and is not greater than 10. Functional groups suitable for bioconjugation, also represented by "X," linker moieties, also represented by "L," and the combination thereof, also represented by "D" and "LX," are described in further detail herein below.

In some embodiments, the chromophoric polymer is physically associated with but not covalently bonded to the siloxane network. For example, in various embodiments, the chromophoric polymer is not silane functionalized, and functionalization and formation of the interpenetrated network of the hybrid polymer dot is achieved by the physical association (e.g., hydrophobic interaction) of the chromophoric polymer with the siloxane network only. In alternative embodiments, the chromophoric polymer can also be covalently bonded with the siloxane network, as discussed in greater detail below herein.

Hybrid Polymer Dots with Covalent Bonding Between a Siloxane Network a Semiconducting Chromophoric Polymer In some embodiments, the present disclosure provides hybrid polymer dots in which the siloxane network is covalently bonded with the semiconducting chromophoric polymer. For example, a hybrid polymer dot can comprise a semiconducting chromophoric polymer and a siloxane network that is covalently bonded to the semiconducting chromophoric polymer. Optionally, the hybrid polymer dot can also include a functional group (X) suitable for bioconjugation. In certain embodiments, the siloxane network is also physically associated with the chromophoric polymer in order to form an organic-inorganic interpenetrated network.

In some embodiments, the chromophoric polymer is silane functionalized. Functionalization of the hybrid polymer dot and formation of the interpenetrated network can be achieved by the presence of at least two silane species on the chromophoric polymer, each having its own respective function. The at least two silane species can be present as pendant side chains on the chromophoric polymer. The pendant side chains on the chromophoric polymer can include a silane chain ("$R^S$") and a functional silane chain including one or more functional groups ("$R^F$"), as shown below. One of the at least two silane species (e.g., the silane chain or functional silane chain) can comprise an aliphatic chain. The aliphatic chain can comprise at least 5, at least 10, at least 15, or at least 20 carbons. The aliphatic chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the aliphatic side chain comprises at least 10 carbons. In some embodiments, the aliphatic chain is an alkyl chain. The alkyl chain can comprise at least 5, at least 10, at least 15, or at least 20 carbons. The alkyl chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the alkyl chain comprises at least 10 carbons. In some embodiments, the siloxane network comprises an alkylene, alkoxy, alkenyl, alkenylene, alkynyl, alkynylene, alkyl amine, cycloalkyl, cycloalkylene, heterocycloalkyl, heterocycloalkylene. The alkyl chain can take part in cross linking during formation of the interpenetrated network. The alkyl chain can be chemically associated with the chromophoric polymer and/or the siloxane network during formation of the interpenetrated network. Additionally, the chromophoric polymer can comprise a functional silane species comprising a carboxyl, an amine, a thiol (—SH), a carboxylate or carboxylic acid, a maleimide, a maleic anhydride, a N-hydroxysuccinimide (NHS), an alcohol (—OH), or a cyanate, or a combination thereof that is suitable for bioconjugation. In some embodiments, the chromophoric polymer can comprise a carboxyl. In some embodiments, the hybrid polymer dots have a surface that is functionalized with the functional silane species that is suitable for bioconjugation.

FIG. 12 provides a general schematic illustration of conjugated polymers with a silane chain and functional silane chain for bioconjugation. In some embodiments, a semiconducting chromophoric polymer can comprise a plurality of units, M, which can be selected from:

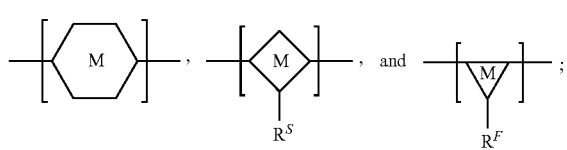

wherein:
$R^S$ is

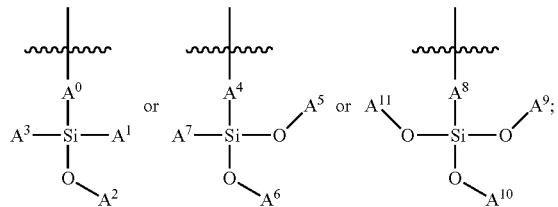

$R^F$ is

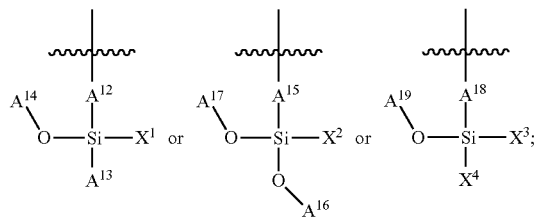

$A^0$, $A^4$, $A^8$, $A^{12}$, $A^5$, $A^{18}$, are each independently $C_nH_{2n}$ or $C_nF_{2n}$; $A^1$, $A^2$, $A^3$, $A^5$, $A^6$, $A^7$, $A^9$, $A^{10}$, $A^{11}$, $A^{13}$, $A^{14}$, $A^{16}$, $A^{17}$, $A^{19}$ are each independently $C_mH_{2m+1}$ or $C_mF_{2m+1}$, $C_mF_{2m}$; $X^1$, $X^2$, $X^3$, $X^4$ are each independently a functional group containing one or more active groups including but not limited to an amine, a carboxylate or carboxylic acid, a maleimide, a maleic anhydride, a thiol (—SH), a N-hydroxysuccinimide (NHS), or any of the other functional groups described herein; n is not less than 1; and m is not less than 1. In some embodiments, n is not less than 2, is not less than 3, is not less than 4, is not less than 5, is not less than 6, is not less than 7, is not less than 8, is not less than 9, or is not less than 10. In some embodiments, n is not less than 2. In some embodiments, n is not greater than 40. In some embodiments, n is not greater than 20. In some embodiments, n is not less than 1 and is not greater than 20. In some embodiments, n is not less than 2 and is not greater than 20. In some embodiments, m is not less than 2, not less than 3, not less than 4, not less than 5, not less than 6, not less than 7, not less than 8, not less than 9, or not less than 10. In some embodiments, m is not less than 3. In some embodiments, m is not less than 6. In some embodiments, m is not greater than 5, not greater than 6, not greater 7, not greater than 8, not greater than 9, or not greater than 10. In some embodiments, m is not greater than 20. In some embodiments, m is not greater than 40. In some embodiments, m is not greater than 60.

In some embodiments, the pendant side chains on the chromophoric polymer include a silane chain ("$R^S$") and a functional chain including one or more functional groups ("LX"), as shown below. The silane chain can comprise an aliphatic chain. The aliphatic chain can comprise at least 5, at least 10, at least 15, or at least 20 carbons. The aliphatic chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the aliphatic side chain comprises at least 10 carbons. In some embodiments, the aliphatic chain is an alkyl chain. The alkyl chain can comprise at least 5, at least 10, at least 15, or at least 20 carbons. The alkyl chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the alkyl chain comprises at least 10 carbons. In some embodiments, the siloxane network comprises an alkylene, alkoxy, alkenyl, alkenylene, alkynyl, alkynylene, alkyl amine, cycloalkyl, cycloalkylene, heterocycloalkyl, heterocycloalkylene. The alkyl chain can take part in cross linking during formation of the interpenetrated network. The alkyl chain can be chemically associated with the chromophoric polymer and/or the siloxane network during formation of the interpenetrated network. Additionally, the chromophoric polymer can comprise a functional chain including a functional group ("X") comprising a carboxyl, an amine, a thiol (—SH), a carboxylate or carboxylic acid, a maleimide, a maleic anhydride, a N-hydroxysuccinimide (NHS), an alcohol (—OH), or a cyanate, or a combination thereof that is suitable for bioconjugation. The functional group can be connected to the polymer backbone via a linker ("L"). In some embodiments, the chromophoric polymer can comprise a carboxyl. In some embodiments, the hybrid polymer dots have a surface that is functionalized with the functional species that is suitable for bioconjugation.

FIG. 13 provides a general schematic illustration of conjugated polymers with a silane chain and functional chain for bioconjugation. In some embodiments, a semiconducting chromophoric polymer can comprise a plurality of units, M, which can be selected from:

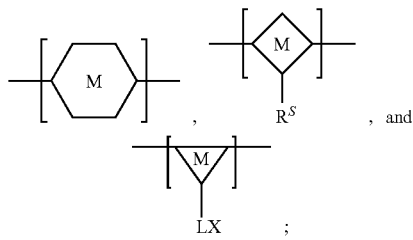

wherein:
$R^S$ is

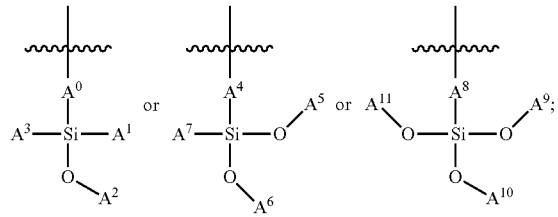

$A^0$, $A^4$, $A^8$, are each independently $C_nH_{2n}$ or $C_nF_{2n}$; $A^1$, $A^2$, $A^3$, $A^5$, $A^6$, $A^7$, $A^9$, $A^{10}$, $A^{11}$, are each independently $C_mH_{2m+1}$ or $C_mF_{2m+1}$, $C_mF_{2m}$; X is a functional group containing one or more active groups including but not limited to an amine, a carboxylate or carboxylic acid, a maleimide, a maleic anhydride, a thiol (—SH), a N-hydroxysuccinimide (NHS), or any of the other functional groups described herein; L is a linker between the polymer backbone and the functional group X; n is not less than 1; and m is not less than 1. In some embodiments, n is not less than 2, is not less than 3, is not less than 4, is not less than 5, is not less than 6, is not less than 7, is not less than 8, is not less than 9, or is not less than 10. In some embodiments, n is not less than 2. In some embodiments, n is not greater than 40. In some embodiments, n is not greater than 20. In some embodiments, n is not less than 1 and is not greater than 20. In some embodiments, m is not less than 2, not less than 3, not less than 4, not less than 5, not less than 6, not less than 7, not less than 8, not less than 9, or not less than 10. In some embodiments, n is not less than 2 and is not greater than 20. In some embodiments, m is not less than 3. In some embodiments, m is not less than 6. In some embodiments, m is not greater than 5, not greater than 6, not greater 7, not greater than 8, not greater than 9, or not greater than 10. In some embodiments, m is not greater than 20. In some embodiments, m is not greater than 40. In some embodiments, m is not greater than 60. In some embodiments, m is not less than 1 and is not greater than 20.

In some embodiments, the pendant side chains on the chromophoric polymer include a functional silane chain ("$R^F$") including one or more functional groups, as shown below. The functional silane chain can comprise an aliphatic chain. The aliphatic chain can comprise at least 5, at least 10, at least 15, or at least 20 carbons. The aliphatic chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the aliphatic side chain comprises at least 10 carbons. In some embodiments, the aliphatic chain is an alkyl chain. The alkyl chain can comprise at least 5, at least 10, at least 15, or at least 20 carbons. The alkyl chain can comprise, at least 5, at least 6, at least 7, at least 8, at least 9, at least 10, at least 11, at least 12, at least 13, at least 14, at least 15, at least 16, at least 17, at least 18, at least 19, or at least 20 carbons. In some embodiments, the alkyl chain comprises at least 10 carbons. In some embodiments, the siloxane network comprises an alkylene, alkoxy, alkenyl, alkenylene, alkynyl, alkynylene, alkyl amine, cycloalkyl, cycloalkylene, heterocycloalkyl, heterocycloalkylene. The alkyl chain can take part in cross linking during formation of the interpenetrated network. The alkyl chain can be chemically associated with the chromophoric polymer and/or the siloxane network during formation of the interpenetrated network. Additionally, the functional silane chain can include a functional group ("X") comprising a carboxyl, an amine, a thiol (—SH), a carboxylate or carboxylic acid, a maleimide, a maleic anhydride, a N-hydroxysuccinimide (NHS), an alcohol (—OH), or a cyanate, or a combination thereof that is suitable for bioconjugation. In some embodiments, the hybrid polymer dots have a surface that is functionalized with the functional species that is suitable for bioconjugation.

FIG. 14 provides a general schematic illustration of conjugated polymers with a silane chain and functional chain for bioconjugation. In some embodiments, a semiconducting chromophoric polymer can comprise a plurality of units, M, which can be selected from:

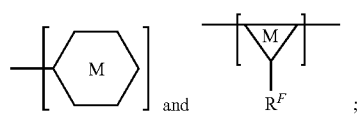

wherein:
$R^F$ is

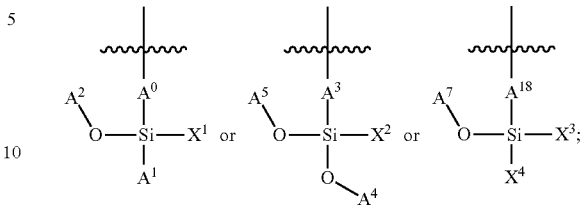

$A^0$, $A^3$, $A^6$ are each independently $CH_{2n}$ or $C_nF_{2n}$; $A^1$, $A^2$, $A^4$, $A^5$, $A^7$ are each independently $C_mH_{2m+1}$ or $C_mF_{2m+1}$; $X^1$, $X^2$, $X^3$, $X^4$ are each independently a functional group containing one or more active groups including but not limited to an amine, a carboxylate or carboxylic acid, a maleimide, a maleic anhydride, a thiol (—SH), a N-hydroxysuccinimide (NHS), or any of the other functional groups described herein; n is not less than 1; and m is not less than 1. In some embodiments, n is not less than 2, is not less than 3, is not less than 4, is not less than 5, is not less than 6, is not less than 7, is not less than 8, is not less than 9, or is not less than 10. In some embodiments, n is not less than 2. In some embodiments, n is not greater than 40. In some embodiments, n is not greater than 20. In some embodiments, n is not less than 1 and is not greater than 20. In some embodiments, n is not less than 2 and is not greater than 20. In some embodiments, m is not less than 2, not less than 3, not less than 4, not less than 5, not less than 6, not less than 7, not less than 8, not less than 9, or not less than 10. In some embodiments, m is not less than 3. In some embodiments, m is not less than 6. In some embodiments, m is not greater than 5, not greater than 6, not greater 7, not greater than 8, not greater than 9, or not greater than 10. In some embodiments, m is not greater than 20. In some embodiments, m is not greater than 40. In some embodiments, m is not greater than 60. In some embodiments, m is not less than 1 and is not greater than 20.

In some embodiments, the semiconducting chromophoric polymer can comprise a functional group suitable for bioconjugation (X) and an alkoxylsilyl or alkylsilyl.

In some embodiments, the siloxane network can comprise a plurality of interconnected units, wherein the plurality of interconnected units can comprise a unit selected from the group consisting of:

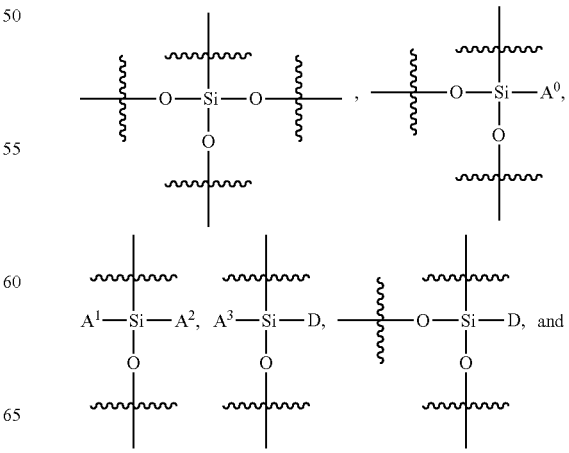

-continued

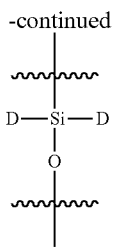

wherein: $A^0$, $A^1$, $A^2$, $A^3$ are each independently $C_pH_{2p+1}$, $C_pF_{2p+1}$, $C_pH_{2p}X$, or $C_pF_{2p}X$; D is LX, wherein L is a linker moiety; and p is not less than 1. In some embodiments, p is not less than 2, p is not less than 3, p is not less than 4, not less than 5, not less than 6, not less than 7, not less than 8, not less than 9, or not less than 10. In some embodiments, p is not less than 6. In some embodiments, p is not greater than 20. In some embodiments, p is not greater than 40. In some embodiments, p is not greater than 60. In some embodiments, p is not less than 6 and is not greater than 20. In some embodiments, p is not less than 6 and is not greater than 15. In some embodiments, p is not less than 6 and is not greater than 10.

In some embodiments, an organo-silane is used to form a hybrid polymer dot including a siloxane network, and the weight percent of the siloxane network and/or the components thereof (e.g., silicon) in the hybrid polymer dot can be varied as desired. In some embodiments, the weight percent of the siloxane network and/or the components thereof (e.g., silicon) is selected to avoid formation of a core-shell structure in the resulting hybrid polymer dot. In certain embodiments, the weight percent of silicon from the siloxane network in the hybrid polymer dot is less than or equal to about 1%, less than or equal to about 5%, less than or equal to about 10%, less than or equal to about 15%, less than or equal to about 20%, less than or equal to about 25%, less than or equal to about 30%, less than or equal to about 35%, less than or equal to about 40%, less than or equal to about 45%, or less than or equal to about 47%. In certain embodiments, the weight percent of silicon from the siloxane network in the hybrid polymer dot is greater than or equal to about 1%, greater than or equal to about 5%, greater than or equal to about 10%, greater than or equal to about 15%, greater than or equal to about 20%, greater than or equal to about 25%, greater than or equal to about 30%, greater than or equal to about 35%, greater than or equal to about 40%, or greater than or equal to about 45%. In certain embodiments, the weight percent of silicon from the siloxane network in the hybrid polymer dot is within a range from about 1% to about 45%, or within a range from about 1% to about 47%.

In some embodiments, the polymer dot can comprise at least two orthogonal reactive chemical groups. In some embodiments, one of the at least two orthogonal reactive chemical groups that the polymer dot comprises has the formula $C_nH_{2n}X$ or $C_nF_{2n}X$, wherein X is a functional group suitable for bioconjugation and n is not less than 1. In some embodiments, one of the at least two orthogonal reactive chemical groups of the polymer dot comprises X, where X is a functional group suitable for bioconjugation. The semiconducting chromophoric polymer can comprise at least two orthogonal reactive chemical groups. In some embodiments, one of the at least two orthogonal reactive chemical groups that the semiconducting chromophoric polymer comprises has the formula $C_nH_{2n}X$ or $C_nF_{2n}X$, wherein X is a functional group suitable for bioconjugation and n is not less than 1. In some embodiments, n is not less than 2, n is not less than 3, n is not less than 4, not less than 5, not less than 6, not less than 7, not less than 8, not less than 9, or not less than 10. In some embodiments, n is not less than 6. In some embodiments, n is not greater than 20. In some embodiments, n is not greater than 40. In some embodiments, n is not greater than 60. In some embodiments, n is not less than 6 and is not greater than 20. In some embodiments, n is not less than 6 and is not greater than 15. In some embodiments, n is not less than 6 and is not greater than 10.

Chromophoric Polymers for Use in Hybrid Polymer Dots

The hybrid polymer dots described herein can comprise various types of chromophoric polymers, such as one or more of the chromophoric polymer types described herein. Hybrid polymer dots can include one or more chromophoric polymers (e.g., semiconducting chromophoric polymers) that have been collapsed into a stable sub-micron sized particle.

In some embodiments, the hybrid polymer dots of the present disclosure comprise a plurality of polymers. In certain embodiments the polymer dot can comprise a plurality of semiconducting chromophoric polymers. In certain embodiments, the hybrid polymer dots can comprise a blend of chromophoric polymers and non-chromophoric polymers. In certain embodiments, the hybrid polymer dots can comprise a blend of semiconducting chromophoric polymers. In certain embodiments, the hybrid polymer dots include a blend of semiconducting chromophoric polymers. The blends can include any combination of homopolymers, copolymers, and oligomers. Polymer blends used to form hybrid polymer dots may be selected in order to tune the properties of the resulting polymer particles, for example, to achieve a desired excitation or emission spectra for the hybrid polymer dot.

The hybrid polymer dots can comprise polymers with one or more repeating units, which can be combined in fixed, ordered, or random configurations and ratios. A repeating unit can be a monomer or a chemical motif that occurs throughout the polymer, such as an aromatic or heterocyclic unit. The polymers can be halogenated, for example, fluorinated, chlorinated, brominated, or iodinated. A polymer, a repeating unit, or a monomer can be halogenated at one or multiple sites. A halogenated polymer, for example, a fluorinated polymer, can provide greater levels of fluorescence than can a non-halogenated analogous polymer.

Any suitable number and combination of chromophoric polymer types can be incorporated in the hybrid polymer dots described herein, such as one or more chromophoric polymers, two or more chromophoric polymers, three or more chromophoric polymers, four or more chromophoric polymers, five or more chromophoric polymers, six or more chromophoric polymers, seven or more chromophoric polymers, eight or more chromophoric polymers, nine or more chromophoric polymers, ten or more chromophoric polymers, fifty or more chromophoric polymers, or one hundred or more chromophoric polymers.

The chromophoric polymer can be a homopolymer or a heteropolymer. In various embodiments, the chromophoric polymer can be a semiconducting polymer, a non-semiconducting polymer, or a combination thereof. For example, a number of semiconducting polymers are suitable for use in hybrid polymer dots according to the present disclosure. Semiconducting polymers have been developed with emission wavelengths ranging from UV to infrared, including the entire visible spectrum. Examples of semiconducting polymers include but are not limited to: polyfluorene-based polymers, including but not limited to poly(9,9-dihexylfluorenyl-2,7-diyl) (PDHF)-based and poly(9,9-dioctylfluorenyl-2,7-diyl) (PFO)-based polymers; fluorene-based copolymers, including but not limited to, poly[{9,9-dioctyl-2,7-divinylene-fluorenylene}-alt-co-{2-methoxy-5-(2-ethylhexyloxy)-1,4-phenylene}] (PFPV)-based, poly[(9,9-dioctylfluorenyl-2,7-diyl)-co-(1,4-benzo-{2,1,3}-thiadiazole)] (PFBT)-based, poly[(9,9-dioctylfluorenyl-2,7-diyl)-co-(4,7-Di-2-thienyl-2,1,3-benzothiadiazole)] (PFTBT)-based, and poly[(9,9-dioctylfluorenyl-2,7-diyl)-co-(4,7-Di-2-thienyl-2,1,3-benzothiadiazole)](PF-0.1TBT)-based polymers; phenylene vinylene-based polymers, including but not limited to, poly[2-methoxy-5-(2-ethylhexyloxy)-1,4-phenylenevinylene] (MEH-PPV)-based and poly[2-methoxy-5-(2-ethylhexyloxy)-1,4-(1-cyanovinylene-1,4-phenylene)] (CN-PPV)-based polymers; phenylene ethynylene-based polymers, including but not limited to, poly(2,5-di(3',7'-dimethyloctyl)phenylene-1,4-ethynylene (PPE)-based polymers; or a combination thereof.

A wide variety of chromophoric polymer structures are suitable for use in accordance with various embodiments and embodiments of the present disclosure. In some embodiments, the chromophoric polymer is a linear polymer. In other embodiments, the chromophoric polymer is a branched polymer. In certain embodiments, the chromophoric polymer is a dendrimer. In certain embodiments, the chromophoric polymer is a brush polymer. In certain embodiments, the chromophoric polymer is a star polymer.

In some embodiments, the chromophoric polymers contain a polymer functionalized on the terminal monomeric unit, for example with a carboxyl, amine, thiol, ester, succinimidyl ester, azide, alkyne, cyclooctyne, phosphine, or similar functional group. Examples of such polymers include but are not limited to poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some embodiments of the present disclosure, the hybrid polymer dots provided herein include the polymer CN-PPV, also known as poly[2-methoxy-5-(2-ethylhexyloxy)-1,4-(1-cyanovinylene-1,4-phenylene)], which is a bright, compact, and orange-light-emitting semiconducting polymer particle. In certain embodiments, CN-PPV has superior fluorescence properties, such as a large absorption cross-section, high quantum yield, and a fast emission rate. In some embodiments, the hybrid polymer dot comprises a polymer that consists essentially of CN-PPV. In some embodiments, the particle includes CN-PPV and at least one other material. For example, the CN-PPV can form part of a copolymer or be mixed with a copolymer or other material that provides an additional functionality.

In some embodiments, the hybrid polymer dots of the present disclosure include a semiconducting copolymer having at least two different chromophoric units. For example, a conjugated or semiconducting copolymer can contain both fluorene and benzothiazole chromophoric units present at a given ratio. Typical chromophoric units used to synthesize semiconducting copolymers include, but are not limited to fluorene units, phenylene vinylene units, phenylene units, phenylene ethynylene units, benzothiazole units, thiophene units, carbazole fluorene units, boron-dipyrromethene units, squaraine units, and derivatives thereof. The different chromophoric units can be segregated, as in a block copolymer, or intermingled. In some embodiments, a chromophoric copolymer is represented by writing the identity of the major chromophoric species. For example, PFBT is a chromophoric polymer containing fluorene and benzothiazole units at a certain ratio. In some embodiments, a dash is used to indicate the percentage of the minor chromophoric species and then the identity of the minor chromophoric species. For example, PF-0.1 BT is a chromophoric copolymer containing 90% PF and 10% BT.

In some embodiments, the hybrid polymer dots of the present disclosure include polymers that have a narrow band emissive unit (e.g., a narrow band monomer and/or a narrow band unit). For example, the present disclosure can include a homopolymer or heteropolymer including a narrow band monomer, such as BODIPY and/or BODIPY derivative monomer, a squaraine and/or squaraine derivative monomer, a metal complex and/or metal complex derivative monomer, a porphyrin and/or porphyrin derivative monomer, a metalloporphyrin and/or metalloporphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. In certain embodiments, a narrow band unit is, e.g., a narrow band monomer or a fluorescent nanoparticle embedded in or attached to the polymer dot.

In some embodiments, the hybrid polymer dots can comprise a fluorene polymer, a fluorene-based polymer or copolymer, a phenylene vinylene-based polymer or copolymer, a phenylene ethynylene-based polymer or copolymer, and a BODIPY-based polymer or copolymer. In some embodiments, the hybrid polymer dots can comprise poly(9,9-dihexylfluorenyl-2,7-diyl) (PDHF), Poly(9,9-dioctylfluorenyl-2,7-diyl) (PFO), poly[{9,9-dioctyl-2,7-divinylenefluorenylene}-alt-co-{2-methoxy-5-(2-ethylhexyloxy)-1,4-phenylene}](PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), BODIPY 570, BODIPY 590, or BODIPY 690.

In some embodiments, the hybrid polymer dots can comprise a BODIPY derivative. The BODIPY derivative can have the structure of Formula (I):

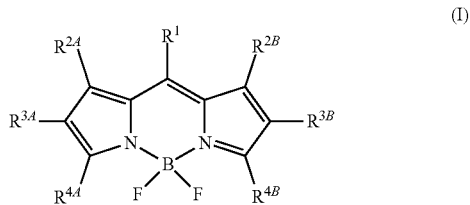

(I)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof.

In some embodiments, the hybrid polymer dots of the present disclosure include a polymer that includes a narrow-band monomer having the structure of Formula (II):

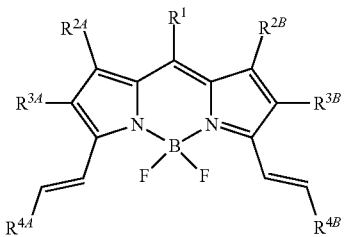

(II)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof. The monomer can, for example, integrate with the backbone of the polymer by attachment to the $R^{3A}$ and $R^{3B}$ groups.

In some embodiments, the hybrid polymer dots of the present disclosure include a polymer that includes a narrow-band monomer having the structure of Formula (III):

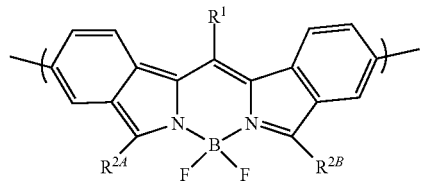

(III)

wherein each of $R^1$, $R^{2A}$ and $R^{2B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment, e.g., to $R^1$, $R^{2A}$, $R^{2B}$, or a combination thereof. The parentheses indicate points of attachment of the monomer to the backbone of the polymer.

In some embodiments, the hybrid polymer dots of the present disclosure include a polymer that includes a narrow-band monomer having the structure of Formula (IV):

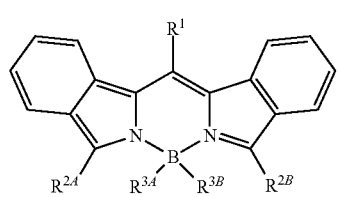

(IV)

wherein each of $R^1$, $R^{2A}$, $R^{2B}$, $R^{3A}$, and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, and $R^{3B}$ or a combination thereof.

In some embodiments, the hybrid polymer dots of the present disclosure include a polymer that includes a narrow-band monomer having the structure of Formula (V):

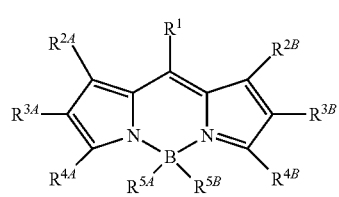

(V)

wherein each of $R^1$, $R^{2A}$, $R^{2B}$, $R^{3A}$, $R^{3B}$, $R^{4A}$, $R^{4B}$, $R^{5A}$, and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof. In certain embodiments, the narrow-band monomers can be integrated into the backbone by attachment to the $R^{5A}$ and $R^{5B}$ groups.

In some embodiments, the hybrid polymer dots of the present disclosure include a polymer that includes a narrow-band monomer having the structure of Formula (VI):

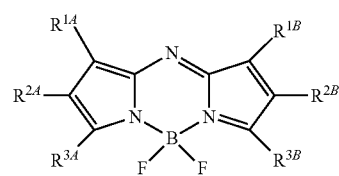

(VI)

wherein each of $R^{1A}$, $R^{1B}$, $R^{2A}$, $R^{2B}$, $R^{3A}$ and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^{1A}$, $R^{1B}$, $R^{2A}$, $R^{2B}$, $R^{3A}$, $R^{3B}$, or a combination thereof.

In some embodiments, the hybrid polymer dots of the present disclosure include a polymer that includes a narrow-band monomer having the structure of Formula (VII):

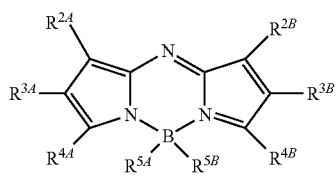

(VII)

wherein each of $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl The narrow-band monomer can be integrated into a backbone of the polymer (e.g., polymerized in the polymer) and/or covalently attached to the backbone, a terminus, or a sidechain of the polymer) through at least one attachment to $R^{2A}$, $R^{2B}$, $R^{3A}$, $R^{3B}$, $R^{4A}$, $R^{4B}$, $R^{5A}$, $R^{5B}$, or a combination thereof.

In some embodiments, the hybrid polymer dots of the present disclosure include a polymer that includes a narrow-band monomer having the structure of Formula (VIII):

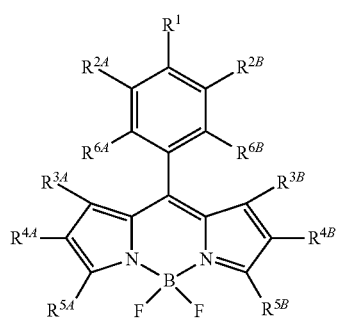

(VIII)

wherein each of $R^1$, $R^{2A}$, $R^{2B}$, $R^{3A}$, $R^{3B}$, $R^{4A}$ and $R^{4B}$, is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl, and wherein each of $R^{5A}$, $R^{5B}$, $R^{6A}$ and $R^{6B}$ are independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer) through at least one attachment to $R^1$, $R^{2A}$, $R^{2B}$, $R^{3A}$, $R^{3B}$, $R^{4A}$, $R^{4B}R^{5A}$, $R^{5B}$, $R^{6A}$, $R^{6B}$ or a combination thereof.

In some embodiments, the hybrid polymer dots of the present disclosure include a polymer that includes a narrow-band monomer having the structure of Formula (IX):

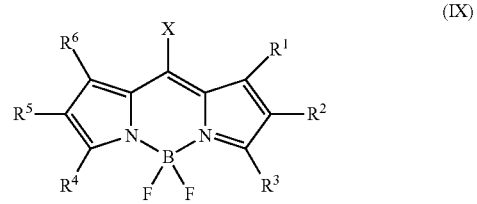

(IX)

wherein X has the structure of any one of Formulae (X), (XI), (XII), and (XIII) or their derivatives:

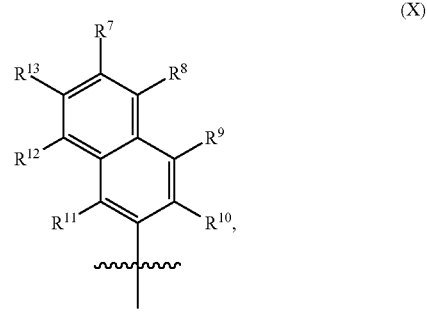

(X)

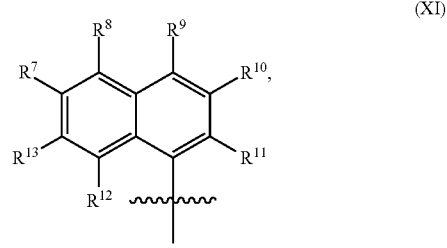

(XI)

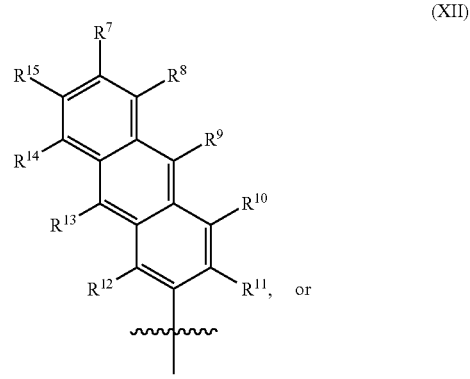

(XII)

or

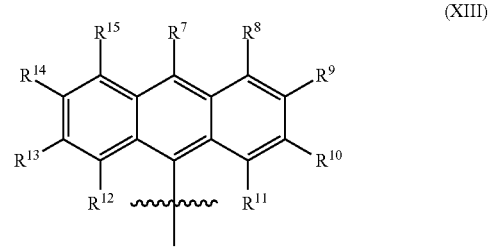

(XIII)

and wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in Formulae (X), (XI), (XII), and (XIII) is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. When X represents naphthalene and its derivatives, the narrow-band monomer can be integrated into a backbone (e.g., polymerized in the polymer) and/or covalently attached to the backbone, a terminus, or a sidechain of the polymer) of the polymer through at least one attachment to $R^7$, $R^8$, $R^9$, $R^{10}$, $R^{11}$, $R^{12}$, $R^{13}$ or a combination thereof. When X represents anthracene and its derivatives, the narrow-band monomer can be integrated into a backbone of the polymer and/or covalently attached to the backbone, a terminus, or a sidechain of the polymer through at least one attachment to $R^7$, $R^8$, $R^9$, $R^{10}$, $R^{11}$, $R^{12}$, $R^{13}$, $R^{14}$, $R^{15}$ or a combination thereof.

Narrow band monomers of the present disclosure can further include dipyrrin derivatives. Dipyrrin and dipyrrin derivatives can be polymerized to form polymers (e.g., homopolymers or heteropolymers) and/or can be attached (e.g., covalently attached) to a polymer backbone, sidechain and/or terminus. For example, the hybrid polymer dots of the present disclosure can include a polymer that includes a narrow-band monomer having the structure of Formula (XIV):

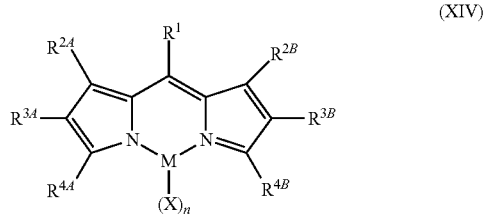

(XIV)

wherein M is a metal. Examples of M can be, but is not limited to, Na, Li, Zn, Co, or Si. X can include substituents such as, but not limited to, halogen, alkyl, phenyl, alkylphenyl, thiophenyl, alkylthiophenyl, alkoxyl, alkoxylphenyl, alkylthiophenyl, ester, or hydroxyl. The number of X groups (n) can be 1 or more than 1, and n can be 0, 1, 2, 3, 4. Each of $R^1$, $R^{2A}$, $R^{2B}$, $R^{3A}$, $R^{3B}$, $R^{4A}$, and $R^{4B}$ can be independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., methoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer) through at least one attachment to $R^1$, $R^{2A}$, $R^{2B}$, $R^{3A}$, $R^{3B}$, $R^{4A}$, $R^{4B}$, or a combination thereof.

In some embodiments, the narrow-band emissive polymers for making hybrid polymer dots include squaraine and squaraine derivatives as narrow-band monomers. Squaraine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The squaraine and their derivatives can be energy acceptors and other monomers can be energy donors so that the final hybrid polymer dots can exhibit narrow-band emissions. The narrow-band emissive chromophoric polymers in good solvents may exhibit broad emissions or narrow emissions. However, in some embodiments, their nanoparticle form gives narrow-band emissions. In some embodiments, the emission full width at half maximum (FWHM) of the above hybrid polymer dots is less than 70 nm. In certain embodiments, the FWHM is less than 60 nm, less than 50 nm, less than 40 nm, less than 30 nm, or less than 20 nm.

Suitable squaraine derivatives for use in the present disclosure can include the following structures described below. Squaraine and squaraine derivatives can be polymerized to form polymers (e.g., homopolymers or heteropolymers) and/or can be attached (e.g., covalently attached) to a polymer backbone, sidechain and/or terminus. Hybrid polymer dots of the present disclosure can include a polymer that includes a narrow-band monomer having the structure of Formula (XV):

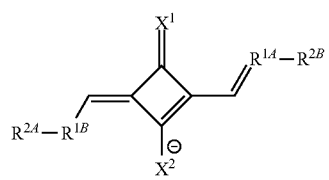

(XV)

wherein each of $X^1$ and $X^2$ is independently selected from the group consisting of oxygen, sulfur and nitrogen; each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. Other reactive groups can be used. In some embodiments, the halide is a chloro, a bromo, or an iodo group. The reactive group can be used to integrate the monomer into a polymer, e.g., along the backbone of the polymer (e.g., by polymerizing in the polymer) and/or to attach the monomer by covalent attachment to the backbone, a terminus, or a sidechain of the polymer. The narrow-band monomer can be integrated into a backbone of the polymer (e.g., polymerized in the polymer) and/or covalently attached to the backbone, a terminus, or a sidechain of the polymer) through at least one attachment to $R^{1A}$, $R^{1B}$, $R^{2A}$, $R^{2B}$, or a combination thereof.

The present disclosure can include oxygen-containing squaraine derivatives. Hybrid polymer dots of the present disclosure can include a polymer that includes a narrow-band monomer having the structure of Formula (XVI):

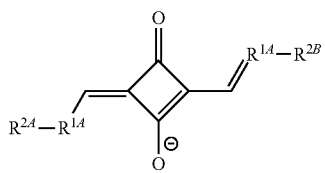

(XVI)

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. Other reactive groups can be used. In some embodiments, the halide is a chloro, a bromo, or an iodo group. The reactive group can be used to integrate the monomer into a polymer (e.g., along the backbone of the polymer by polymerizing in the polymer) and/or to attach the monomer by covalent attachment to the backbone, a terminus, or a sidechain of the polymer.

Hybrid polymer dots of the present disclosure can include a polymer that includes a narrow-band monomer having the structure of Formula (XVII):

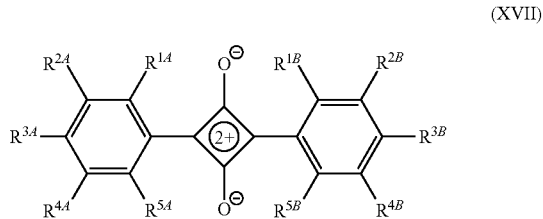

(XVII)

wherein each of $R^{1A}$ and $R^{1B}$ is independently selected from the group consisting of, but not limited to, hydrogen, methyl, alkyl, phenyl, araalkyl, and alkoxy-phenyl; each of $R^{2A}$ and $R^{2B}$ is independently selected from the group consisting of, but not limited to, hydrogen, methyl, alkyl, phenyl, araalkyl, and alkoxy-phenyl; each of $R^{3A}$ and $R^{3B}$ is a reactive group independently selected from the group consisting of, but not limited to, chloro, bromo, iodo, and hydroxyl; each of $R^{4A}$ and $R^{4B}$ is independently is selected from a group consisting of, but not limited to, hydroxyl, hydrogen, alkyl, phenyl, araalkyl, and alkoxy-phenyl; and each of $R^{5A}$ and $R^{5B}$ is independently selected from the group consisting of, but not limited to, hydrogen, methyl, alkyl, phenyl, araalkyl, and alkoxy-phenyl. Other reactive groups can be used. The reactive group can be used to integrate the monomer into a polymer (e.g., along the backbone of the polymer by polymerizing in the polymer) and/or to attach the monomer by covalent attachment to the backbone, a terminus, or a sidechain of the polymer.

Hybrid polymer dots of the present disclosure can include a polymer that includes a narrow-band monomer having the structure of Formula (XVIII):

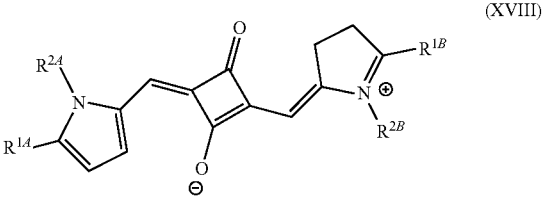

(XVIII)

wherein each of $R^{1A}$ and $R^{1B}$ is a reactive group independently selected from the group consisting of, but not limited to, chloro, bromo, iodo, and hydroxyl; and each of $R^{2A}$ and $R^{2B}$ is selected from the group consisting of, but not limited to, hydrogen, methyl, alkyl, phenyl, araalkyl, and alkoxy-phenyl. Other reactive groups can be used. The reactive group can be used to integrate the monomer into a polymer (e.g., along the backbone of the polymer by polymerizing in the polymer) and/or attach the monomer by covalent attachment to the backbone, a terminus, or a sidechain of the polymer.

Hybrid polymer dots of the present disclosure can include a polymer that includes a narrow-band monomer having the structure of Formula (XIX):

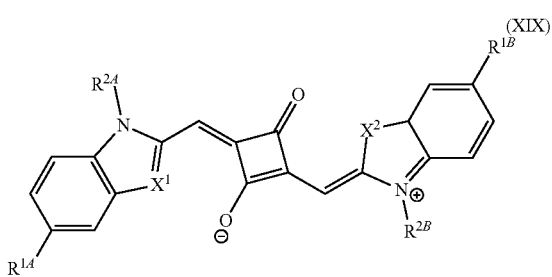

(XIX)

wherein each of $X^1$ and $X^2$ is independently selected from the group consisting of carbon, sulfur, nitrogen, and selenium; each of $R^{1A}$ and $R^{1B}$ is a reactive group independently selected from the group consisting of, but not limited to, chloro, bromo, iodo, and hydroxyl; and each of $R^{2A}$ and $R^{2B}$ is independently selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. The reactive group can be used to integrate the monomer into a polymer (e.g., along the backbone of the polymer by polymerizing in the polymer) and/or attach the monomer by covalent attachment to the backbone, a terminus, or a sidechain of the polymer.

Hybrid polymer dots of the present disclosure can include a polymer that includes a narrow-band monomer having the structure of Formula (XX):

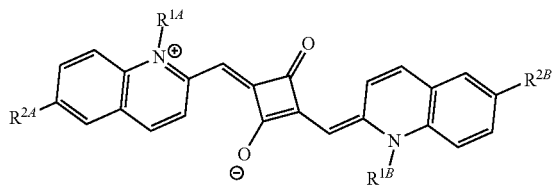

(XX)

wherein each of $R^{2A}$ and $R^{2B}$ is a reactive group independently selected from the group consisting of, but not limited to, chloro, bromo, iodo, and hydroxyl; and each of $R^{1A}$ and $R^{1B}$ is selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. The reactive group can be used to integrate the monomer into a polymer (e.g., along the backbone of the polymer by polymerizing in the polymer) and/or attach the monomer by covalent attachment to the backbone, a terminus, or a sidechain of the polymer.

The present disclosure can include sulfur-containing squaraine derivatives. Hybrid polymer dots of the present disclosure can include a polymer that includes a narrow-band monomer having the structure of Formula (XXI):

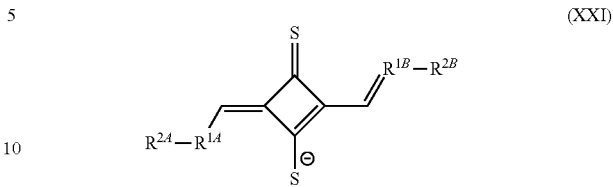

(XXI)

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. In some embodiments, the halide is a chloro, a bromo, or an iodo group. Other reactive groups can be used. The reactive group can be used to integrate the monomer into a polymer (e.g., along the backbone of the polymer by polymerizing in the polymer) and/or attach the monomer by covalent attachment to the backbone, a terminus, or a sidechain of the polymer.

Hybrid polymer dots of the present disclosure can include a polymer that includes a narrow-band monomer having the structure of Formula (XXII):

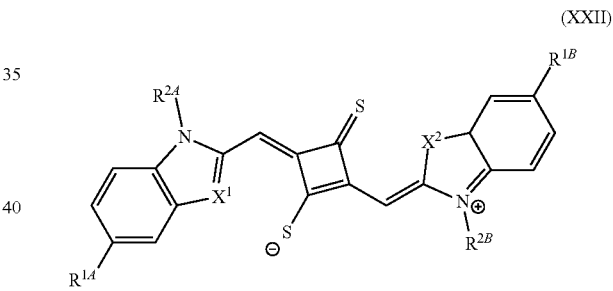

(XXII)

wherein each of $X^1$ and $X^2$ is independently selected from the group consisting of carbon, sulfur, nitrogen, and selenium; each of $R^{1A}$ and $R^{1B}$ is a reactive group independently selected from the group consisting of, but not limited to, chloro, bromo, iodo, and hydroxyl; and each of $R^{2A}$ and $R^{2B}$ is independently selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. In some embodiments, the halide is a chloro, a bromo, or an iodo group. The reactive group can be used to integrate the monomer into a polymer (e.g., along the backbone of the polymer by polymerizing in the polymer) and/or attach the monomer by covalent attachment to the backbone, a terminus, or a sidechain of the polymer.

The present disclosure can include nitrogen-containing squaraine derivatives. Hybrid polymer dots of the present disclosure can include a polymer that includes a narrow-band monomer having the structure of Formula (XXIII):

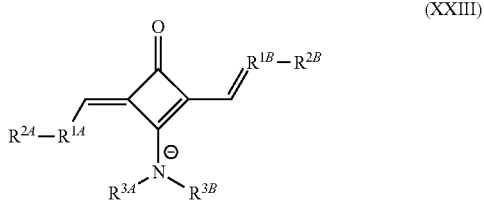

(XXIII)

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; each of $R^{2A}$ and $R^{2B}$ is a reactive group independently selected from the group consisting of, but not limited to, a halide, hydroxyl, and amino; and each of $R^{3A}$ and $R^{3B}$ is independently selected from the group consisting of hydrogen, methyl, alkyl, phenyl, aralkyl, and alkoxy-phenyl. Other reactive groups can be used. In some embodiments, the halide is a chloro, a bromo, or an iodo group. The reactive group can be used to integrate the monomer along into a polymer (e.g., along the backbone of the polymer by polymerizing in the polymer) and/or attach the monomer by covalent attachment to the backbone, a terminus, or a sidechain of the polymer.

Hybrid polymer dots of the present disclosure can include a polymer that includes a narrow-band monomer having the structure of Formula (XXIV):

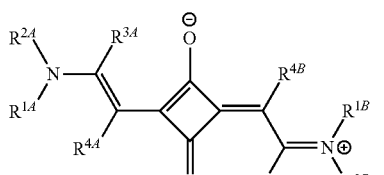

(XXIV)

wherein each of $R^{1A}$, $R^{1B}$, $R^{2A}$ and $R^{2B}$ are independently selected from the group consisting of, but not limited to, hydrogen, deuterium, alkyl, aryl, acetyl, and hydroxyl; and each of $R^{3A}$, $R^{3B}$ $R^{4A}$ and $R^{4B}$ are independently selected from the group consisting of, but not limited to, hydrogen, deuterium, alkyl, aryl, amino, sulfide, aldehyde, ester, ether, carboxyl, hydroxyl, and halide. The narrow-band monomer can be integrated into a backbone of the polymer (e.g., along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$ or a combination thereof.

Hybrid polymer dots of the present disclosure can include a polymer that includes a narrow-band monomer having the structure of Formula (XXV):

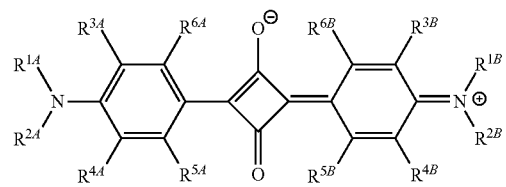

(XXV)

wherein each of $R^{1A}$, $R^{1B}$, $R^{2A}$ and $R^{2B}$ are independently selected from the group consisting of, but not limited to, hydrogen, deuterium, alkyl, aryl, acetyl, and hydroxyl; and each of $R^{3A}$, $R^{3B}$, $R^{4A}$, $R^{4B}$, $R^{5A}$, $R^{5B}$, $R^{6A}$ and $R^{6B}$ are independently selected from the group consisting of, but not limited to, hydrogen, deuterium, alkyl, aryl, amino, sulfide, aldehyde, ester, ether, carboxyl, hydroxyl, and halide. The narrow-band monomer can be integrated into a backbone of the polymer (e.g., along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof.

Hybrid polymer dots of the present disclosure can include a polymer that includes a narrow-band monomer having the structure of Formula (XXVI):

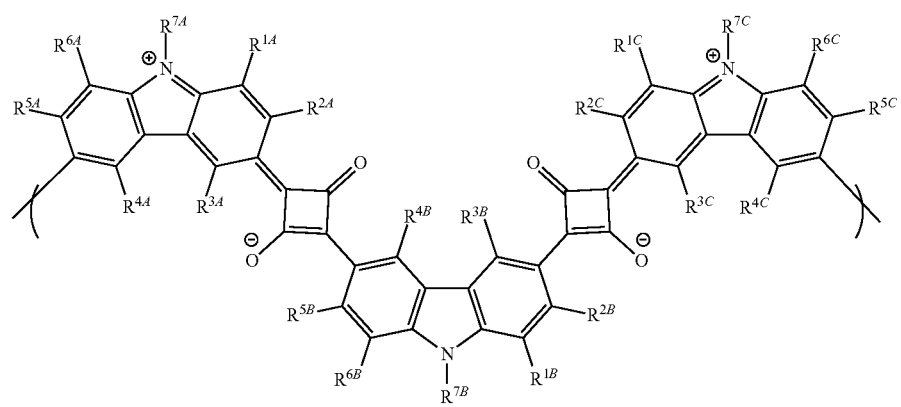

(XXVI)

wherein each of $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, and $R^{6C}$ are independently selected from the group consisting of, but not limited to, hydrogen, deuterium, alkyl, aryl, amino, sulfide, aldehyde, ester, ether, carboxyl, hydroxyl, and halide, and each of $R^{7A}$, $R^{7B}$, and $R^{7C}$ is independently selected from the group consisting of, but not limited to, hydrogen, deuterium, alkyl, aryl and acetyl. The narrow-band monomer can be integrated into a backbone of the polymer (e.g., along the backbone of the polymer by polymerizing in the polymer) and/or attached by covalent attachment to the backbone, a terminus, or a sidechain of the polymer through at least one attachment to $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$, $R^{7C}$ or a combination thereof. Alternatively, as shown here, the monomer described herein can be integrated with the polymer by attachment as shown by the parentheses.

Hybrid polymer dots of the present disclosure can include a polymer that includes a narrow-band monomer having the structure of Formula (XXVII):

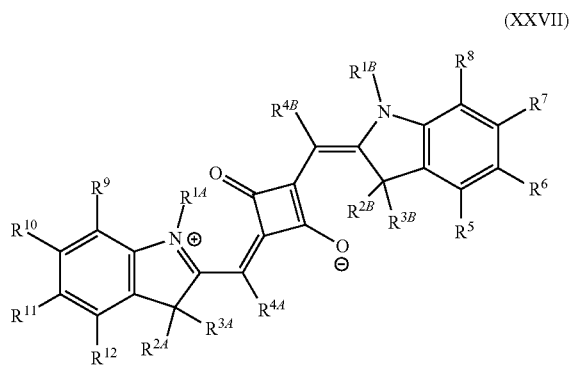

(XXVII)

wherein each of $R^{1A}$ and $R^{1B}$ is independently selected from the group consisting of, but not limited to, hydrogen, deuterium, alkyl and aryl; and each of $R^{2A}$, $R^{2B}$, $R^{3A}$, $R^{3B}$, $R^{4A}$, $R^{4B}$, $R^5$, $R^6$, $R^7$, $R^8$, $R^9$, $R^{10}$, $R^{11}$ and $R^{12}$ are independently selected from the group consisting of, but not limited to, hydrogen, deuterium, alkyl, aryl, cyano, amino, sulfide, aldehyde, ester, ether, carboxyl, hydroxyl, and halide. The narrow-band monomer can be integrated into a backbone of the polymer (e.g., along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$, $R^5$, $R^6$, $R^7$, $R^8$, $R^9$, $R^{10}$, $R^{11}$, $R^{12}$ or a combination thereof.

Hybrid polymer dots of the present disclosure can include a polymer that includes a narrow-band monomer having the structure of Formula (XXVIII):

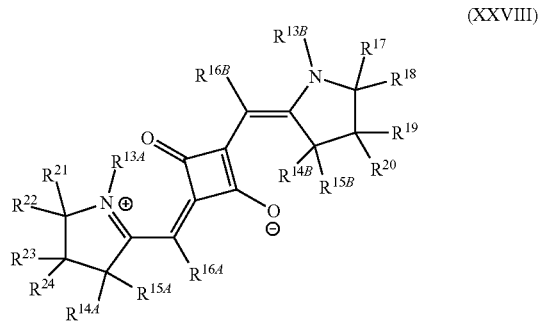

(XXVIII)

wherein each of $R^{13A}$, $R^{13B}$ is independently selected from the group consisting of, but not limited to, hydrogen, deuterium, alkyl and aryl; and $R^{14A}$, $R^{14B}$, $R^{15A}$, $R^{15B}$, $R^{16A}$, $R^{16B}$, $R^{17}$, $R^{18}$, $R^{19}$, $R^{20}$, $R^{21}$, $R^{22}$, $R^{23}$ and $R^{24}$ are each independently selected from the group consisting of, but not limited to, hydrogen, deuterium, alkyl, aryl, cyano, amino, sulfide, aldehyde, ester, ether, carboxyl, hydroxyl, and halide. The narrow-band monomer can be integrated into a backbone of the polymer (e.g., along the backbone of the polymer by polymerizing in the polymer) and/or attached by covalent attachment to the backbone, a terminus, or a sidechain of the polymer through at least one attachment to $R^{13A}$, $R^{13B}$, $R^{14A}$, $R^{14B}$, $R^{15A}$, $R^{15B}$, $R^{16A}$, $R^{16B}$, $R^{17}$, $R^{18}$, $R^{19}$, $R^{20}$, $R^{21}$, $R^{22}$, $R^{23}$ and $R^{24}$ or a combination thereof.

In some embodiments, the narrow-band emissive polymers for making hybrid polymer dots include metal complexes and their derivatives as narrow-band monomers. Metal complexes and their derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The metals can be any metal such as Na, Li, Zn, Mg, Fe, Mn, Co, Ni, Cu, In, Si, Ga, Al, Pt, Pd, Ru, Rh, Re, Os, Ir, Ag, Au and so on. In some embodiments the metal can be Fe, Ni, Co, Ga, or Au. In some embodiments the metal can be Fe, Ni, Co, Ga, oxides thereof, alloys thereof, complexes thereof, combinations thereof, and combinations and complexes with non-magnetic or non-magnetic metals. The metal complexes can be energy acceptors and other monomers can be energy donors so that the final hybrid polymer dots can exhibit narrow-band emissions. The narrow-band emissive chromophoric polymers in good solvents may exhibit broad emissions or narrow emissions. However, in some embodiments, their nanoparticle form gives narrow-band emissions. In some embodiments, the emission FWHM of the above hybrid polymer dots is less than 70 nm. In certain embodiments, the FWHM is less than 60 nm, less than 50 nm, less than 40 nm, less than 30 nm, or less than 20 nm. Metal complexes and metal complex derivatives can be polymerized to form polymers (e.g., homopolymers or heteropolymers) and/or can be attached (e.g., covalently attached) to a polymer backbone, sidechain and/or terminus.

In some embodiments, the narrow-band emissive polymers for making hybrid polymer dots include porphyrin, metalloporphyrin, and their derivatives as narrow-band monomers. Porphyrin, metalloporphyrin, and their derivatives can be polymerized to form polymers (e.g., homopolymers or heteropolymers) and/or can be attached (e.g., covalently attached) to a polymer backbone, sidechain and/or terminus. Porphyrin, metalloporphyrin, and their derivatives include but are not limited to their alkyl derivatives, aryl derivatives, alkyne derivatives, aromatic derivatives, alkoxide derivatives, aza derivatives, their extended systems and analogues. The metals in the metalloporphyrins can be any metal such as Na, Li, Zn, Mg, Fe, Mn, Co, Ni, Cu, In, Si, Ga, Al, Pt, Pd, Ru, Rh, Re, Os, Ir, Ag, Au and so on. In some embodiments the metal can be Fe, Ni, Co, Ga, or Au. In some embodiments the metal can be Fe, Ni, Co, Ga, oxides thereof, alloys thereof, complexes thereof, combinations thereof, and combinations and complexes with magnetic or non-magnetic metals. The narrow-band emissive polymers can also include any other monomers. The porphyrin, metalloporphyrin and their derivatives can be energy acceptors and other monomers can be energy donors so that the final hybrid polymer dots can exhibit narrow-band emissions. The narrow-band emissive chromophoric polymers in good solvents may exhibit broad emissions or narrow emissions. However, in some embodiments, their nanoparticle form gives narrow-band emissions. In some embodiments, the emission FWHM of the above hybrid polymer dots is less than 70 nm. In certain embodiments, the FWHM is less than 60 nm, less than 50 nm, less than 40 nm, less than 30 nm, or less than 20 nm.

In some embodiments, the narrow-band emissive polymers for making hybrid polymer dots include phthalocyanine and its derivatives as monomers. Phthalocyanine and its derivatives as monomers can be polymerized to form polymers (e.g., homopolymers or heteropolymers) and/or can be attached (e.g., covalently attached) to a polymer backbone, sidechain and/or terminus. Phthalocyanine derivatives include but are not limited to their alkyl derivatives, aryl derivatives, alkyne derivatives, aromatic derivatives, alkoxide derivatives, aza derivatives, their extended systems and analogues. The metals in the phthalocyanine derivatives can be any metal such as Na, Li, Zn, Mg, Fe, Mn, Co, Ni, Cu, In, Si, Ga, Al, Pt, Ru, Rh, Re, Os, Ir, Ag, Au or Pd. In some embodiments the metal can be Fe, Ni, Co, Ga, or Au. In some embodiments the metal can be Fe, Ni, Co, Ga, oxides thereof, alloys thereof, complexes thereof, combinations thereof, and combinations and complexes with magnetic or non-magnetic metals. The narrow-band emissive polymers can also include any other monomers. The phthalocyanine derivatives can be energy acceptors so that the final hybrid polymer dots can exhibit narrow-band emissions. The narrow-band emissive chromophoric polymers in good solvents may exhibit broad emissions or narrow emissions. However, in some embodiments, their nanoparticle form gives narrow-band emissions. In some embodiments, the emission FWHM of the above hybrid polymer dots is less than 70 nm. In certain embodiments, the FWHM is less than 60 nm, less than 50 nm, less than 40 nm, less than 30 nm, or less than 20 nm.

A wide variety of chromophoric polymer particles can be used in accordance with the embodiments herein, such as the examples described herein as well as others that are disclosed, e.g., in PCT/US2010/056079 and PCT/US2012/071767, each of which is incorporated by reference herein it its entirety and specifically with regard to the particular chromophoric polymer particle compositions and the respective methods of making them as described therein.

Functionalization and Bioconjugation of Hybrid Polymer Dots

In some embodiments, the present disclosure provides hybrid polymer dots having a functional group (e.g., "X") that is physically and/or chemically attached to the polymer dot, also referred to herein as a functionalized hybrid polymer dot. In some embodiments, the term "functional group" refers to any chemical unit that can be attached, such as by any stable physical or chemical association, to the hybrid polymer dot, thereby rendering the surface of the hybrid polymer dot available for conjugation or bioconjugation. In some embodiments, functionalization occurs such that functional groups suitable for bioconjugation are oriented on the surface of the polymer dot. For example, the organic-inorganic hybrid polymer dots herein can have a surface that is functionalized with a functional silane species comprising a carboxyl, an amine, a thiol (—SH), a carboxylate or carboxylic acid, a maleimide, a maleic anhydride, a N-hydroxysuccinimide (NHS), an alcohol (—OH), or a cyanate, or a combination thereof, that is suitable for bioconjugation.

In some embodiments, functional groups can be hydrophobic functional groups. Examples of hydrophobic functional groups include but not limited to alkyne, strained alkyne, azide, diene, alkene, cyclooctyne, and phosphine groups (for click chemistry). In some embodiments, functional groups can be hydrophilic functional groups. Examples of hydrophilic functional groups include but not limited to carboxylic acid or salts thereof, amino, mercapto, azido, diazo, aldehyde, ester, hydroxyl, carbonyl, sulfate, sulfonate, phosphate, cyanate, succinimidyl ester, substituted derivatives thereof. Such functional groups can be found by one of ordinary skill in the art, for example in Bioconjugate Techniques (Academic Press, New York, 1996 or later versions) the content of which is herein incorporated by reference in its entirety for all purposes.

In some embodiments, hybrid polymer dots are functionalized using functional groups including, without limitation, any the following: an aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or combination thereof.

In some embodiments, a functional group is created with covalent bonding to the backbone, side chain, or terminating unit of the chromophoric polymer. Therefore, the resulting hybrid polymer dots exhibit narrow-band emission and simultaneously have functional groups for bioconjugation. Such functional groups could be found by one of ordinary skill in the art, for example in Bioconjugate Techniques (Academic Press, New York, 1996 or later versions) the content of which is herein incorporated by reference in its entirety for all purposes. In some embodiments, each hybrid polymer dot has only one functional group. In some embodiments, each hybrid polymer dot has only two functional groups. The two functional groups can be the same or different. In some embodiments, each hybrid polymer dot has three or more functional groups. The three or more functional groups can be the same or different.

In certain embodiments of the present disclosure, the degree of functionalization of the hybrid polymer dot can be varied as desired. In some embodiments, the hybrid polymer dots provided herein are modified to form a single-molecule polymer particle that can be monovalent, bivalent, or multivalent. The modification is to remove some polymer molecules from the particle, but leave only one molecule that can have just one functional group, two or more functional groups. In one embodiment, an engineered surface can be used to facilitate the modification. The engineered surface can have certain functional groups such as aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, and combinations thereof. In general, any other functional groups that are suitable for bioconjugation can be used. Such functional groups could be found by one of ordinary skill in the art, for example in Bioconjugate Techniques (Academic Press, New York, 1996 or later versions). The surface can be a flat surface such as a coverslip or a curved surface from any particles. The surfaces can be silica, metal, semiconducting, silicon, and different polymer surfaces. The functionalized multi-molecule hybrid polymer dot described above is attached to the surface by only one chromophoric polymer molecule via any stable physical or chemical association. All the free molecules (except the one associated with the surface) in the hybrid polymer dot can be removed, such as by washing the surface with an organic solvent, so that only the molecule associated with the surface is retained. Then the single-molecule hybrid polymer dot can be released from the surface by any physical or chemical methods. The resulting single-molecule particle could be monovalent, bivalent, or multivalent, depending on the number of functional groups in the original polymer molecule. In another embodiment, all the functional groups (except the one associated with the surface) in the hybrid polymer dot can be inactivated or reacted to form other types of functional groups or non-reactive chemical groups for bioconjugation, such that after release from the surface, the remaining functional group (the one attached to the surface) can be used for bioconjugation.

In some embodiments, advantages can arise from using hybrid polymer dots that include a single polymer molecule having at least one functional group at a terminal unit. For example, the attachment of only one functional group to a terminal unit of a chromophoric polymer can be well controlled in polymer synthesis. For example, a chemical unit comprising a functional group can serve as a polymerization initiator as well as a growth catalyst in polymer synthesis, and in this way each polymer molecule includes just one functional group at the terminus. Attachment of functional groups only to the two terminal units of a linear chromophoric polymer can also be well controlled in polymer synthesis. For example, a chemical unit comprising a functional group can be used as a capping agent to terminate the polymer growth in polymer synthesis, thereby resulting in each linear polymer molecule including only two functional groups in the two terminal units. Similarly, the attachment of functional groups for multivalent polymer particles can be well controlled in polymer synthesis, e.g., functional groups can only be added to the three terminal units of a three-arm branched polymer.

In some embodiments, the present disclosure provides a bioconjugate of the hybrid polymer dot. The bioconjugates also include hybrid polymer dots as described above associated with biological particles such as viruses, bacteria, cells, biological or synthetic vesicles such as liposomes, or combinations thereof. In some embodiments, the terms "biomolecule" or "biological molecule" are used interchangeably to describe a synthetic or naturally occurring protein, glycoprotein, peptide, amino acid, metabolite, drug, toxin, nuclear acid, nucleotide, carbohydrate, sugar, lipid, fatty acid, and the like, or combinations thereof. In some embodiments, the biomolecule is a polypeptide or a polynucleotide. In some embodiments, the biomolecule is an antibody, an avidin, a biotin, a nucleic acid, or a combination thereof. In some embodiments, the bioconjugate is formed by the attachment of a biomolecule to one or more functional groups of the hybrid polymer dot. The attachment may be direct or indirect. Optionally, the biomolecule is attached to the functional group of the hybrid polymer dot via a covalent bond. For example, if the functional group of the polymer particle is a carboxyl group, a protein biomolecule can be directly attached to the hybrid polymer dot by cross-linking the carboxyl group with an amine group of the protein molecule. In some embodiments, each polymer particle has only one type of biomolecule attached. In some embodiments, the biomolecular conjugation does not change substantively the emissive properties of the hybrid polymer dot. For example, the bioconjugation does not substantively change the emission spectra, does not reduce fluorescence or luminescence quantum yield, does not substantively change the photostability, etc.

Some of the functional groups of a hybrid polymer dot can be "suitable for bioconjugation," which refers to a functional group that is or that is capable of being covalently bonded to a biomolecule, such as an antibody, protein, nucleic acid, streptavidin, or other molecule of biological relevance. Functional groups can render the surface of the hybrid polymer dots available for conjugation or bioconjugation. The hybrid polymer dots can include one or more functional groups that are formed from the siloxane network. Such functional groups can be found by one of ordinary skill in the art, for example in Bioconjugate Techniques (Academic Press, New York, 1996 or later versions) the content of which is herein incorporated by reference in its entirety for all purposes. In some embodiments, functional groups suitable for bioconjugation can include functional groups that can be conjugated to a biomolecule under a variety of conditions, such as, e.g., in polar or non-polar solvents. In certain embodiments, functional groups suitable for bioconjugation can include functional groups that can be conjugated to a biomolecule in an aqueous solution. In some embodiments, functional groups suitable for bioconjugation can include functional groups that can be conjugated to a biomolecule in an aqueous solution in which the biomolecule retains its biological activity (e.g., monoclonal binding specificity for an antibody).

In certain embodiments, functional groups suitable for bioconjugation are covalently bonded to a biomolecule. For example, typical covalent bonding attachments of functional groups to biomolecules can include, e.g., a carboxyl functional group reacting with an amine on a biomolecule to form an amide bond, a sulfhydryl functional group reacting with a sulfhydryl group on a biomolecule to form a cysteine bond, or an amino functional group reacting with a carboxyl group on a biomolecule to form an amide bond. A biomolecule can be attached to a hybrid polymer dot either directly or indirectly by the functional groups so as to form a bioconjugate. The biomolecule can be attached to a functional group of a hybrid polymer dot via a covalent bond. For example, if the functional group of the hybrid polymer dot is a carboxyl group, a protein biomolecule can be directly attached to the polymer dot by cross-linking the carboxyl group with an amine group of the protein molecule.

Functional groups suitable for bioconjugation can comprise an amine, a carboxylate, a carboxyl, a maleimide, a thiol (—SH), a maleic anhydride, an N-hydroxysuccinimide ester, a mercapto, an azido, an alkyne, an aldehyde, a hydroxyl, a carbonyl, a sulfate, a sulfonate, a phosphate, a cyanate, a succinimidyl ester, a strained alkyne, an azide, a diene, an alkene, a tetrazine, a strained alkene, a cyclooctyne, or a phosphine. In some embodiments, a functional group suitable for bioconjugation is a carboxyl group.

Indirect attachment of the biomolecule to hybrid polymer dots can occur through the use of a linker moiety (e.g., "L"), for example, avidin, streptavidin, neutravidin, biotin, or the like. Linker moieties can be selected from a chemical bond, an amino acid, an ester, an amide, a carbamate, an ether, an alkylene, an alkenylene, an alkynylene, an arylene, a polyether, a polyester, a polyamide, a polycarbamate, a polyaryl, a polystyrene, polyethylene glycol, or a polyolefin, or a fluorinated or partially fluorinated derivative thereof, or a combination thereof. In some embodiments, a linker moiety is amphiphilic. In some embodiments, a linker moiety is a water-soluble polymer. For example, the water-soluble polymer can be polyethylene glycol. In some embodiments, a linker moiety is a chemical bond.

A functional group suitable for bioconjugation can be combined with a linker moiety to facilitate bioconjugation. In the hybrid polymer dots described herein, at least one functional group suitable for bioconjugation combined with a linker moiety (e.g., "D" or "LX") can be positioned on the surface of the hybrid polymer dot. In some embodiments, a biological molecule is conjugated to functional group suitable for bioconjugation combined with a linker moiety. In some embodiments, a biological molecule is conjugated to a functional group suitable for bioconjugation combined with a linker moiety positioned on the surface of the hybrid polymer dot. In some embodiments, the biological molecule comprises a protein or a nucleic acid. In some embodiments, the biological molecule comprises an antibody. In some embodiments, the biological molecule comprises streptavidin.

In various embodiments of the present disclosure crosslinking agents can be utilized to facilitate bioconjugation of hybrid polymer dots. In some embodiments, the term "crosslinking agent" is used to describe a compound or moiety that is capable of forming a chemical bond between molecular groups on similar or dissimilar molecules so as to covalently bond together the molecules. Examples of common crosslinking agents are known in the art. See, for example, Bioconjugate Techniques (Academic Press, New York, 1996 or later versions). Indirect attachment of the biomolecule to hybrid polymer dots can occur through the use of "linker" molecules, for example, avidin, streptavidin, neutravidin, biotin or a like molecule.

In some embodiments, analysis of a target analyte molecule (e.g., a protein) is achieved using hybrid polymer dots conjugated to biomolecules that specifically bind to the target analyte.

In some embodiments, fluorescent and/or luminescent hybrid polymer dots are conjugated to one or more molecules that provide a function or other benefit, including without limitation, binding affinity for a target analyte.

In some embodiments, the analyte is a polypeptide, a polynucleotide, a cell, a virus, a small molecule, a drug, a toxin, a carbohydrate, a sugar, a lipid, or a fatty acid.

In some embodiments, the target analyte molecule is a polypeptide, such as a protein, and the biomolecule conjugated to a hybrid polymer dot is a primary antibody that specifically binds to the target analyte protein.

In other embodiments, the target analyte molecule is a protein of interest bound to a primary antibody for said protein, and the biomolecule conjugated to a hybrid polymer dot is a secondary antibody that specifically binds to the primary antibody.

In other embodiments, the target analyte molecule is a biotinylated protein of interest, and the biomolecule conjugated to a hybrid polymer dot is an avidin (e.g., streptavidin) that specifically binds to the biotinylated protein.

In some embodiments, the term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

In some embodiments, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is an avidin protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin.

In some embodiments, the target analyte molecule is a polynucleotide, such as DNA, RNA, or PNA, and the biomolecule conjugated to a hybrid polymer dot is a complementary polynucleotide that specifically binds to the target analyte polynucleotide.

In some embodiments, hybrid polymer dots may be conjugated to one or more molecules that alter other properties of the polymer particles, such as their size, fluorescence, hydrophobicity, non-specific binding or adsorption properties, and the like.

In some embodiments, conjugation of biomolecules to hybrid polymer dots can include attachment of a functional group, including but not limited to attachment of carboxyl groups to polymer particles. In some embodiments, carboxyl groups can be reacted to N-hydroxysuccinimide (NHS) in the presence of a carbodiimide such as 1-ethyl-3-[3-dimethylaminopropyl]carbodiimide hydrochloride (EDC) to produce amine-reactive esters of carboxylate groups for crosslinking with primary amine groups present on certain biomolecules.

In some embodiments, carboxylated hybrid polymer dots are conjugated to a biomolecule, such as a protein, by mixing of the hybrid polymer dots and the biomolecules, e.g., in a HEPES buffer (20 mM, pH=7.4) solution containing 0.1 PEG (MW3350). Formation of a peptide bond between the carboxyl groups on polymer particles and the amine groups of the biomolecule can be catalyzed by EDC. However, in some embodiments, due to the intrinsically hydrophobic nature of the polymer particles, biomolecules tend to nonspecifically adsorb onto the particle surface. In some embodiments, Triton X-100 and/or bovine serum albumin (BSA) are introduced to reduce non-specific adsorption of a biomolecule onto the surface of a polymer particle.

In addition to the examples described herein, in some embodiments other strategies and methods for conjugation of biomolecules to hybrid polymer dots can be used, including those disclosed, e.g., in PCT/US2010/056079 and PCT/US2012/071767. Other strategies and methods for conjugation of biomolecules to hybrid polymer dots can be found by one of ordinary skill in the art, for example in Bioconjugate Techniques (Academic Press, New York, 1996 or later versions).

Methods of Making Organic-Inorganic Hybrid Polymer Dots

The present disclosure provides methods of making hybrid polymer dots as disclosed herein. In certain embodiments, one or more polymers are collapsed, precipitated, or condensed to form an organic network and an inorganic network, which together form the organic-inorganic interpenetrated network as described herein.

For example, the methods can comprise: providing a solution (e.g., an organic solution), wherein the solution comprises a solvent, a semiconducting chromophoric polymer, and an organo-silane; and mixing the solution with an aqueous solution, wherein the solution, the aqueous solution, or both comprise an organo-silane comprising X, where X is a functional group suitable for bioconjugation. For instance, if the organo-silane comprising X is relatively hydrophobic, it can be provided in the solution with the solvent. Conversely, if the organo-silane comprising X is relatively hydrophilic, it can be provided in the aqueous solution.

FIG. 1 shows an exemplary schematic illustration for preparing hybrid Pdots. In some embodiments, an organic solution (e.g., a THF solution) including a polymer (e.g., chromophoric semiconducting polymer) and an alkyl silane is provided. The organic solution is injected into an aqueous solution. In certain embodiments, the organic solution includes a silane with one or more functional groups (e.g., X). Alternatively or in combination, the aqueous solution includes a silane with one or more functional groups (e.g., X). Introduction of the organic solution into the aqueous solution produces hybrid polymer dots with functional groups.

Optionally the organic solution further includes a silane. In some embodiments, inclusion of a silane in the organic solution reduces the overall size of the hybrid resultant polymer dot.

In some embodiments, the organo-silane is selected from:

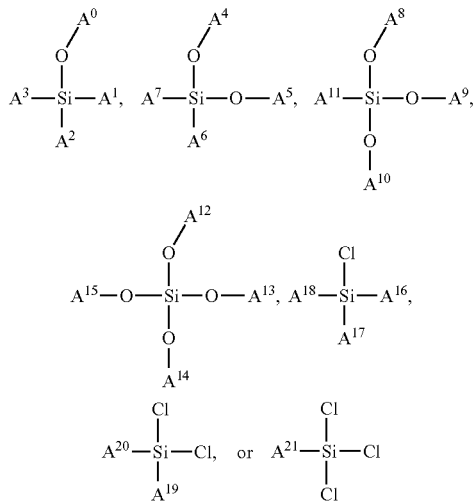

wherein: $A^1, A^2, A^3, A^6, A^7, A^{11}, A^{16}, A^{17}, A^{18}, A^{19}, A^{20}$, and $A^{21}$ are each independently $C_nH_{2n+1}$, $C_nH_{2n}X$, $C_nF_{2n+1}$, or $C_nF_{2n}X$; $A^0, A^4, A^5, A^8, A^9, A^{10}, A^{12}, A^{13}, A^{14}$, and $A^{15}$ are each independently $C_mH_{2m+1}$, $C_mH_{2m}X$, $C_mF_{2m+1}$, or $C_mF_{2m}X$; n is not less than 1; and m is not less than 1. In some embodiments, n is not less than 2, not less than 3, not less than 4, not less than 5, not less than 6, not less than 7, not less than 8, not less than 9, or not less than 10. In some embodiments, n is not less than 6. In some embodiments, n is not greater than 20. In some embodiments, n is not greater than 40. In some embodiments, n is not greater than 60. In some embodiments, n is not less than 6 and is not greater than 20. In some embodiments, n is not less than 6 and is not greater than 15. In some embodiments, n is not less than 6 and is not greater than 10. In some embodiments, m is not less than 2, not less than 3, not less than 4, not less than 5, not less than 6, not less than 7, not less than 8, not less than 9, or not less than 10. In some embodiments, m is not greater than 5, not greater than 6, not greater 7, not greater than 8, not greater than 9, or not greater than 10. In some embodiments, m is not greater than 20. In some embodiments, m is not greater than 40. In some embodiments, m is not greater than 60. In some embodiments, m is not less than 1 and is not greater than 20.

The organo-silane comprising X can be selected from:

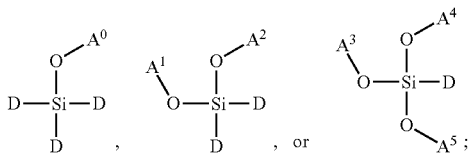

wherein: $A^0, A^1, A^2, A^3, A^4$, and $A^5$, are each independently $C_mH_{2m+1}$, $C_mH_{2m}X$, $C_mF_{2m+1}$, or $C_mF_{2m}X$; D is LX, wherein L is a linker moiety; and m is not less than 1. In some embodiments, L can be, but is not limited to, an amino acid, an ester, an amide, a carbamate, an ether, an alkylene, an alkenylene, an alkynylene, an arylene, a polyether, a polyester, a polyamide, a polycarbamate, a polyaryl, a polystyrene, or a polyolefin, or a fluorinated or partially fluorinated derivative thereof, or a combination thereof. In some embodiments, L is a water-soluble polymer. In certain embodiments, the water-soluble polymer can be polyethylene glycol. In other embodiments, L can be a chemical bond. In some embodiments, m is not less than 3. In some embodiments, m is not less than 6. In some embodiments, m is not greater than 5, not greater than 6, not greater 7, not greater than 8, not greater than 9, or not greater than 10. In some embodiments, m is not greater than 20. In some embodiments, m is not greater than 40. In some embodiments, m is not greater than 60. In some embodiments, m is not less than 1 and is not greater than 20.

In some embodiments, n is not less than 1, not less than 2, not less than 3, not less than 4, not less than 5, not less than 6, not less than 7, not less than 8, not less than 9, or not less than 10. In some embodiments, n is not less than 6. In some embodiments, n is not greater than 20. In some embodiments, n is not greater than 40. In some embodiments, n is not greater than 60. In some embodiments, n is not less than 6 and is not greater than 20.

In some embodiments, m is not less than 1, not less than 2, not less than 3, not less than 4, not less than 5, not less than 6, not less than 7, not less than 8, not less than 9, or not less than 10. In some embodiments, m is not less than 6. In some embodiments, m is not greater than 20. In some embodiments, m is not greater than 40. In some embodiments, m is not greater than 60. In some embodiments, m is not less than 1 and is not greater than 20.

The organo-silane can be selected from an alkyl silane, an alkoxy silane, a chloro silane, an orthosilicate, a siloxane, an alpha silane, an acetoxy silane, an amino silane, a bis silane, an epoxy silane, a halo silane, a hydrogen silane, a hydroxyl silane, an ester silane, an aryl silane, an acryl silane, a methacryl silane, a styryl silane, a vinyl silane, an olefin silane, a sulfur silane, a phosphine silane, a phosphate silane, an isocyanate silane, an azide silane, an anhydride silane, or a hydrogen siloxane, or a combination thereof. Specifically, the organo-silane can be selected from octodecyltrimethoxysilane, octodecyltrichlorosilane, tetraethylorthosilicate, trifluoropropyltrimethoxysilane, phenyltrimethoxysilane, chloropropyltrimethoxysilane, heptadecafluorodecyltrichlorosilane, glycidoxypropyltrimethoxysilane, epoxyhexyltriethoxysilane, hydroxymethyltriethoxysilane, iodopropyltrimethoxysilane, isocyantopropyltrimethoxysilane, methacryloxymethyltriethoxysilane, vinyltrimethoxysilane, styrylethyltrimethoxysilane, or a combination thereof. More specifically, the organo-silane can be selected from octodecyltrimethoxysilane, octodecyltrichlorosilane, or tetraethylorthosilicate, or a combination thereof.

In some embodiments, an organo-silane is used to form a hybrid polymer dot including a siloxane network, and the weight percent of the siloxane network and/or the components thereof (e.g., silicon) in a hybrid polymer dot can be varied as desired. In some embodiments, the weight percent of the siloxane network and/or the components thereof (e.g., silicon) is selected to avoid formation of a core-shell structure in the resulting hybrid polymer dot. In certain embodiments, the weight percent of silicon from the siloxane network in the hybrid polymer dot is less than or equal to about 1%, less than or equal to about 5%, less than or equal to about 10%, less than or equal to about 15%, less than or equal to about 20%, less than or equal to about 25%, less than or equal to about 30%, less than or equal to about 35%, less than or equal to about 40%, less than or equal to about 45%, or less than or equal to about 47%. In certain embodiments, the weight percent of silicon from the siloxane network in the hybrid polymer dot is greater than or equal to about 1%, greater than or equal to about 5%, greater than or equal to about 10%, greater than or equal to about 15%, greater than or equal to about 20%, greater than or equal to about 25%, greater than or equal to about 30%, greater than or equal to about 35%, greater than or equal to about 40%, or greater than or equal to about 45%. In certain embodiments, the weight percent of silicon from the siloxane network in the hybrid polymer dot is within a range from about 1% to about 45%, or within a range from about 1% to about 47%.

In some embodiments, the methods comprise providing a first organo-silane including a functional group and, optionally, a second organo-silane. The first organo-silane can be provided in an aqueous solution, in an organic solution, or both. The optional second organo-silane can be provided in an organic solution. The organic and aqueous solutions can be combined in order to form hybrid polymer dots.

In some embodiments, the methods disclosed herein can comprise heating the organic solution or the aqueous solution, or a combination thereof. The aqueous solution can be alkaline. In some embodiments, the aqueous solution can have a pH not less than 9. In some embodiments, the aqueous solution can have a pH of not less than 10 and not greater than 11.

The aqueous solution can be acidic. In some embodiments, the aqueous solution has a pH of not greater than 6. In some embodiments, the aqueous solution has a pH of not greater than 5. In some embodiments, the aqueous solution has a pH of not greater than 4.

In some embodiments, the hybrid polymer dots made according to the methods disclosed herein can comprise a plurality of polymers, such as one or more of the chromophoric polymers described herein. In some embodiments, the polymer dot can comprise a plurality of semiconducting chromophoric polymers. In some embodiments, the polymer dot comprises a blend of semiconducting polymers. In some embodiments, the polymer dot can comprise a blend of semiconducting polymers and non-semiconducting polymers. In some embodiments, the polymer dot can comprise semiconducting chromophoric polymer. In some embodiments, the polymer dot can comprise a blend of semiconducting chromophoric polymers. In some embodiments the semiconducting chromophoric polymer can comprise a fluorene polymer, a fluorene-based polymer or copolymer, a phenylene vinylene-based polymer or copolymer, a phenylene ethynylene-based polymer or copolymer, or a BODIPY-based polymer or copolymer. In other embodiments, the semiconducting chromophoric polymer can comprise poly(9,9-dihexylfluorenyl-2,7-diyl) (PDHF), Poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}](PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), poly[(9,9-dioctylfluorenyl-2,7-diyl)-9-co-(4,7-Di-2-thienyl-2,1,3-benzothiadiazole)] (PF-0.1TBT)), poly[2-methoxy-5-(2-ethylhexyloxy)-1,4-phenylenevinylene] (MEH-PPV), poly[2-methoxy-5-(2-ethylhexyloxy)-1,4-(1-cyanovinylene-1,4-phenylene)] (CN-PPV), or a semiconducting polymer comprising BODIPY monomer and emitting units, including BODIPY 570, BODIPY 590, or BODIPY 690. The polymer dot can comprise a BODIPY derivative. In some embodiments, the BODIPY derivative has the structure of Formula (I):

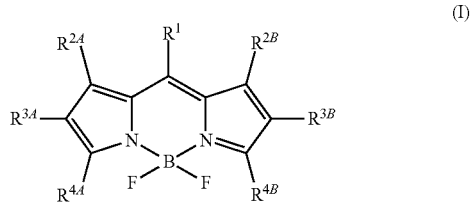

wherein each of $R^1$, $R^{2A}$, $R^{2B}$, $R^{3A}$, $R^{4A}$ and $R^{4B}$ is independently selected from hydrogen, alkyl, aralkyl, aryl, and alkoxy-aryl, and wherein the BODIPY derivative is integrated into the chromophoric polymer by attachment to $R^1$, $R^{2A}$, $R^{2B}$, $R^{3A}$, $R^{4A}$, and $R^{4B}$, or a combination thereof.

X can comprise an amine, a carboxylate, a carboxyl, a maleimide, a thiol (—SH), a maleic anhydride, an N-hydroxysuccinimide ester, a mercapto, an azido, an alkyne, an aldehyde, a hydroxyl, a carbonyl, a sulfate, a sulfonate, a phosphate, a cyanate, a succinimidyl ester, a strained alkyne, an azide, a diene, an alkene, a tetrazine, a strained alkene, a cyclooctyne, or a phosphine. Specifically, X can comprise a carboxyl group.

L can be selected from a chemical bond, an amino acid, an ester, an amide, a carbamate, an ether, an alkylene, an alkenylene, an alkynylene, an arylene, a polyether, a polyester, a polyamide, a polycarbamate, a polyaryl, a polystyrene, or a polyolefin, or a fluorinated or partially fluorinated derivative thereof, or a combination thereof. Specifically, L can be a water-soluble polymer. The water-soluble polymer can be polyethylene glycol. Alternatively, L can a chemical bond.

At least one D can be positioned on the surface of the polymer dot made according to the methods disclosed herein. In some embodiments, a biological molecule is conjugated to D. In some embodiments, the biological molecule is conjugated to at least one D positioned on the surface of the polymer dot. In some embodiments, a biological molecule is conjugated to a D positioned on the surface of the nanoparticle. In some embodiments, the biological molecule can comprise a protein or a nucleic acid. In some embodiments, the biological molecule can comprise an antibody. In some embodiments, the biological molecule can comprise streptavidin.

Methods of Using Organic-Inorganic Hybrid Polymer Dots

The present disclosure further provides methods of using the hybrid polymer dots described herein. For example, the present disclosure provides methods of fluorescence-based detection using the polymer dots disclosed herein as a novel class of fluorescent probe and their bioconjugates for a variety of applications. These include but are not limited to flow cytometry, fluorescence activated sorting, immunofluorescence, immunohistochemistry, fluorescence multiplexing, DNA and gene analysis, fluorescence in situ hybridization (FISH), polymerase chain reaction (PCR) analysis, isothermal DNA or RNA amplification based analysis, protein analysis, metabolite analysis, lipid analysis, Förster resonance energy transfer (FRET)-based sensors, high throughput screening, cell detection, bacteria detection, virus detection, biomarker detection, cellular imaging, in vivo imaging, bioorthogonal labeling, Pdot sensors, Pdot transducer-based sensors, fluorescence-based biological assays such as immunoassays and enzyme-based assays, and a variety of fluorescence techniques in biological assays and measurements. In certain embodiments, the hybrid polymer dots herein have a number of advantages for use as detection agents, e.g., for detection of proteins or peptides such as in the course of Western blot analysis. Hybrid polymer dots according to the present disclosure can comprise any suitable polymer subunit or subunits that enable the detection of proteins or peptides, and in particular, proteins. Hybrid polymer dots according to the present disclosure can comprise any suitable polymer subunit or subunits that enable the detection of nucleic acids, and in particular, DNA or RNA.

In some embodiments, hybrid polymer dots can provide superior photophysical properties, such as high emission brightness for fluorescence-based detection methods. In some embodiments, hybrid polymer dots can provide superior specific-cellular-targeting capabilities, such as minimal non-specific adsorption or interactions with the target cell or cellular structure or immobilized biomolecules. In some embodiments, methods of fluorescence-based detection can include detecting light emitted from an organic-inorganic hybrid polymer dot comprising a semiconducting chromophoric polymer and an inorganic network, wherein the semiconducting chromophoric polymer and the inorganic network form an organic-inorganic interpenetrated network. The inorganic network may be, for example, a siloxane network, a titanium-oxide network, or a titanium-siloxane network, or any of the other inorganic networks described herein.

The hybrid polymer dots disclosed herein may be conjugated to biological molecules, such as cells. Hybrid polymer dots can comprise chromophoric polymers, providing a source of fluorescence which may be used to label, detect, and track such conjugated biological molecules. Such labeling may be used, for example, for sorting of particles in flow cytometry, using methods such as fluorescence-activated cell sorting (FACS). Such labeling may be used, for example, for detecting the presence of molecules using immunoassays (e.g., ELISA). Such labeling may be used, for example, for detecting the presence of nucleic acids using nucleic acid amplification schemes, which may employ thermalcycling (e.g., PCR) or may employ isothermal schemes (e.g., LAMP, NASBA, RPA, RCA, etc.). Such labeling may be used, for example, for detecting the presence of nucleic acids using non-amplification schemes (e.g., with Molecular Beacons). The fluorescence properties of hybrid polymer dots may be altered via conjugation to biological particles, allowing the particles to be sorted according to their state of conjugation. Conjugated hybrid polymer dots may also be used in optical identification of cells or other biological particles in solution, or adhered to a solid surface. Hybrid polymer dots provide the ability to label biological particles while remaining biocompatible and having a high density and smaller size than that available in many previously disclosed polymer dots.

In some embodiments, a method of detecting analytes is provided, the method comprising contacting a sample comprising an analyte with a hybrid polymer dot. In other embodiments, the method comprises contacting a sample comprising an analyte with a suspension of hybrid polymer dots. In some embodiments, the sample comprises blood, urine, stool, lymph, saliva, tears, or cerebrospinal fluid. In some embodiments, the sample is derived from a subject, such as a human subject, an animal or a single-celled organism. In some embodiments, the sample comprises a living animal or tissue. In some embodiments, the analyte has a binding affinity for a biomolecule attached to a hybrid polymer dot. In some embodiments, the analyte comprises a polypeptide, a polynucleotide, a cell, a cellular fraction, a virus, a drug, a toxin, a carbohydrate, a sugar, a lipid, or a fatty acid.

In some embodiments, the method further comprises measuring a signal emitted from the sample, the suspension, and/or a hybrid polymer dot. In some embodiments, the method further comprises using a signal emitted from the sample and/or the suspension to measure the analyte.

In some embodiments, the method further comprises exciting the sample, the suspension, and/or a hybrid polymer dot with a source of electromagnetic radiation. In some embodiments, the electromagnetic radiation passes through a spectral filter, a multichroic mirror, or a combination thereof. In some embodiments, the peak wavelength of electromagnetic radiation exciting the sample is between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm.

In some embodiments, the method further comprises separating the analyte from the sample. In some embodiments, separating the analyte from the sample comprises directing a hybrid polymer dot associated with the analyte to the flow cell of a flow cytometer or a microfluidic device. In some embodiments, separating the analyte from the sample comprises attaching a hybrid polymer dot associated with the analyte to a solid support. In some embodiments, separating the analyte from the sample comprises attaching a hybrid polymer dot associated with the analyte to a particle (e.g., bead or magnetic bead).

In some embodiments, compositions, methods and systems of the present disclosure are used for immunoassays including, but not limited to, immunocytochemistry, immunohistochemistry and enzyme-based assays. In some embodiments, the immunoassay is used to detect an analyte comprising a polypeptide such as a protein. In some embodiments, an antibody is bound indirectly to a hybrid polymer dot, e.g., by conjugation to a functional group that is attached to the polymer dot. In some embodiments, the antibody is a primary antibody. In some embodiments the antibody is a secondary antibody. In some embodiments both a primary antibody and a secondary antibody are bound indirectly to a hybrid polymer dot. In some embodiments, the assay is performed on cells that have been dissociated from a tissue. In other embodiments, the assay is performed on intact (non-dissociated) tissue. In some embodiments, hybrid polymer dots are used to perform enzyme-based assays, such as an enzyme-linked immunosorbent assay (ELISA).

In some embodiments, compositions, methods and systems of the present disclosure are used for analysis of polynucleotides, including but not limited to polymerase chain reaction, reverse transcriptase PCR, ligase chain reaction, loop mediated amplification, reverse transcription loop mediated amplification, helicase dependent amplification, reverse transcription helicase dependent amplification, recombinase polymerase amplification, reverse transcription recombinase polymerase amplification, catalytic hairpin assembly reactions, hybridization chain reaction, entropy-driven catalysis, strand displacement amplification, reverse transcription strand displacement amplification, nucleic acid sequence based amplification, transcription mediated amplification, self-sustained sequence replication, single primer isothermal amplification, signal mediated amplification of RNA technology, rolling circle amplification, hyper branched rolling circle amplification, exponential amplification reaction, smart amplification, isothermal and chimeric primer-initiated amplification of nucleic acids, multiple displacement amplification, and/or in situ hybridization.

In some embodiments, compositions, methods and systems of the present disclosure are used for analysis of metabolites including lipids, sugars, nucleotides, amino acids, fatty acids and other metabolites.

In some embodiments, compositions, methods and systems of the present disclosure are used for detecting cells, including but not limited to eukaryotic cells in vitro, eukaryotic cells in vivo, and prokaryotic bacterial cells.

In some embodiments, compositions, methods and systems of the present disclosure are used for detecting organelles and other subcellular fractions including but not limited to mitochondria, endoplasmic reticulum and/or synaptosomes.

In some embodiments, compositions methods and systems of the present disclosure are used for detecting biomarkers in a bioassay. The biomarker can be, without limit, a polypeptide such as a protein, a polynucleotide such as DNA and/or RNA, a metabolite such as a lipid, fatty acid, sugar, nucleotide or amino acid, a cell, a virus or viral particle.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The compositions and methods of the present disclosure are further illustrated by the following non-limiting examples.

Example 1

Preparation of Hybrid Polymer Dots Using TEOS

This example demonstrates a method of making organic-inorganic hybrid polymer dots for subsequent characterization, bioconjugation, and biological applications. This method includes the use of tetraethyl orthosilicate (TEOS).

Three solutions of tetrahydrofuran (THF) containing a semiconducting polymer, alkylsilane, and tetraethyl orthosilicate (TEOS), respectively, are prepared, and all of the THF solutions are mixed to form a homogenous solution. The mixed solution is quickly injected into an aqueous solution under ultrasonication in an ultrasonic cleaning bath. The aqueous solution comprises an alkylsilane having a functional group suitable for bioconjugation, for example, carboxylic acid, carboxylate, or primary amine. The pH value of the aqueous solution is adjusted with ammonia to a pH of approximately 11.

The hybrid polymer dots are obtained after removal of THF under heating with $N_2$ stripping. Alcohols formed during the hydrolysis of silanes and ammonia are removed together with THF. The final hybrid Pdot solution shows a pH value that is close to neutral, i.e., approximately 7.

Example 2

Preparation of Hybrid Polymer Dots without TEOS

This example demonstrates a method of making organic-inorganic hybrid polymer dots for subsequent characterization, bioconjugation, and biological applications. This method does not include the use of tetraethyl orthosilicate (TEOS).

Two solutions of tetrahydrofuran (THF) containing a semiconducting polymer, and alkylsilane, respectively, are prepared, and both of the THF solutions are mixed to form a homogenous solution. The mixed solution is quickly injected into an aqueous solution under ultrasonication in an ultrasonic cleaning bath. The aqueous solution comprises an alkylsilane having a functional group suitable for bioconjugation, for example, carboxylic acid, carboxylate, or primary amine. The pH value of the aqueous solution is adjusted with ammonia to a pH of approximately 11.

The hybrid polymer dots are obtained after removal of THF under heating with $N_2$ stripping. Alcohols formed during the hydrolysis of silanes and ammonia are removed together with THF. The final hybrid Pdot solution shows a pH value that is close to neutral, i.e., approximately 7.

Example 3

Preparation and Characterization of Hybrid Polymer Dots

This example demonstrates a method of making organic-inorganic hybrid polymer dots according to the method of Example 1 for subsequent characterization, bioconjugation, and biological applications.

Three solutions of tetrahydrofuran (THF) containing a semiconducting polymer, alkylsilane, and TEOS, respectively, were prepared. Table 1 provides the semiconducting polymers used, and additionally provides the composition ratios of the polymer to the alkylsilane and TEOS. The alkylsilane used was either tetramethyl orthosilicate (TMOS) or TCOS (chemical structure shown in FIG. 2), as provided in Table 1.

All of the THF solutions were mixed so as to form a homogenous solution. The mixed solution was quickly injected into an aqueous solution under ultrasonication in an ultrasonic cleaning bath. The aqueous solution comprises an alkylsilane with a functional group suitable for bioconjugation, for example, carboxylic acid, carboxylate, or primary amine. The pH value of the aqueous solution is adjusted with ammonia to a pH of approximately 11.

The hybrid polymer dots were obtained after removal of THF under heating with $N_2$ stripping. Alcohols formed during the hydrolysis of silanes and ammonia were removed together with THF. The final hybrid Pdot solution showed a pH value that is close to neutral, i.e., approximately 7.

Table 1 shows the size of the polymer dots as measured by dynamic light scattering (DLS), the zeta potential (ζ), and the fluorescence quantum yield (QY). As shown in Table 1, the hybrid polymer dots show higher fluorescence quantum yields than those of the respective bare polymer dots. This indicates the significance of the formation of organic-inorganic interpenetrated structures. These results also emphasize this general strategy for improving the optical properties and stability of the polymer dots.

TABLE 1

| Pdots | | Size (nm) | ξ (mV) | QY (%) |
|---|---|---|---|---|
| PFO | Bare | 21 | −42 | 45 |
| | /TOMS/TEOS(1:1:1) | 24 | −47 | 47 |
| | /TCOS/TEOS(1:1:1) | 15.7 | −42 | 51 |
| PFPV | Bare | 13.5 | −48 | 7 |
| | /TMOS/TEOS(1:1:1) | 13.5 | −43 | 9.1 |
| | /TCOS/TEOS(1:1:1) | 11.7 | −41 | 11.2 |
| MEH-PPV | Bare | 21 | −50 | 1.2 |
| | /TMOS/TEOS(1:1:1) | 18 | −41 | 1.7 |
| | /TCOS/TEOS(1:1:1) | 13.5 | −39 | 1.8 |
| CNPPV | Bare | 11.7 | −42 | 45 |
| | /TMOS/TEOS(1:1:1) | 11.7 | −46 | 50 |
| | /TCOS/TEOS(1:1:1) | 8.7 | −40 | 51 |
| BODIPY 590 | Bare | 24 | −51 | 6 |
| | /TMOS/TEOS(1:1:1) | 24 | −46 | 8.3 |
| | /TCOS/TEOS(1:1:1) | 13.5 | −45 | 11 |
| PFTBT | Bare | 33 | −45 | 44 |
| | /TMOS/TEOS(1:1:1) | 44 | −50 | 54 |
| | /TCOS/TEOS(1:1:1) | 15.7 | −40 | 52 |
| BODIPY 680 | Bare | 16 | −41 | 19 |
| | /TMOS/TEOS(1:1:1) | 24 | −57 | 23 |
| | /TCOS/TEOS(1:1:1) | 10 | −40 | 26 |

Example 4

Preparation of Hybrid Polymer Dots Using PFBT

This example demonstrates a method of making organic-inorganic hybrid polymer dots for subsequent characterization, bioconjugation, and biological applications.

PFBT, a chromophoric polymer, was dissolved in tetrahydrofuran (THF) by stirring under inert atmosphere to make a solution with a concentration of 1 mg/mL. TMOS, an organic alkylsilane, was dissolved in THF to make a solution with concentration of 1 mg/mL. Alternatively, TCOS can be used as the organic alkylsilane. TEOS, an organic silane, was dissolved in THF to make a solution with concentration of 1 mg/mL. The PFBT, TMOS (or TCOS), and TEOS solutions were diluted into THF to form 2 mL of a mixed homogenous solution containing PFBT at a concentration of 0.1 mg/mL. A $10^{-3}$ M aqueous solution of Silane-COONa was then prepared, and the pH value of this solution was adjusted to approximately 11. The 2 mL quantity of the PFBT solution mixture was quickly added to 10 mL of the above-prepared aqueous Silane-COONa solution while sonicating the mixture. THF was removed by nitrogen stripping, and the solution was concentrated by continuous nitrogen stripping to 2 mL on a hotplate at 90° C., which was followed by filtration through a 0.2 micron filter.

FIG. 2 provides chemical structures of the chromophoric polymer polyfluorene-benzothiadiazole, as well as organic alkylsilane molecules such as TMOS, TCOS, and TEOS. A functional silane molecule with carboxylate groups, such as Silane-COONa is also illustrated in the FIG. 2.

The resulting nanoparticle dispersions are clear and stable for months with no signs of aggregation. The hybrid polymer dots are further characterized and conjugated to biomolecules for fluorescence imaging applications.

Example 5

Preparation of Bare and Hybrid Polymer Dots

This example demonstrates a method of making organic-inorganic hybrid polymer dots according to the methods of Examples 1 or 2 for subsequent characterization, bioconjugation, and biological applications.

Hybrid polymer dots were prepared according to Examples 1 or 2, where the polymer, alkyl silane, and optional TEOS were provided as in Table 2.

As shown in Table 2, the hybrid polymer dots show higher fluorescence quantum yields than those of the respective bare polymer dots (polymer dots without an inorganic network). This indicates the significance of the formation of organic-inorganic interpenetrated structures. These results also emphasize this general strategy for improving the optical properties and stability of the polymer dots.

TABLE 2

| Pdots | Size (nm) | ξ (mV) | QY % |
|---|---|---|---|
| PFBT bare | 21 | −54 | 15.3 |
| PFBT/TMOS(1:1) | 21 | −54 | 18.9 |
| PFBT/TMOS(1:10) | 33 | −54 | 35.2 |
| PFBT/TMOS/TEOS(1:1:10) | 21 | −49 | 19.5 |
| PFBT/TCOS(1:1) | 15.7 | −25 | 18.5 |
| PFBT/TCOS(1:10) | 13.5 | −38 | 19.4 |
| PFBT/TCOS/TEOS(1:1:10) | 15.7 | −42 | 19.0 |

Example 6

Size, Surface Potential, and Fluorescence Quantum Yield Characterizations of Hybrid Polymer Dots This example demonstrates the assessment of the particle size, surface potential, and fluorescence quantum yield of hybrid polymer dots.

Hybrid polymer dots were prepared according to Examples 1 or 2, where the polymer, alkyl silane, and optional TEOS were provided as in Table 3.

The particle sizes and surface potentials of the hybrid polymer dots were measured by using Malvern Nanosizer ZS. UV-Vis absorption spectra were recorded using a DU 720 spectrophotometer using a 1 cm quartz cuvette. Fluorescence spectra were collected with a Fluorolog-3 fluorometer using a 1 cm quartz cuvette. Fluorescence quantum yields of the hybrid polymer dots were collected using an integrating sphere (Model C9920-02, Hamamatsu Photonics) with a 460 nm excitation from a 150 W CW Xenon lamp.

Table 3 summarizes the particle size, surface potential, and fluorescence quantum yield data. As seen from Table 3, the hybrid polymer dots have comparable or smaller particles sizes as compared to those of bare polymer dots. However, the hybrid polymer dots have higher quantum yields as compared to the bare polymer dots. This indicates improved fluorescence properties of the hybrid polymer dots.

TABLE 3

| Pdots | Size (nm) | ξ (mV) | QY % |
|---|---|---|---|
| PFBT bare 20 ppm | 28 | −52.5 | 15.7 |
| PFBT:TMOS:TEOS 20:10:10 (ppm) | 21 | −38.5 | 17.3 |
| PFBT:TMOS:TEOS 20:20:20 (ppm) | 18 | −46.5 | 19.6 |
| PFBT:TCOS:TEOS 20:10:10 (ppm) | 18 | −46.2 | 16.1 |
| PFBT:TCOS:TEOS 20:20:20 (PPM) | 16 | −45.8 | 20.9 |
| PFBT:TMOS:TEOS 20:5:5 (ppm) | 21 | −38.8 | 17.6 |
| PFBT:TMOS:TEOS 20:10:10 (ppm) | 24 | −47.5 | 16.5 |
| PFBT:TMOS:TEOS 20:20:20 (ppm) | 28 | −50.0 | 19.6 |
| PFBT:TMOS:TEOS 20:40:40 (ppm) | 32 | −51.2 | 19.9 |
| PFBT:TCOS:TEOS 20:5:5 (ppm) | 18 | −39.4 | 15.8 |
| PFBT:TCOS:TEOS 20:10:10 (ppm) | 16 | −51.2 | 16.1 |
| PFBT:TCOS:TEOS 20:20:20 (ppm) | 18 | −50.5 | 21.1 |
| PFBT:TCOS:TEOS 20:40:40 (ppm) | 16 | −38.7 | 17.0 |

Example 7

Transmission Electron Microscopy Characterization of Hybrid Polymer Dots

This example demonstrates the assessment of the size, morphology, and monodispersity by transmission electron microscopy of hybrid polymer dots.

Hybrid polymer dots were prepared according to Example 1 to make hybrid polymer dots using PFBT, TMOS, and TEOS; PFBT, TCOS, and TEOS; and MEH-PPV, TMOS, and TEOS.

TEM measurements were made by placing one drop of a hybrid polymer dot dispersion on a copper grid. After evaporation of the water from the dispersion, the surface was imaged using TEM (FEI Tecnai F20, 200 kV). FIG. 3 shows representative TEM images of the hybrid polymer dots and bare polymer dots. The TEM results show that the hybrid polymer dots have improved monodispersity as compared to the bare polymer dots. Notably, the magnified TEM images of the hybrid polymer dots show that the hybrid polymer dots do not have a core-shell structure or a core-cap structure. This indicates that hydrolysis of the organic silane forms a silica network, and an interpenetrated hybrid network of the silica network and the semiconducting polymer is formed.

Example 8

Single-Particle Brightness of the Hybrid Polymer Dots

This example demonstrates a side-by-side single-particle emission brightness evaluation and comparison of hybrid polymer dots and bare polymer dots.

Hybrid polymer dots were prepared according to Example 1, where the polymer, alkyl silane, and TEOS were provided as in Table 4.

Hybrid polymer dots were diluted in Milli-Q water, dried under vacuum on cleaned glass coverslips, and imaged on a fluorescence microscope. The 488-nm laser beam from a sapphire laser (Coherent, Santa Clara, CA, USA) was directed into an inverted microscope (Nikon TE2000U, Melville, NY, USA) using lab-built steering optics. Laser excitation power was measured at the nosepiece before the objective. The objective used for illumination and light collection was a 1.45 NA 100× objective (Nikon, Melville, NY, USA). Fluorescence signal was filtered by a 500 nm long pass filter (HQ500LP; Chroma, Rockingham, VT, USA) and imaged on an EMCCD camera (Photometrics Cascade: 512B, Tucson, AZ USA). Fluorescence intensity emitted per frame for a given particle was estimated by integrating the CCD signal over the fluorescence spot.

Figure 4:
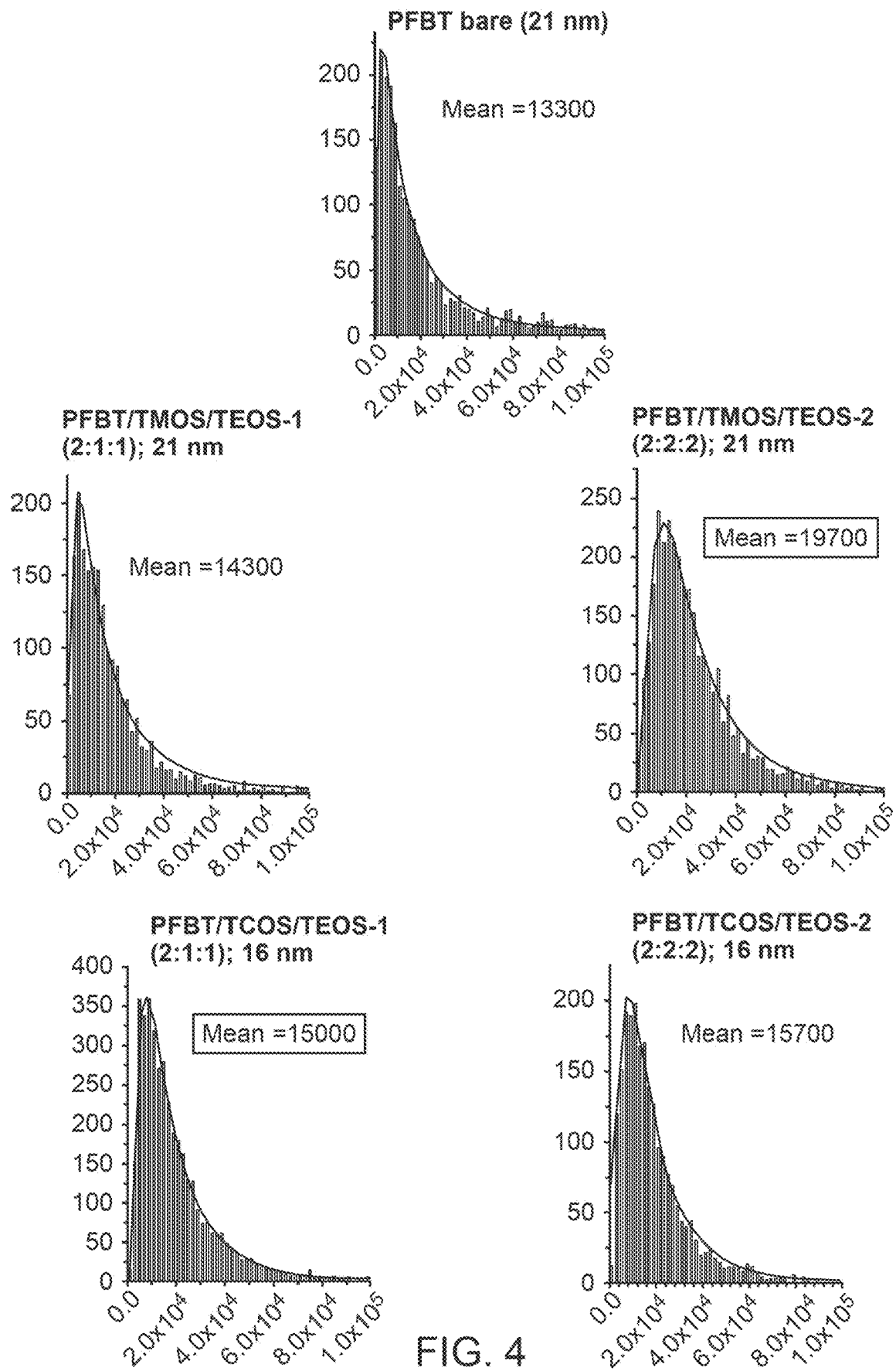
FIG. 4 illustrates comparative single particle fluorescence curves of bare PFBT polymer dots and the hybrid polymer dots prepared from PFBT, alkylsilane, and TEOS at different ratios.

FIG. 4 show single-particle intensity histograms obtained from fluorescence images under identical acquisition and laser excitation conditions. The results summarized in Table 4 show that the hybrid polymer dots prepared according to the methods disclosed herein exhibit an improvement in fluorescence signal as compared to that of bare polymer dots. Fluorescence brightness is the product of the peak absorption cross section and the fluorescence quantum yield. Based on the quantum yield values, such an improvement indicates that the per-particle absorption cross sections of the hybrid polymer dots are comparable to that of the bare polymer dots. This indicates that the number of chromophoric polymer chains packed in the hybrid polymer dots is similar to that in the bare polymer dots. This indicates that, although bare polymer dots are generally larger than the hybrid polymer dots, the hybrid polymer dots have a more compact internal structure. Furthermore, the formation of the interpenetrated network may reduce self-quenching of the polymers when they are compacted closely together.

TABLE 4

| Pdots | Size (nm) | Single particle brightness (CCD account) |
|---|---|---|
| PFBT bare 20 ppm | 21 | 13300 |
| PFBT:TMOS:TEOS 20:10:10 (ppm) | 21 | 14300 |
| PFBT:TCOS:TEOS 20:20:20 (ppm) | 21 | 19700 |
| PFBT:TCOS:TEOS 20:10:10 (ppm) | 18 | 15000 |
| PFBT:TCOS:TEOS 20:20:20 (ppm) | 16 | 15700 |

Example 9

Biomolecular Conjugation of the Hybrid Polymer Dots for Cell Labeling

This example demonstrates bioconjugation utilizing an EDC-catalyzed reaction between carboxyl groups on the hybrid polymer dots and amine groups on biomolecules.

Hybrid polymer dots were prepared according to Example 1 to make hybrid polymer dots using PFBT, TMOS, and TEOS at ratios of 2:1:1 and 2:2:2, as well as hybrid polymer dots using PFBT, TCOS, and TEOS at ratios of 2:1:1 and 2:2:2.

60 µL of polyethylene glycol (5% w/v PEG, MW 3350) and 60 µL of concentrated HEPES buffer (1 M) were added to 3 mL of the hybrid polymer dot solution (50 µg/mL in MilliQ water), resulting in a hybrid polymer dot solution in 20 mM HEPES buffer with a pH of 7.3. Then, 180 µL of streptavidin was added to the solution and mixed well by vortexing. Alternatively, IgG antibody (1 mg/mL) can be used in place of 180 µL of streptavidin. 60 µL of 1-ethyl-3-[3-dimethylaminopropyl]carbodiimide hydrochloride (EDC) solution (5 mg/mL in MilliQ water) was added to the vortexed solution, and the mixture was left on a rotary shaker for 4 hours at room temperature. The resulting hybrid polymer dot-streptavidin bioconjugates were separated from free biomolecules by gel filtration using Sephacryl HR-300 gel media.

MCF-7 and SK-BR-3 breast cancer cell lines were ordered from American Type Culture Collection (ATCC, Manassas, VA, USA). Cells were cultured at 37° C. in 5% $CO_2$ in Eagles minimum essential medium (for MCF-7) or McCoy's 5A medium (for SK-BR-3) supplemented with 10% Fetal Bovine Serum (FBS), 50 U/mL penicillin, and 50 µg/mL streptomycin. The cells were pre-cultured prior to experiments until confluence was reached. The cells were harvested from the culture flask by briefly rinsing with culture media, which was followed by incubation with 5 mL of Trypsin-EDTA solution (0.25 w/v % Trypsin, 0.53 mM EDTA) at 37° C. for 5-15 minutes. After complete detachment, the cells were rinsed, centrifuged, and resuspended in labeling buffer (1×PBS, 2 mM EDTA, 1% BSA). The cell concentration was determined by microscopy using a hemacytometer.

The hybrid polymer dot-streptavidin bioconjugates were used as probes to detect EpCAM. In order to label a cell-surface marker with hybrid polymer dot-streptavidin bioconjugates, live MCF-7 cells in the glass-bottomed culture dish were incubated sequentially with 5 µg/mL primary anti-human CD326 antibody, 5 µg/mL biotinylated secondary anti-mouse IgG (Biolegend, San Diego, CA, USA), and 5 nM hybrid Pdot-streptavidin for 30 minutes each. Two washing steps were performed after each incubation. The hybrid polymer dot-tagged cells were imaged immediately on a fluorescence confocal microscope (Zeiss LSM 510). As shown by the confocal imaging, the hybrid polymer dot-streptavidin bioconjugates, together with the biotinylated primary anti-EpCAM antibody, effectively labeled EpCAM on the surface of live MCF-7 cells When the cells were incubated with hybrid polymer dot-streptavidin bioconjugates in the absence of biotin primary antibody, no fluorescence was observed on the cell surface, which shows the highly specific binding of the hybrid polymer dot-streptavidin bioconjugates. The lack of signal also indicated the absence of nonspecific binding in this biotin-streptavidin labeling system.

FIG. 6 and FIG. 8 provide fluorescence imaging of MCF cells labeled with hybrid polymer dot bioconjugates.

Figure 11:
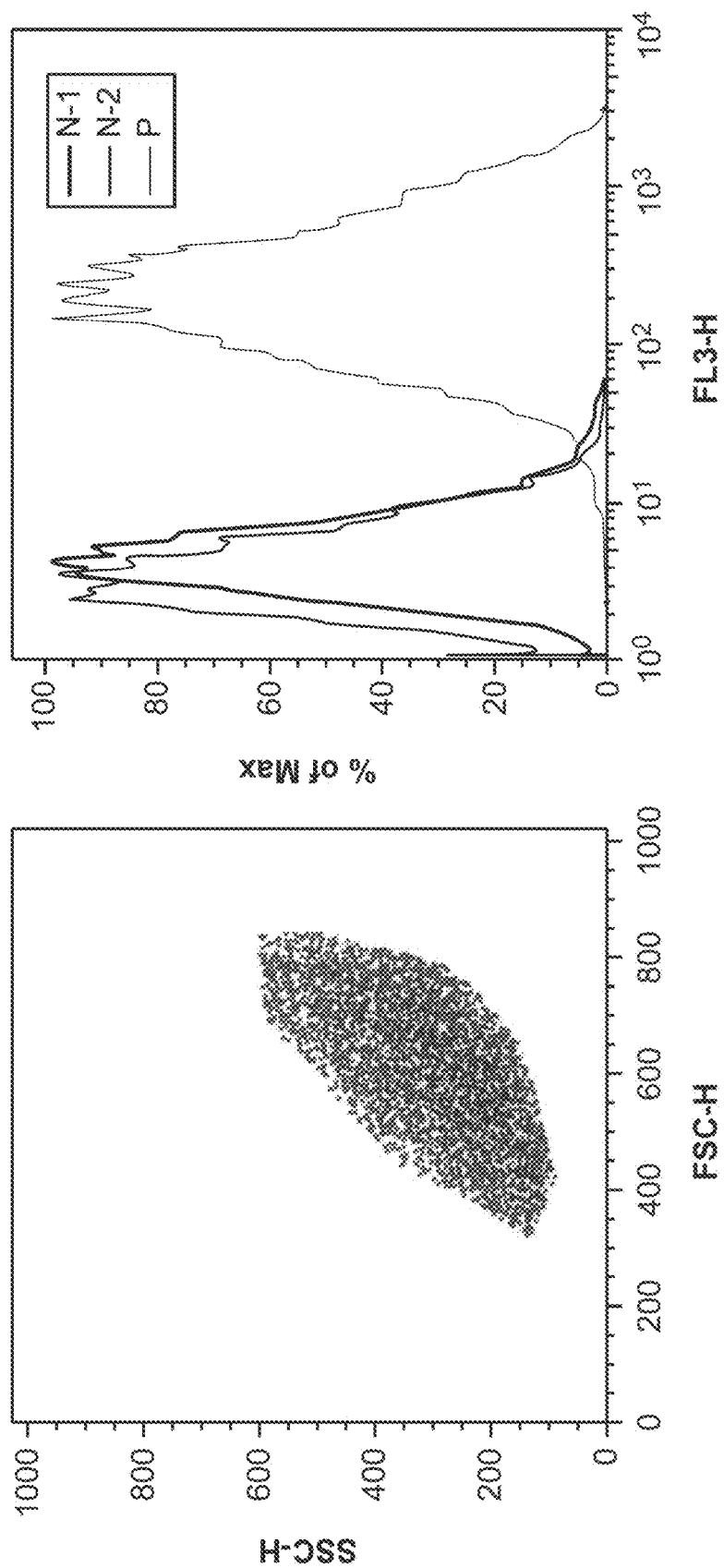
FIG. 11 shows flow cytometry results of MCF-7 cells labeled with the hybrid polymer dots.

In addition to fluorescence imaging, flow cytometry was used to evaluate the labeling brightness of the hybrid polymer dot-streptavidin bioconjugates. FIG. 11 shows flow cytometry results of MCF-7 cells labeled with the hybrid polymer dots. "N-1" indicates control cells incubated with hybrid polymer dots without streptavidin. "N-2" indicates control cells incubated with hybrid polymer dot-streptavidin bioconjugates in the absence of biotinylated primary antibody. "P" indicates cells incubated with hybrid polymer dot-streptavidin bioconjugates and biotinylated primary antibody. Fluorescence was observed for the "P" group only, indicating the highly specific binding of the hybrid polymer dot-streptaviding bioconjugates.

Figure 5:
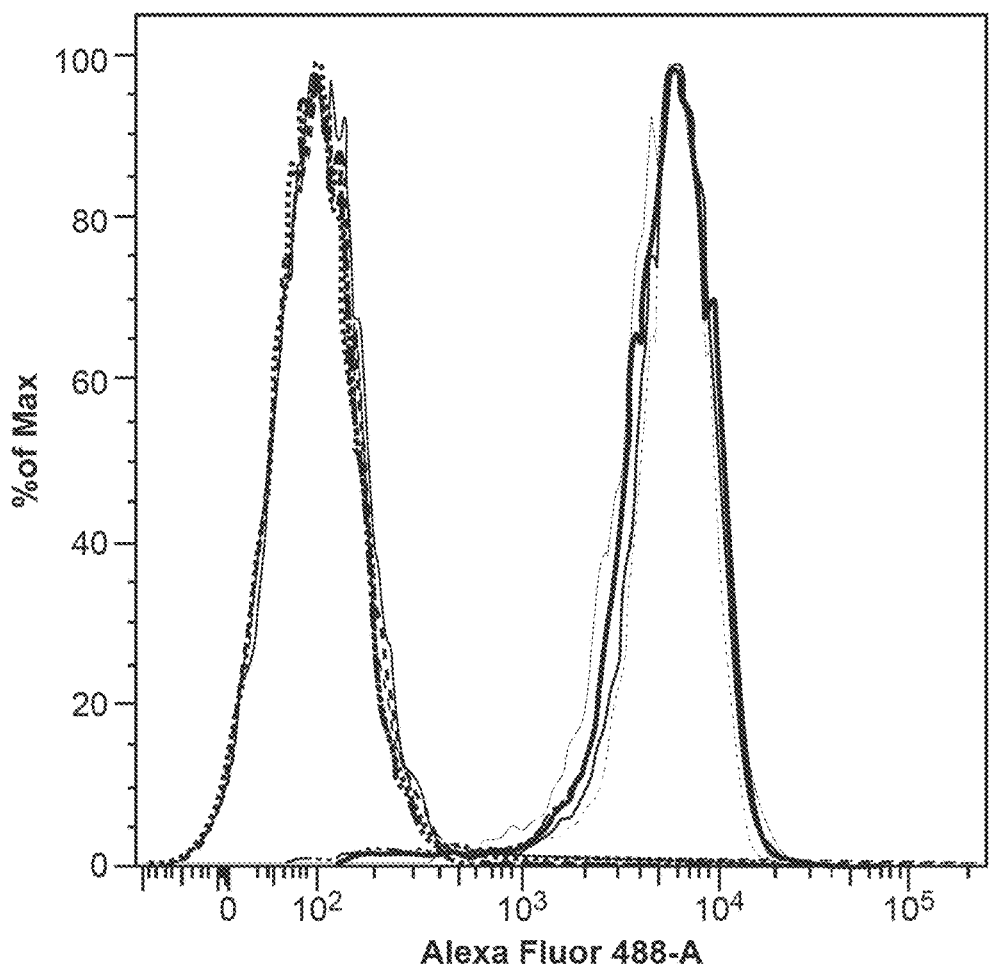
FIG. 5 illustrates cellular labeling brightness for different hybrid polymer dot bioconjugates as well as bare polymer dot bioconjugates, as quantified by flow cytometry.

FIG. 5 shows the flow cytometry results of the MCF-7 cells labeled with hybrid polymer dot-streptavidin bioconjugates as compared to bare polymer dot bioconjugates. In FIG. 5, Pdot-1 is PFBT/PS-PEG-COOH(20%); Pdot-2 is PFBT/TMOS/TEOS=2/1/1; Pot-3 is PFBT/TMOS/TEOS=2/2/2; Pdot-4 is PFBT/TCOS/TEOS=2/1/1; Pdot-5 is PFBT/TMOS/TEOS=2/2/2; -N indicates negative controls, where cells were not incubated with biotinylated primary antibody, and were directly incubated with hybrid polymer dot-streptavidin conjugates without biotinylated primary antibody; and -P indicates positive labeling. The results indicate that the hybrid polymer dots exhibit similar or slightly higher cell-labeling brightness as compared to the polymer dots functionalized by the PS-PEG-COOH blending method, the bare polymer dots.

Example 10

Photostability of the Hybrid Polymer Dots for Cell Labeling

This example demonstrates photostability measurements of the cells labeled with hybrid polymer dot bioconjugates.

Hybrid polymer dots were prepared according to Example 1 to make hybrid polymer dots using PFBT, TMOS, and TEOS at ratios of 2:1:1 and 2:2:2, as well as hybrid polymer dots using PFBT, TCOS, and TEOS at ratios of 2:1:1 and 2:2:2.

Figure 7:
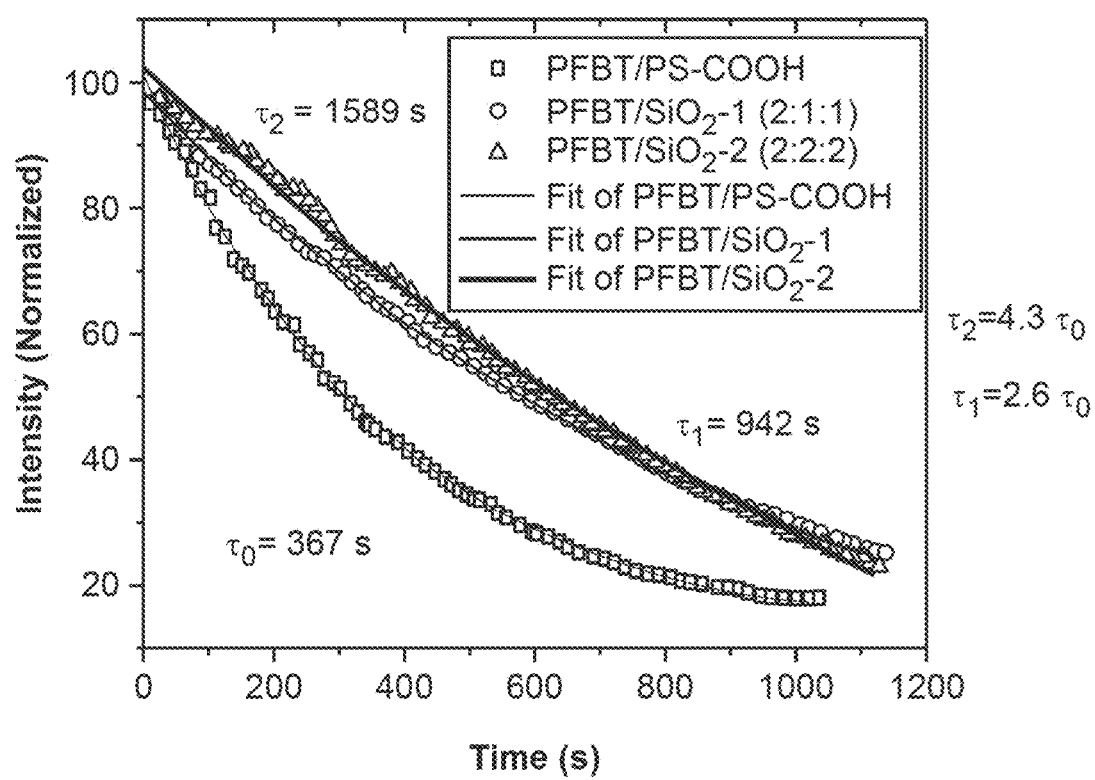
FIG. 7 illustrates photostability of the MCF cells labeled with the hybrid polymer dot bioconjugates.
Figure 9:
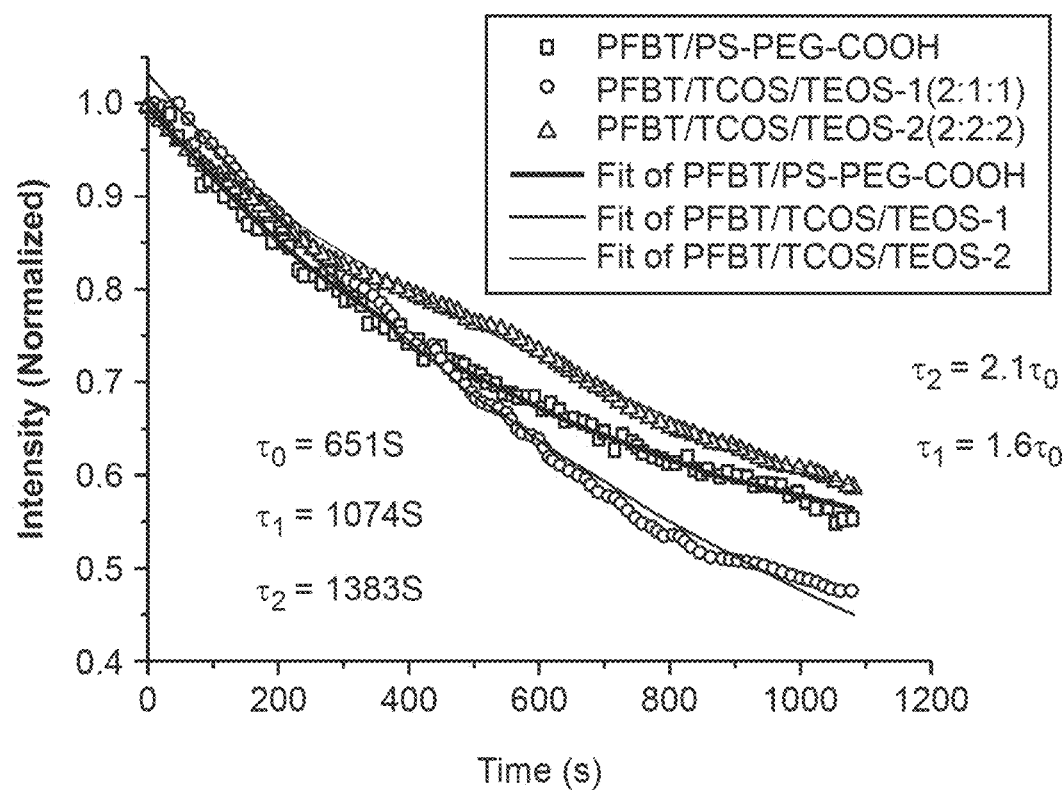
FIG. 9 illustrates photostability curves of the MCF cells labeled with the hybrid polymer dot bioconjugates.

MCF-7 cells were labeled as provided in Example 8. The hybrid polymer dot bioconjugate labeled cells were imaged on a fluorescence confocal microscope (Zeiss LSM 510). For photobleaching studies, confocal fluorescence images were recorded continuously for the cells labeled with the hybrid polymer dots and those labeled with the polymer dots blended with PS-PEG-COOH. Photobleaching data points were extracted by analyzing the fluorescence images using a custom-coded Matlab program. As shown in FIG. 7 and FIG. 9, photobleaching curves extracted from the fluorescence images indicate that the hybrid polymer dot were more photostable than the polymer dots functionalized by the PS-PEG-COOH blending method.

Example 11

Gel Electrophoresis of Hybrid Polymer Dots and Related Bioconjugates

This example demonstrates the characterization of the functional groups on the surface of the hybrid polymer dots using gel electrophoresis.

Figure 10:
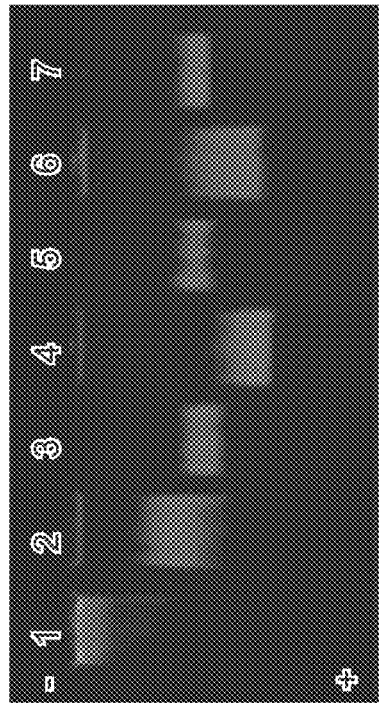
FIG. 10 illustrates results of gel electrophoresis of the hybrid polymer dots and related bioconjugates.

Gel electrophoresis was performed using a 0.7% agarose gel. Agarose gel electrophoresis of functionalized hybrid polymer dots was carried out using a Mupid®-exU submarine electrophoresis system. The functionalized hybrid polymer dots, in 30% glycerol, were loaded onto a 0.7% agarose gel containing 0.1% polyethylene glycol. The functionalized hybrid polymer dot-loaded gel was run for 20 min at 135 V in tris-borate-EDTA (TBE) buffer, and then imaged on a Kodak image station 440CF system. As shown in FIG. 10, compared to unfunctionalized, bare polymer dots, the functionalized hybrid polymer dots exhibited an increase in mobility in the gel. Notably, once the hybrid polymer dots are conjugated to streptavidin, the hybrid polymer dot-streptavidin bioconjugates show decreased mobility. This can be used to detect successful bioconjugation.

Example 12

Determination of Network Structure for Hybrid Polymer Dots

This example demonstrates the characterization of the interpenetrated network generated in formation of the hybrid polymer dots utilizing TEM and flow cytometry.

Interpenetrated hybrid polymer dots were prepared as according to Example 1 using PFBT, TCOS, and TEOS, at a weight ratio of 1:1:1.

PFBT-14% $C_2$COOH, a functionalized chromophoric polymer, was dissolved in tetrahydrofuran (THF) by stirring under inert atmosphere to make a solution with concentration of 1 mg/mL. TCOS, an organic silane, was dissolved in THF to make a solution with concentration of 1 mg/mL. TEOS was dissolved in THF to make a solution with concentration of 1 mg/mL. The above solutions of PFBT-14% $C_2$COOH, TCOS, and TEOS were diluted into THF to form 2 mL of a mixed homogenous solution containing PFBT-14% $C_2$COOH at a concentration of 0.1 mg/mL. Deionized water was obtained and the pH value of it was adjusted to approximately 11. The 2 mL quantity of the PFBT-14% $C_2$COOH solution was quickly added to 10 mL of the aqueous solution while sonicating the mixture. THF was removed by nitrogen stripping, and the solution was concentrated by continuous nitrogen stripping to 2 mL on a hotplate at 90° C., which was followed by filtration through a 0.2 micron filter. This afforded hybrid polymer dots wherein the chromophoric polymer was directly functionalized with carboxyl groups, resulting in Pdots not interpenetrated with Silane-COONa.

Figure 15:
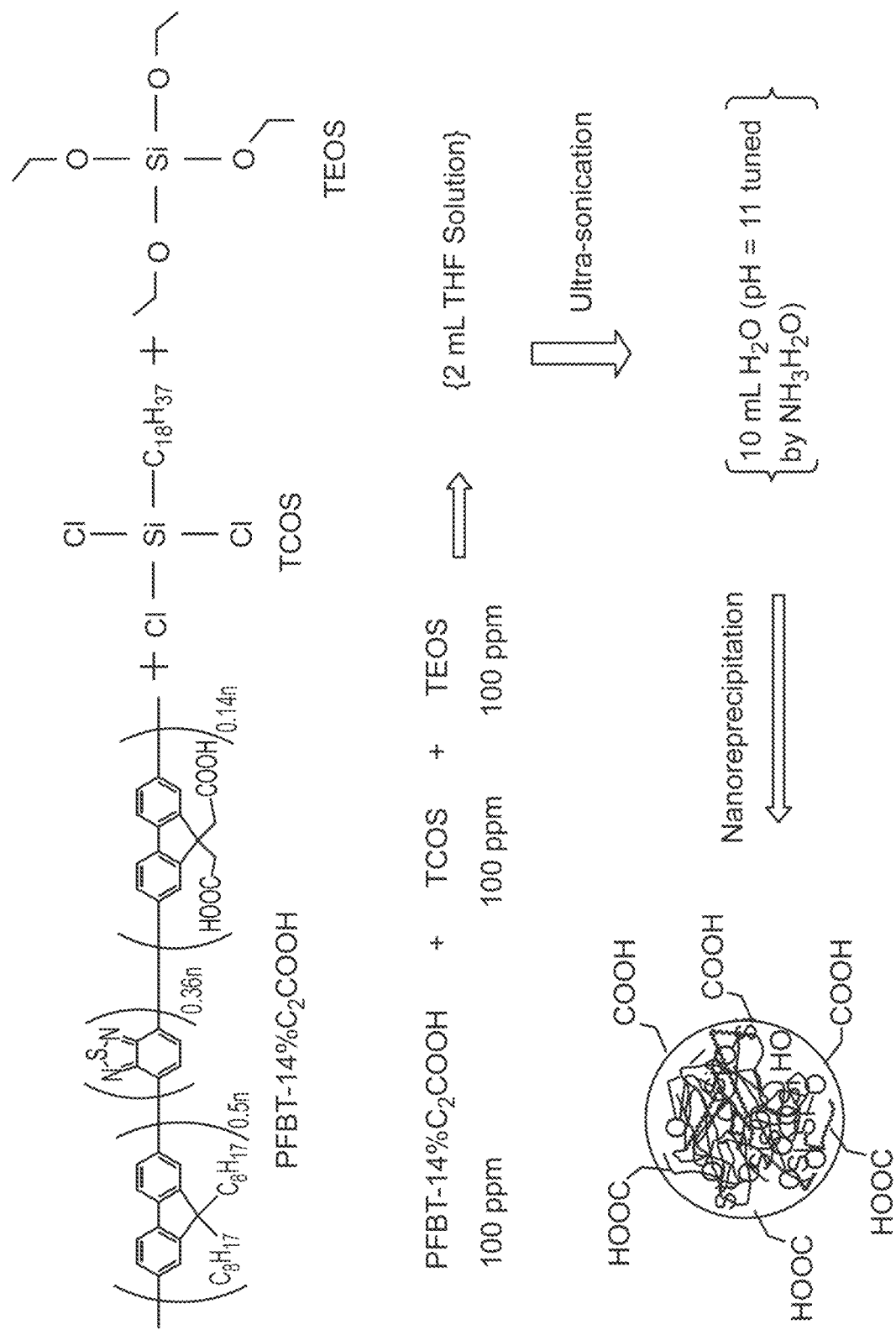
FIG. 15 illustrates a method of preparing carboxylate functionalized PFBT hybrid polymer dots with the use of a pre-functionalized PFBT polymer.

FIG. 15 provides chemical structures of the chromophoric polymer polyfluorene-benzothiadiazole PFBT-14% $C_2$COOH, as well as organic silane molecules such as TCOS and TEOS. A resultant polymer dot directly functionalized with carboxyl is also illustrated in FIG. 15.

Hybrid polymer dot-streptavidin bioconjugates were prepared as according to Example 8 to make PFBT-14% $C_2$COOH polymer dot-streptavidin bioconjugates as well as Silane-COONa polymer dot-streptavidin bioconjugates.

Figure 16:
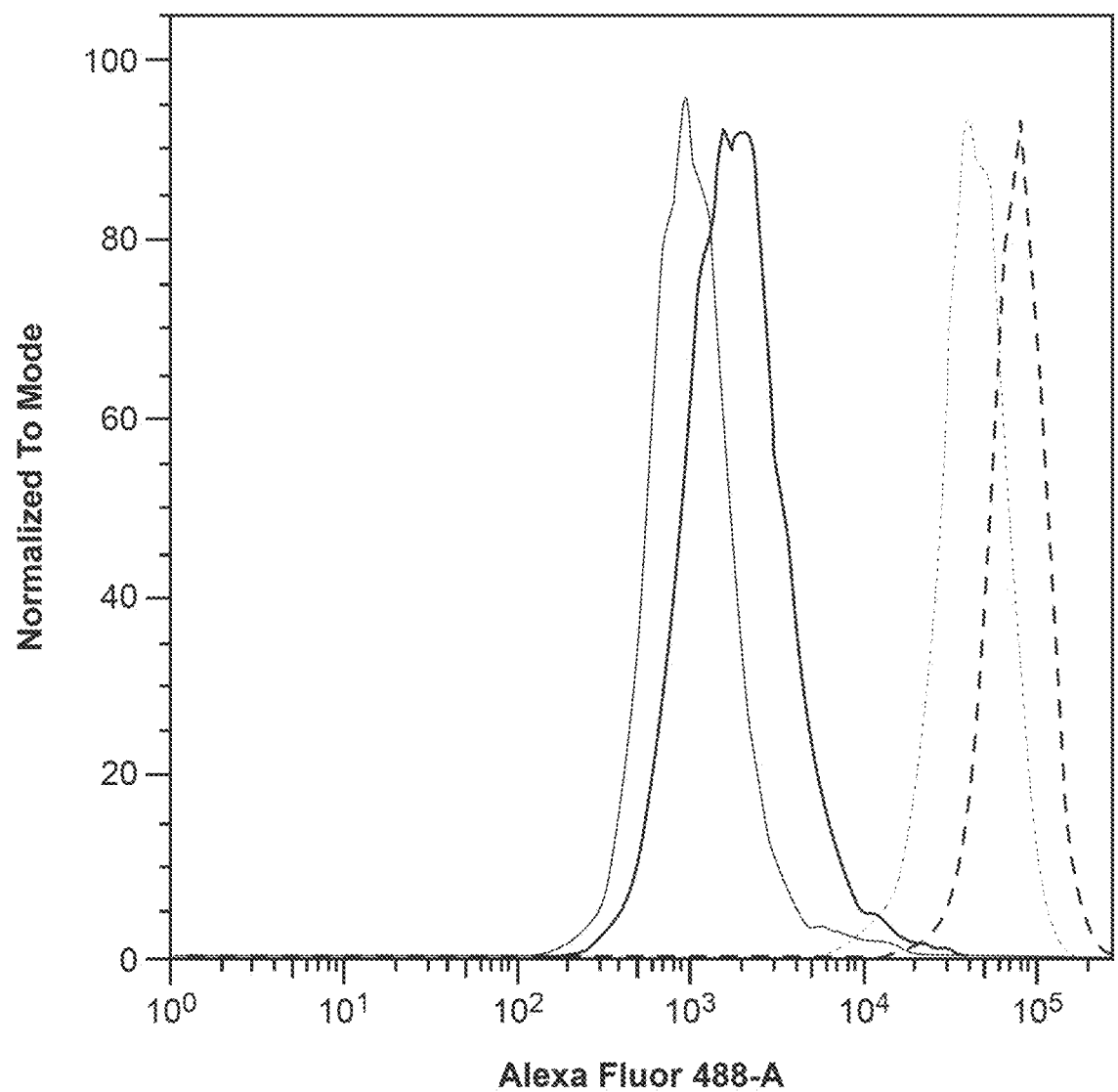
FIG. 16 shows flow cytometry results of MCF-7 cells labeled with functionalized PFBT hybrid dots with 14% of monomeric units comprising $C_2COOH$ (i.e., PFBT-14% $C_2COOH$), in comparison to those labeled with the Silane-COONa hybrid polymer dots.

Flow cytometry was used to evaluate the labeling brightness of the hybrid polymer dot-streptavidin bioconjugates, as according to Example 8. FIG. 16 shows flow cytometry results of MCF-7 cells labeled with the PFBT-14% $C_2$COOH hybrid polymer dots or labeled with the Silane-COONa hybrid polymer dots. "Negative of" indicates control cells incubated with hybrid polymer dot-streptavidin bioconjugates in the absence of biotinylated primary antibody. "Positive of" indicates cells incubated with the hybrid polymer dot-strepdavidin bioconjugates and biotinylated primary antibody. Fluorescence was observed for both of the "positive" groups, indicating the specific binding of streptavidin to carboxyl functionality applied to both types of Pdots generated. The result indicated that the external carboxyl availability of PFBT-14% $C_2$COOH hybrid polymer dots is similar to the external carboxyl availability of Silane-COONa hybrid polymer dots. This result indicated that the short carboxylic acid functional group of the PFBT backbone chain inside the Pdots is not encased by the silica network as a shell outside the hybrid Pdots, but instead exists as a part of an interpenetrated network formed between the polymer chains and silica network. The result of this flow cytometry experiment indicated that the hybrid polymer Pdots formed with a mesh-like structure, and do not have a distinct core-shell structure. This indicates that hydrolysis of the organic silane forms a silica network which interpenetrat with the semiconducting polymers and therefore formed a hybrid interpenetrated network.

Figure 17:
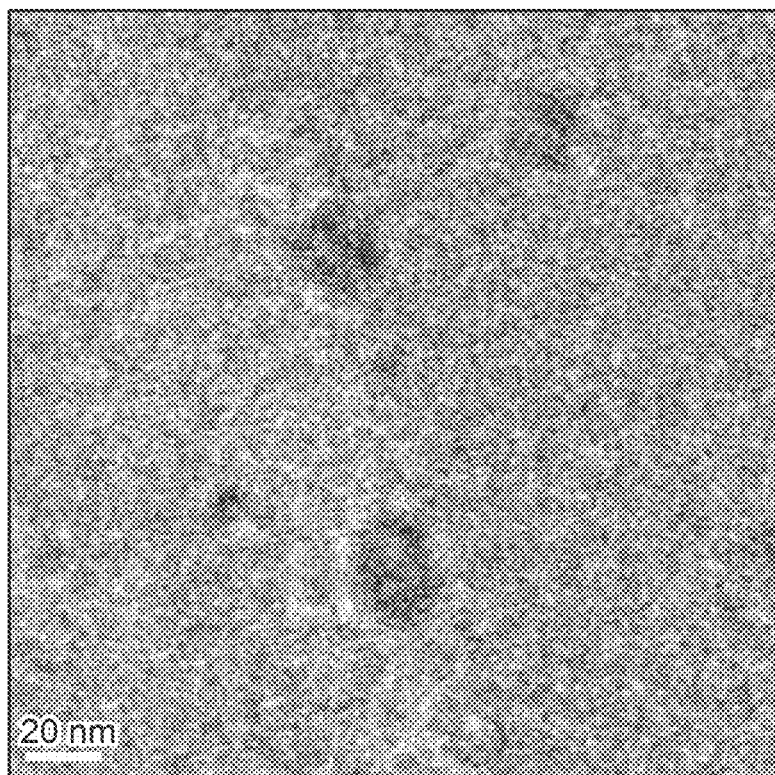
FIG. 17 provides a TEM image of the PFBT-14% $C_2COOH$ hybrid polymer dots.

TEM measurements were made by placing one drop of a hybrid polymer dot dispersion on a copper grid. After evaporation of the water from the dispersion, the surface was imaged using TEM (FEI Tecnai F20, 200 kV). FIG. 17 shows a representative TEM image of the PFBT-14% $C_2$COOH hybrid polymer dots. Notably, the magnified TEM images of the hybrid polymer dots show that the hybrid polymer dots do not have a core-shell structure or a core-cap structure. This furthermore indicates that hydrolysis of the organic silane forms a silica network, and then inside the hybrid Pdots an interpenetrated hybrid network between the silica network and the semiconducting polymer chains is formed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An organic-inorganic hybrid polymer dot comprising:
a semiconducting chromophoric polymer;
X, wherein X is a functional group suitable for bioconjugation;
an inorganic network that is covalently bonded to the semiconducting chromophoric polymer through a reactive chemical group that has orthogonal reactivity to X, wherein X is attached to the inorganic network, the semiconducting chromophoric polymer, or a combination thereof.

2. The organic-inorganic hybrid polymer dot of claim 1, wherein the semiconducting chromophoric polymer comprises a plurality of units, M, selected from:

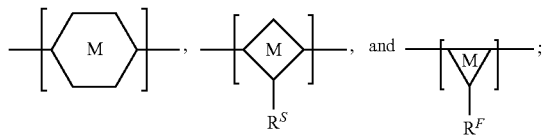

wherein:
$R^S$ is

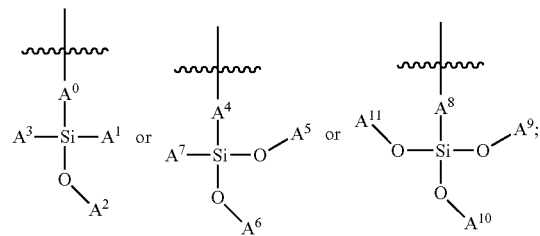

$R^F$ is

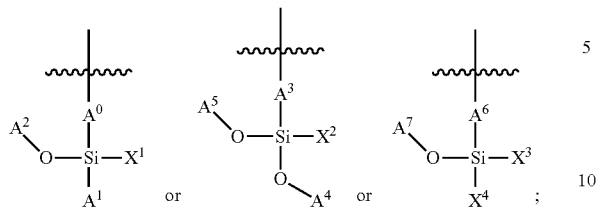

$A^0$, $A^4$, $A^8$, $A^{12}$, $A^5$, $A^{18}$, are each independently $C_nH_{2n}$ or $C_nF_{2n}$;

$A^1$, $A^2$, $A^3$, $A^5$, $A^6$, $A^7$, $A^9$, $A^{10}$, $A^{11}$, $A^{13}$, $A^{14}$, $A^{16}$, $A^{17}$, $A^{19}$ are each independently $C_mH_{2m+1}$ or $C_mF_{2m+1}$;

$X^1$, $X^2$, $X^3$, $X^4$ are each independently a functional group, wherein $X^1$, $X^2$, $X^3$, $X^4$ are X as defined in claim 1;

n is not less than 1; and m is not less than 1.

3. The organic-inorganic hybrid polymer dot of claim 1, wherein the semiconducting chromophoric polymer comprises a plurality of units, M, selected from:

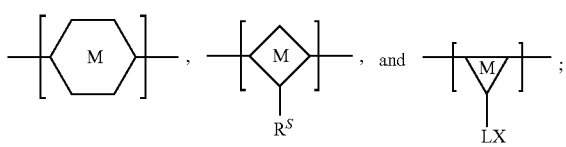

wherein:

$R^S$ is

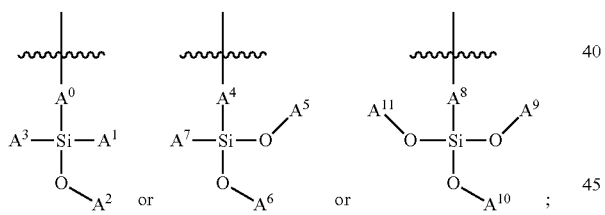

$A^0$, $A^4$, $A^8$, are each independently $C_nH_{2n}$ or $C_nF_{2n}$;

$A^1$, $A^2$, $A^3$, $A^5$, $A^6$, $A^7$, $A^9$, $A^{10}$, $A^{11}$, are each independently $C_mH_{2m+1}$ or $C_mF_{2m+1}$;

L is a linker moiety;

X is the functional group;

n is not less than 1; and m is not less than 1.

4. The organic-inorganic hybrid polymer dot of claim 1, wherein the semiconducting chromophoric polymer comprises a plurality of units, M, selected from:

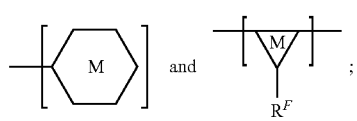

wherein:
$R^F$ is

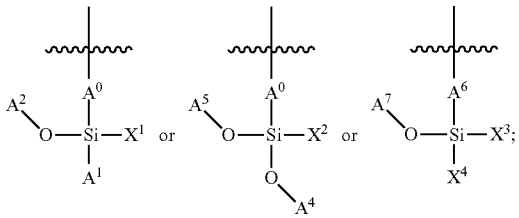

$A^0$, $A^3$, $A^6$ are each independently $C_{1n}H_{2n}$ or $C_nF_{2n}$;

$A^1$, $A^2$, $A^4$, $A^5$, $A^7$ are each independently $C_mH_{2m+1}$ or $C_mF_{2m+1}$;

$X^1$, $X^2$, $X^3$, $X^4$ are each independently a functional group, wherein $X^1$, $X^2$, $X^3$, $X^4$ are X as defined in claim 1;

n is not less than 1; and m is not less than 1.

5. The organic-inorganic hybrid polymer dot of claim 1, wherein the inorganic network comprises a siloxane network, an alumino-siloxane network, a titanium-siloxane network, a titanium oxide network, or a combination thereof.

6. The organic-inorganic hybrid polymer dot of claim 1, wherein the inorganic network comprises a siloxane network.

7. The organic-inorganic hybrid polymer dot of claim 6, wherein the siloxane network comprises a plurality of interconnected units, wherein the plurality of interconnected units comprises a unit selected from:

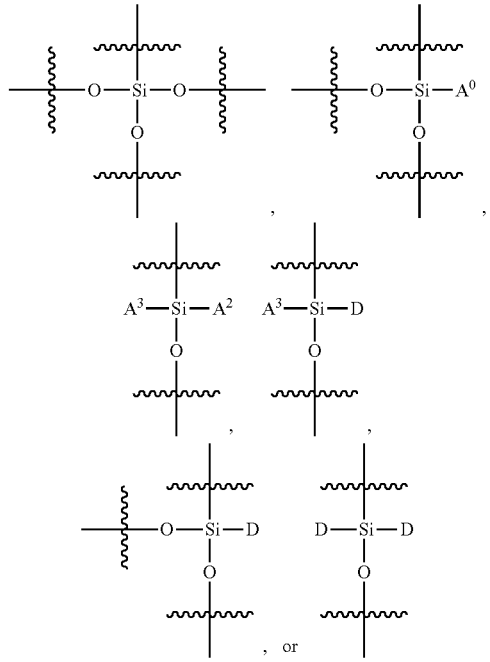

wherein:

$A^0$, $A^1$, $A^2$, $A^3$ are each independently $C_pH_{2n+1}$ or $C_pF_{2p+1}$;

D is LX, wherein L is a linker moiety;

X is the functional group; and p is not less than 1.

8. The organic-inorganic hybrid polymer dot of claim 7, wherein p is not less than 2; wherein p is not less than 3; wherein p is not less than 6; wherein p is not greater than 20;

wherein p is not greater than 40; wherein p is not greater than 60; or wherein p is not less than 6 and is not greater than 20.

9. The organic-inorganic hybrid polymer dot of claim 7, wherein X comprises an amine, a carboxylate, a carboxyl, a maleimide, a thiol, a maleic anhydride, an N-hydroxysuccinimide ester, a mercapto, an azido, an alkyne, an aldehyde, a hydroxyl, a carbonyl, a sulfate, a sulfonate, a phosphate, a cyanate, a succinimidyl ester, a strained alkyne, an azide, a diene, an alkene, a tetrazine, a strained alkene, a cyclooctyne, or a phosphine.

10. The organic-inorganic hybrid polymer dot of claim 7, wherein L is selected from a chemical bond, an amino acid, an ester, an amide, a carbamate, an ether, an alkylene, an alkenylene, an alkynylene, an arylene, a polyether, a polyester, a polyamide, a polycarbamate, a polyaryl, a polystyrene, or a polyolefin, or a fluorinated or partially fluorinated derivative thereof, or a combination thereof.

11. The organic-inorganic hybrid polymer dot of claim 7, wherein L is a water-soluble polymer.

12. The organic-inorganic hybrid polymer dot of claim 7, wherein L is a chemical bond.

13. The organic-inorganic hybrid polymer dot of claim 7, wherein at least one D is positioned on the surface of the polymer dot.

14. The organic-inorganic hybrid polymer dot of claim 7, further comprising a biological molecule conjugated to D.

15. The organic-inorganic hybrid polymer dot of claim 14, wherein the biological molecule comprises a protein or a nucleic acid.

16. The organic-inorganic hybrid polymer dot of claim 1, wherein the semiconducting chromophoric polymer and the inorganic network form an organic-inorganic interpenetrated network.

17. The organic-inorganic hybrid polymer dot of claim 16, wherein the organic-inorganic interpenetrated network is mesh-like.

* * * * *

UNITED STATES PATENT AND TRADEMARK OFFICE
CERTIFICATE OF CORRECTION

PATENT NO. : 12,272,468 B2  
APPLICATION NO. : 18/484587  
DATED : April 8, 2025  
INVENTOR(S) : Daniel T. Chiu et al.

Page 1 of 2

It is certified that error appears in the above-identified patent and that said Letters Patent is hereby corrected as shown below:

In the Claims

| Column | Line(s) | |
|---|---|---|
| 67 | 4-11 | Claim 2, delete |

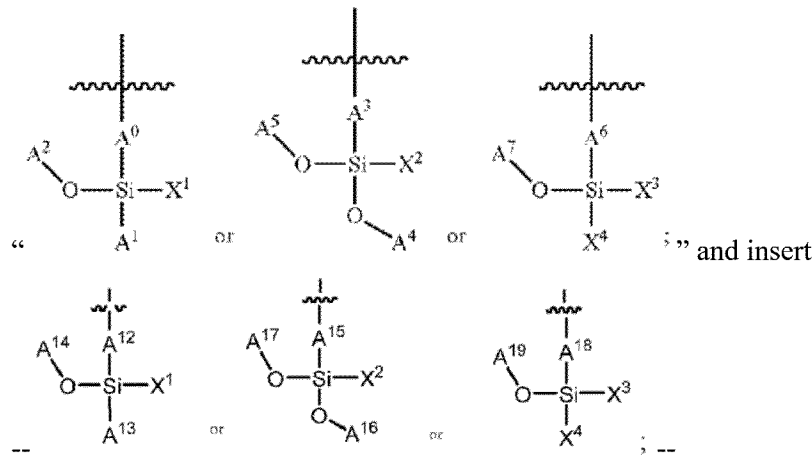

" and insert --

| 67 | 13 | Claim 2, delete "A⁵," and insert -- $A^{15}$, -- |

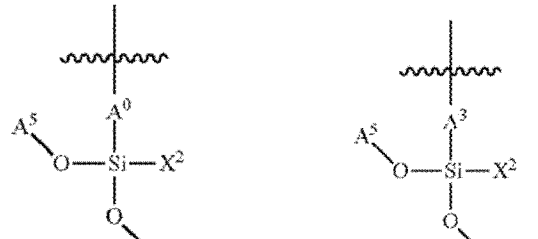

| 68 | 4-12 | Claim 4, delete " ... " and insert -- ... -- |
| 68 | 14 | Claim 4, delete "$C_{1n}H_{2n}$" and insert -- $C_nH_{2n}$ -- |

Signed and Sealed this  
Third Day of February, 2026

John A. Squires  
*Director of the United States Patent and Trademark Office*

68  42-49  Claim 7, delete " 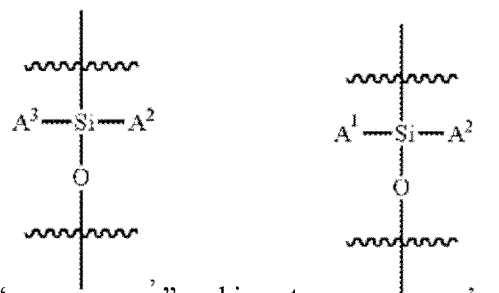 " and insert -- --